United States Patent
Borjas et al.

(10) Patent No.: US 11,324,802 B2
(45) Date of Patent: May 10, 2022

(54) C3 FUSION PROTEIN AND METHODS OF MAKING AND USING THEREOF

(71) Applicant: BioAxone BioSciences, Inc., Boston, MA (US)

(72) Inventors: Ricardo Borjas, Boston, MA (US); Mark Fleming, Boston, MA (US); Mei Huang, Boston, MA (US); Mayur Jain, Boston, MA (US); Tapan Sanghvi, Boston, MA (US); Kumkum Saxena, Boston, MA (US); Amaris Torres-Delgado, Boston, MA (US); Ping Yin, Boston, MA (US); Lisa McKerracher, Boston, MA (US); Elizabeth Ryu, Boston, MA (US)

(73) Assignee: BioAxone BioSciences, Inc., Boston, MA (US)

( * ) Notice: Subject to any disclaimer, the term of this patent is extended or adjusted under 35 U.S.C. 154(b) by 12 days.

(21) Appl. No.: 16/618,021

(22) PCT Filed: May 30, 2018

(86) PCT No.: PCT/US2018/035144
§ 371 (c)(1),
(2) Date: Nov. 27, 2019

(87) PCT Pub. No.: WO2018/222723
PCT Pub. Date: Dec. 6, 2018

(65) Prior Publication Data
US 2021/0138035 A1    May 13, 2021

Related U.S. Application Data

(60) Provisional application No. 62/675,659, filed on May 23, 2018, provisional application No. 62/675,680, filed on May 23, 2018, provisional application No. 62/675,714, filed on May 23, 2018, provisional application No. 62/512,661, filed on May 30, 2017, provisional application No. 62/512,673, filed on May 30, 2017, provisional application No. 62/512,695, filed on May 30, 2017.

(51) Int. Cl.
| | |
|---|---|
| *A61K 38/17* | (2006.01) |
| *A61K 38/36* | (2006.01) |
| *A61K 38/38* | (2006.01) |
| *A61K 38/57* | (2006.01) |
| *C07K 14/47* | (2006.01) |
| *C12N 9/10* | (2006.01) |

(52) U.S. Cl.
CPC ........ *A61K 38/1725* (2013.01); *A61K 38/363* (2013.01); *A61K 38/38* (2013.01); *A61K 38/57* (2013.01); *C07K 14/472* (2013.01); *C12N 9/1077* (2013.01); *C12Y 204/02036* (2013.01); *C07K 2319/70* (2013.01)

(58) Field of Classification Search
None
See application file for complete search history.

(56) References Cited

U.S. PATENT DOCUMENTS

| | | |
|---|---|---|
| 7,141,428 B2 | 11/2006 | McKerracher |
| 7,169,783 B2 | 1/2007 | McKerracher et al. |
| 7,491,692 B2 | 2/2009 | McKerracher |
| 7,795,218 B2 | 9/2010 | McKerracher et al. |
| 2008/0021026 A1 | 1/2008 | Kahraman et al. |
| 2010/0189696 A1 | 7/2010 | Sun et al. |
| 2012/0156230 A1 | 6/2012 | Abbot et al. |
| 2015/0297643 A1 | 10/2015 | McKerracher |

FOREIGN PATENT DOCUMENTS

| | | |
|---|---|---|
| WO | WO-2005/030248 A1 | 4/2005 |
| WO | WO-2008036459 A2 | 3/2008 |
| WO | WO-2008/077234 A1 | 7/2008 |
| WO | WO-2008/077236 A1 | 7/2008 |

OTHER PUBLICATIONS

TISSEEL (Highlights of prescribing information; 2013).*
You-Di Liao et al. (Protein Science (2004), 13:1802-1810).*
International Search Report and Written Opinion for International Application No. PCT/US2018/035144, dated Oct. 4, 2018 (12 pages).
Thuret et al., "Therapeutic Interventions After Spinal Cord Injury," Nat Rev Neurosci. 7(11): 628-643 (2006).
Black, "Cerebrospinal Fluid Leaks Following Spinal Surgery: Use of Fat Grafts for Prevention and Repair. Technical Note," J Neurosurg. 96(2):250-252 (2002).
Boomkamp et al., "The Development of a Rat in Vitro Model of Spinal Cord Injury Demonstrating the Additive Effects of Rho and ROCK Inhibitors on Neurite Outgrowth and Myelination," Glia. 60(3): 441-56 (2012).
Cameron et al., "Bladder Management After Spinal Cord Injury in the United States 1972 to 2005," J Urol. 184(1): 213-7 (2010).
Campagnolo et al., Acute medical and surgical management of spinal cord injury. Spinal Cord Medicine, Philadelphia: Lippincott, Williams & Wilkins 96-107 (2002).
Cardenas et al., "Urinary Tract Infection in Persons With Spinal Cord Injury," Arch Phys Med Rehabil. 76(3): 272-80 (1995).
Chua et al., "The Effect of Umbilical Cord Blood Cells on Outcomes After Experimental Traumatic Spinal Cord Injury," Spine. 35(16): 1520-6 (2010).

(Continued)

*Primary Examiner* — Julie Ha
*Assistant Examiner* — Tara L Martinez
(74) *Attorney, Agent, or Firm* — Clark & Elbing LLP

(57) ABSTRACT

The present invention provides, among other things, improved therapeutic compositions comprising a C3 fusion protein and methods of making and using the same. In particular, the present invention provides improved methods for the treatment of spinal cord injury and other CNS trauma and/or facilitate axon growth or other tissue repair.

9 Claims, 11 Drawing Sheets
Specification includes a Sequence Listing.

(56) References Cited

OTHER PUBLICATIONS

Clark et al., "Genomic Analysis of Metastasis Reveals an Essential Role for RhoC," Nature. 406(6795): 532-5 (2000).
Cormier et al., "Development of Autonomic Dysreflexia After Spinal Cord Injury Is Associated With a Lack of Serotonergic Axons in the Intermediolateral Cell Column," J Neurotrauma. 27(10): 1805-18 (2010).
Cruz-Almeida et al., "Chronicity of Pain Associated With Spinal Cord Injury: A Longitudinal Analysis," J Rehabil Res Dev. 42(5): 585-94 (2005).
Demjen et al., "Neutralization of CD95 Ligand Promotes Regeneration and Functional Recovery After Spinal Cord Injury," Nat Med. 10(4): 389-95 (2004).
Deng et al., "Lithium Chloride Combined With Human Umbilical Cord Blood Mesenchymal Stem Cell Transplantation for Treatment of Spinal Cord Injury in Rats," J Southern Med. 30(11): 2436-9 (Translated abstract) (2010).
Dergham et al., "Rho Signaling Pathway Targeted to Promote Spinal Cord Repair," J Neurosci. 22(15): 6570-7 (2002).
Dubreuil et al., "Rho Activation Patterns After Spinal Cord Injury and the Role of Activated Rho in Apoptosis in the Central Nervous System," J Cell Biol. 162(2): 233-43 (2003).
Dubreuil et al., "Activation of Rho After Traumatic Brain Injury and Seizure in Rats," Exp Neurol. 198(2): 361-9 (2006).
Fehlings et al., "A Phase I/IIa Clinical Trial of a Recombinant Rho Protein Antagonist in Acute Spinal Cord Injury," J Neurotrauma. 28(5): 787-96 (2011).
Fouad et al., "Transplantation and Repair: Combined Cell Implantation and Chondroitinase Delivery Prevents Deterioration of Bladder Function in Rats With Complete Spinal Cord Injury," Spinal Cord. 47(10): 727-32 (2009).
Fournier et al., "Rho Kinase Inhibition Enhances Axonal Regeneration in the Injured CNS," J Neurosci 23(4): 1416-23 (2003).
Furuya et al., "Treatment of Rat Spinal Cord Injury With a Rho-kinase Inhibitor and Bone Marrow Stromal Cell Transplantation," Brain Res. 1295: 192-202 (2009).
Gensel et al., "Spinal Cord Injury Therapies in Humans: An Overview of Current Clinical Trials and Their Potential Effects on Intrinsic CNS Macrophages," Expert Opin Ther Targets. 15(4): 505-18 (2011).
Gonzalez et al., "Reducing Inflammation Decreases Secondary Degeneration and Functional Deficit After Spinal Cord Injury," Exp Neurol 184(1): 456-63 (2003).
Gris et al., "Transient Blockade of the CD11d/CD18 Integrin Reduces Secondary Damage After Spinal Cord Injury, Improving Sensory, Autonomic, and Motor Function," J Neurosci. 24(16): 4043-51 (2004).
Hayes et al., "Elevated Serum Titers of Proinflammatory Cytokines and CNS Autoantibodies in Patients With Chronic Spinal Cord Injury," J Neurotrauma. 19(6): 753-61 (2002).
He et al., "Differential Gene Expression Profiling of CD34+ CD133+ Umbilical Cord Blood Hematopoietic Stem Progenitor Cells," Stem Cells Dev. 14(2): 188-98 (2005).
Huang et al., "A Novel Lysophospholipid- And pH-sensitive Receptor, GPR4, in Brain Endothelial Cells Regulates Monocyte Transmigration," Endothelium. 14(1): 25-34 (2007).
Hayashi et al., "Sequential mRNA Expression for Immediate Early Genes, Cytokines, and Neurotrophins in Spinal Cord Injury," J Neurotrauma. 17(3): 203-18 (2000).
Inoue et al., "Initiation of Neuropathic Pain Requires Lysophosphatidic Acid Receptor Signaling," Nat Med. 10(7): 712-8 (2004).
Jaffe et al., "Rho GTPases in Transformation and Metastasis," Adv Cancer Res. 84: 57-80 (2002).
Krassioukov et al., "Autonomic Dysreflexia in Acute Spinal Cord Injury: An Under-Recognized Clinical Entity," J Neurotrauma. 20(8): 707-16 (2003).
Kaner et al., "The Effects of Human Umbilical Cord Blood Transplantation in Rats With Experimentally Induced Spinal Cord Injury," J Neurosurg Spine 13(4): 543-51 (2010).
Koyanagi et al., "Inhibition of the Rho/ROCK Pathway Reduces Apoptosis During Transplantation of Embryonic Stem Cell-Derived Neural Precursors," J Neurosci Res. 86(2): 270-80 (2008).
Lee et al., "Schwann Cell-Like Remyelination Following Transplantation of Human Umbilical Cord Blood (hUCB)-derived Mesenchymal Stem Cells in Dogs With Acute Spinal Cord Injury," J Neurol Sci. 300(1-2): 86-96 (2011).
Levendoglu et al., "Gabapentin Is a First Line Drug for the Treatment of Neuropathic Pain in Spinal Cord Injury," Spine 29(7): 743-51 (2004).
Lim et al., "Transplantation of Canine Umbilical Cord Blood-Derived Mesenchymal Stem Cells in Experimentally Induced Spinal Cord Injured Dogs," J Vet Sci. 8(3): 275-82 (2007).
Linsenmeyer, Neurogenic bladder following spinal cord injury. Spinal Cord Medicine, Philadelphia: Lippincoat, Williams & Wilkins 181-206 (2002).
Linsenmeyer, Update on bladder evaluation recommendations and bladder management guidline in patients with spinal cord injury, Current bladder dysfunction reports. 2:134-40 (2007).
Lord-Fontain et al., "Local inhibition of Rho Signaling by cell-permeable recombinant protein BA-210 prevents secondary damage and promotes functional recovery following acute spinal cord injury," J. Neurotrauma 25:1309-22 (2008).
Maksymowicz et al., "The perspectives of stem cell-based therapy in neurological disease," Stem Cells and Human Diseases. 26-60 (2012).
Neumann et al., "Tumor necrosis factor inhibits neurite outgrowth and branching of hippocampal neurons by a pho-dependent mechanism," J. Neurosci. 22(3): 854-62 (2002).
Paik et al., "Sphingosine 1-Phosphate-induced endothelial cell migration requires the expression of EDG-1 and EDG-3 receptors and rho-dependent activation of $\alpha v\beta$- and $\beta 1$-containing integrins," J. Biol. Chem. 276(15): 11830-7 (2001).
Park et al., "Comparison of canine umbilical cord blood-derived mesenchymal stem cell transplantation time: involvement of astrogliosis, inflammation, intracellular actin cytoskeleton pathways, and neurotrophin-3," Cell transplant. 20:1867-80 (2011).
Park et al., "Human umbilical cord blood-derived mesenchymal stem cell therapy promotes functional recovery of contused rat spinal cord through enhancement of endogenous cell proliferation and oligogenesis," J. Biomed. & Biotechnol. 2012: (2012) (8 pages).
Pearse et al., "cAMP and Schwann cells promote axonal growth and functional recovery after spinal cord injury," Nat Med. 10(6): 610-616 (2004).
Popovich et al., "Hematogenous macrophages express CD8 and distribute to regions of lesion cavitation after spinal cord injury," Exp. Neurol. 182(2): 275-287 (2003).
Ramer et al., "Rho-kinase inhibition enhances axonal plasticity and attenuates cold hyperalgesia after dorsal rhizotomy," J Neurosci. 24(48):10796-10805 (2004).
Schira et al., "Significant clinical, neuropathological and behavioral recovery from acute spinal cord trauma by transplantation of a well-defined somatic stem cell from human umbilical cord blood," Brain. 135(2): 431-446 (2012).
Siddall et al., "Pain report and the relationship of pain to physical factors in the first 6 months following spinal cord injury," Pain. 81 (1-2): 187-197 (1999).
Siddall et al., "A longitudinal study of the prevalence and characteristics of pain in the first 5 years following spinal cord injury," Pain. 103(3): 249-257 (2003).
Sung et al., "A possible role of RhoA/Rho-kinase in experimental spinal cord injury in rat," 959(1): 29-38 (2003).
Tigyi et al., "Lysophosphatidic acid-induced neurite retraction in PC12 cells: neurite-protective effects of cyclic AMP signaling," J Neurochem. 66(2): 549-558 (1996).
Watanabe et al., "A ROCK inhibitor permits survival of dissociated human embryonic stem cells," Nat Biotechnol. 25(6): 681-686 (2007).
Weaver et al., "Central mechanisms for autonomic dysreflexia after spinal cord injury," Prog Brain Res. 137: 83-95 (2002).

(56) References Cited

OTHER PUBLICATIONS

Wong et al., "A three-month, open-label, single-arm trial evaluating the safety and pharmacokinetics of oral lithium in patients with chronic spinal cord injury," Spinal Cord. 49(1): 94-98 (2011).
Woodcock et al., "Development of novel combination therapies," N Engl J Med. 364(11): 985-987 (2011).
Yang et al., "Efficacy and safety of lithium carbonate treatment of chronic spinal cord injuries: a double-blind, randomized, placebo-controlled clinical trial," Spinal Cord. 50(2): 141-146 (2012).
Yick et al., "Lithium chloride reinforces the regeneration-promoting effect of chondroitinase ABC on rubrospinal neurons after spinal cord injury," J Neurotrauma, 21 (7): 932-943 (2004).
Young, "Review of lithium effects on brain and blood," Cell Trans. 18(9): 951-975 (2009).

\* cited by examiner

| SUBSTANCE | A | B | C | D | X | 1.05 |
|---|---|---|---|---|---|---|
| PROCESS 1 | 4.3 | 3.1 | 1.9 | 7.9 | 77.0 | 1.4 |
| PROCESS 2 | 4.5 | 5.7 | 3.3 | 17.2 | 60.8 | 2.0 |

1. C3 FUSION PROTEIN+FIBRINOGEN SOLUTION

2. THROMBIN SOLUTION

3. DUPLOJECT SYRINGE

1. FIBRINOGEN SOLUTION

2. C3 FUSION PROTEIN+THROMBIN SOLUTION

3. DUPLOJECT SYRINGE

SEQUENCE LISTING

```
<160> NUMBER OF SEQ ID NOS: 28

<210> SEQ ID NO 1
<211> LENGTH: 231
<212> TYPE: PRT
<213> ORGANISM: Artificial Sequence
<220> FEATURE:
<223> OTHER INFORMATION: Synthetic polypeptide

<400> SEQUENCE: 1

Ser Ala Tyr Ser Asn Thr Tyr Gln Glu Phe Thr Asn Ile Asp Gln Ala
1               5                   10                  15

Lys Ala Trp Gly Asn Ala Gln Tyr Lys Lys Tyr Gly Leu Ser Lys Ser
            20                  25                  30

Glu Lys Glu Ala Ile Val Ser Tyr Thr Lys Ser Ala Ser Glu Ile Asn
```

```
                35                  40                  45
Gly Lys Leu Arg Gln Asn Lys Gly Val Ile Asn Gly Phe Pro Ser Asn
 50                  55                  60

Leu Ile Lys Gln Val Glu Leu Leu Asp Lys Ser Phe Asn Lys Met Lys
 65                  70                  75                  80

Thr Pro Glu Asn Ile Met Leu Phe Arg Gly Asp Pro Ala Tyr Leu
                 85                  90                  95

Gly Thr Glu Phe Gln Asn Thr Leu Leu Asn Ser Asn Gly Thr Ile Asn
                100                 105                 110

Lys Thr Ala Phe Glu Lys Ala Lys Ala Lys Phe Leu Asn Lys Asp Arg
                115                 120                 125

Leu Glu Tyr Gly Tyr Ile Ser Thr Ser Leu Met Asn Val Ser Gln Phe
130                 135                 140

Ala Gly Arg Pro Ile Ile Thr Lys Phe Lys Val Ala Lys Gly Ser Lys
145                 150                 155                 160

Ala Gly Tyr Ile Asp Pro Ile Ser Ala Phe Ala Gly Gln Leu Glu Met
                165                 170                 175

Leu Leu Pro Arg His Ser Thr Tyr His Ile Asp Asp Met Arg Leu Ser
                180                 185                 190

Ser Asp Gly Lys Gln Ile Ile Ile Thr Ala Thr Met Met Gly Thr Ala
                195                 200                 205

Ile Asn Pro Lys Glu Phe Val Met Asn Pro Ala Asn Ala Gln Gly Arg
210                 215                 220

His Thr Pro Gly Thr Arg Leu
225                 230

<210> SEQ ID NO 2
<211> LENGTH: 232
<212> TYPE: PRT
<213> ORGANISM: Artificial Sequence
<220> FEATURE:
<223> OTHER INFORMATION: Synthetic polypeptide

<400> SEQUENCE: 2

Met Ser Ala Tyr Ser Asn Thr Tyr Gln Glu Phe Thr Asn Ile Asp Gln
 1               5                  10                  15

Ala Lys Ala Trp Gly Asn Ala Gln Tyr Lys Lys Tyr Gly Leu Ser Lys
                 20                  25                  30

Ser Glu Lys Glu Ala Ile Val Ser Tyr Thr Lys Ser Ala Ser Glu Ile
                 35                  40                  45

Asn Gly Lys Leu Arg Gln Asn Lys Gly Val Ile Asn Gly Phe Pro Ser
 50                  55                  60

Asn Leu Ile Lys Gln Val Glu Leu Leu Asp Lys Ser Phe Asn Lys Met
 65                  70                  75                  80

Lys Thr Pro Glu Asn Ile Met Leu Phe Arg Gly Asp Pro Ala Tyr
                 85                  90                  95

Leu Gly Thr Glu Phe Gln Asn Thr Leu Leu Asn Ser Asn Gly Thr Ile
                100                 105                 110

Asn Lys Thr Ala Phe Glu Lys Ala Lys Ala Lys Phe Leu Asn Lys Asp
                115                 120                 125

Arg Leu Glu Tyr Gly Tyr Ile Ser Thr Ser Leu Met Asn Val Ser Gln
                130                 135                 140

Phe Ala Gly Arg Pro Ile Ile Thr Lys Phe Lys Val Ala Lys Gly Ser
145                 150                 155                 160

Lys Ala Gly Tyr Ile Asp Pro Ile Ser Ala Phe Ala Gly Gln Leu Glu
```

```
                165                 170                 175
Met Leu Leu Pro Arg His Ser Thr Tyr His Ile Asp Asp Met Arg Leu
            180                 185                 190

Ser Ser Asp Gly Lys Gln Ile Ile Ile Thr Ala Thr Met Met Gly Thr
        195                 200                 205

Ala Ile Asn Pro Lys Glu Phe Val Met Asn Pro Ala Asn Ala Gln Gly
    210                 215                 220

Arg His Thr Pro Gly Thr Arg Leu
225                 230

<210> SEQ ID NO 3
<211> LENGTH: 699
<212> TYPE: DNA
<213> ORGANISM: Artificial Sequence
<220> FEATURE:
<223> OTHER INFORMATION: Synthetic polynucleotide

<400> SEQUENCE: 3
atgtcggctt attcaaatac ttaccaggag tttactaata ttgatcaagc aaaagcttgg      60
ggtaatgctc agtataaaaa gtatggacta agcaaatcag aaaaagaagc tatagtatca    120
tatactaaaa gcgctagtga ataaatggaa agctaagac aaaataaggg agttatcaat     180
ggatttcctt caaatttaat aaaacaagtt gaacttttag ataaatcttt taataaaatg    240
aagacccctg aaaatattat gttatttaga ggcgacgacc ctgcttattt aggaacagaa    300
tttcaaaaca ctcttcttaa ttcaaatggt acaattaata aaacggcttt tgaaaaggct    360
aaagctaagt ttttaaataa agatagactt gaatatggat atattagtac ttcattaatg    420
aatgtttctc aatttgcagg aagaccaatt attacaaaat ttaaagtagc aaaaggctca    480
aaggcaggat atattgaccc tattagtgct tttgcaggac aacttgaaat gttgcttcct    540
agacatagta cttatcatat agacgatatg agattgtctt ctgatggtaa acaaataata    600
attacagcaa caatgatggg cacagctatc aatcctaaag aattcgtgat gaatcccgca    660
aacgcgcaag gcagacatac acccggtacc agactctag                            699

<210> SEQ ID NO 4
<211> LENGTH: 18
<212> TYPE: PRT
<213> ORGANISM: Artificial Sequence
<220> FEATURE:
<223> OTHER INFORMATION: Synthetic peptide

<400> SEQUENCE: 4

Phe Val Met Asn Pro Ala Asn Ala Gln Gly Arg His Thr Pro Gly Thr
1               5                   10                  15

Arg Leu

<210> SEQ ID NO 5
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: /replace=" "
<220> FEATURE:
<221> NAME/KEY: MISC_FEATURE
<222> LOCATION: (1)..(11)
<223> OTHER INFORMATION: /note="Variant residues given in the sequence
      have no preference with respect to those in the annotations for
``` variant positions"

<400> SEQUENCE: 5

Met Ser Ala Tyr Ser Asn Thr Tyr Gln Glu Phe
1               5                   10

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: /replace=" "
<220> FEATURE:
<221> NAME/KEY: MISC_FEATURE
<222> LOCATION: (1)..(17)
<223> OTHER INFORMATION: /note="Variant residues given in the sequence
      have no preference with respect to those in the annotations for
      variant positions"

<400> SEQUENCE: 6

Met Ser Ala Tyr Ser Asn Thr Tyr Gln Glu Phe Thr Asn Ile Asp Gln
1               5                   10                  15

Ala

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide

<400> SEQUENCE: 7

Gln Gly Arg His Thr Pro Gly Thr Arg Leu
1               5                   10

<210> SEQ ID NO 8
<211> LENGTH: 224
<212> TYPE: PRT
<213> ORGANISM: Artificial Sequence
<220> FEATURE:
<223> OTHER INFORMATION: Synthetic polypeptide

<400> SEQUENCE: 8

Ser Ala Tyr Ser Asn Thr Tyr Gln Glu Phe Thr Asn Ile Asp Gln Ala
1               5                   10                  15

Lys Ala Trp Gly Asn Ala Gln Tyr Lys Lys Tyr Gly Leu Ser Lys Ser
            20                  25                  30

Glu Lys Glu Ala Ile Val Ser Tyr Thr Lys Ser Ala Ser Glu Ile Asn
        35                  40                  45

Gly Lys Leu Arg Gln Asn Lys Gly Val Ile Asn Gly Phe Pro Ser Asn
    50                  55                  60

Leu Ile Lys Gln Val Glu Leu Leu Asp Lys Ser Phe Asn Lys Met Lys
65                  70                  75                  80

Thr Pro Glu Asn Ile Met Leu Phe Arg Gly Asp Asp Pro Ala Tyr Leu
                85                  90                  95

Gly Thr Glu Phe Gln Asn Thr Leu Leu Asn Ser Asn Gly Thr Ile Asn
            100                 105                 110

Lys Thr Ala Phe Glu Lys Ala Lys Ala Lys Phe Leu Asn Lys Asp Arg
        115                 120                 125

Leu Glu Tyr Gly Tyr Ile Ser Thr Ser Leu Met Asn Val Ser Gln Phe
130                 135                 140

Ala Gly Arg Pro Ile Ile Thr Lys Phe Lys Val Ala Lys Gly Ser Lys
145                 150                 155                 160

Ala Gly Tyr Ile Asp Pro Ile Ser Ala Phe Ala Gly Gln Leu Glu Met
                165                 170                 175

Leu Leu Pro Arg His Ser Thr Tyr His Ile Asp Asp Met Arg Leu Ser
                180                 185                 190

Ser Asp Gly Lys Gln Ile Ile Ile Thr Ala Thr Met Met Gly Thr Ala
            195                 200                 205

Ile Asn Pro Lys Glu Phe Val Met Asn Pro Ala Asn Ala Gln Gly Arg
210                 215                 220

<210> SEQ ID NO 9
<211> LENGTH: 225
<212> TYPE: PRT
<213> ORGANISM: Artificial Sequence
<220> FEATURE:
<223> OTHER INFORMATION: Synthetic polypeptide

<400> SEQUENCE: 9

Met Ser Ala Tyr Ser Asn Thr Tyr Gln Glu Phe Thr Asn Ile Asp Gln
1               5                   10                  15

Ala Lys Ala Trp Gly Asn Ala Gln Tyr Lys Lys Tyr Gly Leu Ser Lys
                20                  25                  30

Ser Glu Lys Glu Ala Ile Val Ser Tyr Thr Lys Ser Ala Ser Glu Ile
            35                  40                  45

Asn Gly Lys Leu Arg Gln Asn Lys Gly Val Ile Asn Gly Phe Pro Ser
50                  55                  60

Asn Leu Ile Lys Gln Val Glu Leu Leu Asp Lys Ser Phe Asn Lys Met
65                  70                  75                  80

Lys Thr Pro Glu Asn Ile Met Leu Phe Arg Gly Asp Pro Ala Tyr
                85                  90                  95

Leu Gly Thr Glu Phe Gln Asn Thr Leu Leu Asn Ser Asn Gly Thr Ile
                100                 105                 110

Asn Lys Thr Ala Phe Glu Lys Ala Lys Ala Lys Phe Leu Asn Lys Asp
            115                 120                 125

Arg Leu Glu Tyr Gly Tyr Ile Ser Thr Ser Leu Met Asn Val Ser Gln
130                 135                 140

Phe Ala Gly Arg Pro Ile Ile Thr Lys Phe Lys Val Ala Lys Gly Ser
145                 150                 155                 160

Lys Ala Gly Tyr Ile Asp Pro Ile Ser Ala Phe Ala Gly Gln Leu Glu
                165                 170                 175

Met Leu Leu Pro Arg His Ser Thr Tyr His Ile Asp Asp Met Arg Leu
                180                 185                 190

Ser Ser Asp Gly Lys Gln Ile Ile Ile Thr Ala Thr Met Met Gly Thr
            195                 200                 205

Ala Ile Asn Pro Lys Glu Phe Val Met Asn Pro Ala Asn Ala Gln Gly
210                 215                 220

Arg
225

<210> SEQ ID NO 10
<211> LENGTH: 19
<212> TYPE: PRT
<213> ORGANISM: Unknown
<220> FEATURE:

<223> OTHER INFORMATION: Transport domain

<400> SEQUENCE: 10

Glu Phe Val Met Asn Pro Ala Asn Ala Gln Gly Arg His Thr Pro Gly
1               5                   10                  15
Thr Arg Leu

<210> SEQ ID NO 11
<211> LENGTH: 12
<212> TYPE: PRT
<213> ORGANISM: Unknown
<220> FEATURE:
<223> OTHER INFORMATION: Transport domain

<400> SEQUENCE: 11

Glu Phe Val Met Asn Pro Ala Asn Ala Gln Gly Arg
1               5                   10

<210> SEQ ID NO 12
<211> LENGTH: 251
<212> TYPE: PRT
<213> ORGANISM: Clostridium botulinum

<400> SEQUENCE: 12

Met Lys Gly Leu Arg Lys Ser Ile Leu Cys Leu Val Leu Ser Ala Gly
1               5                   10                  15

Val Ile Ala Pro Val Thr Ser Gly Met Ile Gln Ser Pro Gln Lys Cys
                20                  25                  30

Tyr Ala Tyr Ser Ile Asn Gln Lys Ala Tyr Ser Asn Thr Tyr Gln Glu
            35                  40                  45

Phe Thr Asn Ile Asp Gln Ala Lys Ala Trp Gly Asn Ala Gln Tyr Lys
        50                  55                  60

Lys Tyr Gly Leu Ser Lys Ser Glu Lys Glu Ala Ile Val Ser Tyr Thr
65                  70                  75                  80

Lys Ser Ala Ser Glu Ile Asn Gly Lys Leu Arg Gln Asn Lys Gly Val
                85                  90                  95

Ile Asn Gly Phe Pro Ser Asn Leu Ile Lys Gln Val Glu Leu Leu Asp
            100                 105                 110

Lys Ser Phe Asn Lys Met Lys Thr Pro Glu Asn Ile Met Leu Phe Arg
        115                 120                 125

Gly Asp Asp Pro Ala Tyr Leu Gly Thr Glu Phe Gln Asn Thr Leu Leu
130                 135                 140

Asn Ser Asn Gly Thr Ile Asn Lys Thr Ala Phe Glu Lys Ala Lys Ala
145                 150                 155                 160

Lys Phe Leu Asn Lys Asp Arg Leu Glu Tyr Gly Tyr Ile Ser Thr Ser
                165                 170                 175

Leu Met Asn Val Ser Gln Phe Ala Gly Arg Pro Ile Ile Thr Lys Phe
            180                 185                 190

Lys Val Ala Lys Gly Ser Lys Ala Gly Tyr Ile Asp Pro Ile Ser Ala
        195                 200                 205

Phe Ala Gly Gln Leu Glu Met Leu Leu Pro Arg His Ser Thr Tyr His
210                 215                 220

Ile Asp Asp Met Arg Leu Ser Ser Asp Gly Lys Gln Ile Ile Ile Thr
225                 230                 235                 240

Ala Thr Met Met Gly Thr Ala Ile Asn Pro Lys
                245                 250

```
<210> SEQ ID NO 13
<211> LENGTH: 212
<212> TYPE: PRT
<213> ORGANISM: Clostridium botulinum

<400> SEQUENCE: 13

Ser Ala Tyr Ser Asn Thr Tyr Gln Glu Phe Thr Asn Ile Asp Gln Ala
1               5                   10                  15

Lys Ala Trp Gly Asn Ala Gln Tyr Lys Lys Tyr Gly Leu Ser Lys Ser
            20                  25                  30

Glu Lys Glu Ala Ile Val Ser Tyr Thr Lys Ser Ala Ser Glu Ile Asn
        35                  40                  45

Gly Lys Leu Arg Gln Asn Lys Gly Val Ile Asn Gly Phe Pro Ser Asn
    50                  55                  60

Leu Ile Lys Gln Val Glu Leu Leu Asp Lys Ser Phe Asn Lys Met Lys
65                  70                  75                  80

Thr Pro Glu Asn Ile Met Leu Phe Arg Gly Asp Asp Pro Ala Tyr Leu
                85                  90                  95

Gly Thr Glu Phe Gln Asn Thr Leu Leu Asn Ser Asn Gly Thr Ile Asn
            100                 105                 110

Lys Thr Ala Phe Glu Lys Ala Lys Ala Lys Phe Leu Asn Lys Asp Arg
        115                 120                 125

Leu Glu Tyr Gly Tyr Ile Ser Thr Ser Leu Met Asn Val Ser Gln Phe
    130                 135                 140

Ala Gly Arg Pro Ile Ile Thr Lys Phe Lys Val Ala Lys Gly Ser Lys
145                 150                 155                 160

Ala Gly Tyr Ile Asp Pro Ile Ser Ala Phe Ala Gly Gln Leu Glu Met
                165                 170                 175

Leu Leu Pro Arg His Ser Thr Tyr His Ile Asp Asp Met Arg Leu Ser
            180                 185                 190

Ser Asp Gly Lys Gln Ile Ile Ile Thr Ala Thr Met Met Gly Thr Ala
        195                 200                 205

Ile Asn Pro Lys
    210

<210> SEQ ID NO 14
<211> LENGTH: 213
<212> TYPE: PRT
<213> ORGANISM: Unknown
<220> FEATURE:
<223> OTHER INFORMATION: Active domain sequence

<400> SEQUENCE: 14

Met Ser Ala Tyr Ser Asn Thr Tyr Gln Glu Phe Thr Asn Ile Asp Gln
1               5                   10                  15

Ala Lys Ala Trp Gly Asn Ala Gln Tyr Lys Lys Tyr Gly Leu Ser Lys
            20                  25                  30

Ser Glu Lys Glu Ala Ile Val Ser Tyr Thr Lys Ser Ala Ser Glu Ile
        35                  40                  45

Asn Gly Lys Leu Arg Gln Asn Lys Gly Val Ile Asn Gly Phe Pro Ser
    50                  55                  60

Asn Leu Ile Lys Gln Val Glu Leu Leu Asp Lys Ser Phe Asn Lys Met
65                  70                  75                  80

Lys Thr Pro Glu Asn Ile Met Leu Phe Arg Gly Asp Asp Pro Ala Tyr
                85                  90                  95

Leu Gly Thr Glu Phe Gln Asn Thr Leu Leu Asn Ser Asn Gly Thr Ile
            100                 105                 110
```

```
Asn Lys Thr Ala Phe Glu Lys Ala Lys Phe Leu Asn Lys Asp
        115                 120                 125

Arg Leu Glu Tyr Gly Tyr Ile Ser Thr Ser Leu Met Asn Val Ser Gln
130                 135                 140

Phe Ala Gly Arg Pro Ile Ile Thr Lys Phe Lys Val Ala Lys Gly Ser
145                 150                 155                 160

Lys Ala Gly Tyr Ile Asp Pro Ile Ser Ala Phe Ala Gly Gln Leu Glu
                165                 170                 175

Met Leu Leu Pro Arg His Ser Thr Tyr His Ile Asp Asp Met Arg Leu
                180                 185                 190

Ser Ser Asp Gly Lys Gln Ile Ile Ile Thr Ala Thr Met Met Gly Thr
                195                 200                 205

Ala Ile Asn Pro Lys
        210

<210> SEQ ID NO 15
<211> LENGTH: 17
<212> TYPE: PRT
<213> ORGANISM: Unknown
<220> FEATURE:
<223> OTHER INFORMATION: Antennapedia Leader Peptide

<400> SEQUENCE: 15

Lys Lys Trp Lys Met Arg Arg Asn Gln Phe Trp Val Lys Val Gln Arg
1               5                   10                  15

Gly

<210> SEQ ID NO 16
<211> LENGTH: 16
<212> TYPE: PRT
<213> ORGANISM: Drosophila sp.

<400> SEQUENCE: 16

Arg Gln Ile Lys Ile Trp Phe Gln Asn Arg Arg Met Lys Trp Lys Lys
1               5                   10                  15

<210> SEQ ID NO 17
<211> LENGTH: 13
<212> TYPE: PRT
<213> ORGANISM: Human immunodeficiency virus

<400> SEQUENCE: 17

Gly Arg Lys Lys Arg Arg Gln Arg Arg Pro Pro Gln
1               5                   10

<210> SEQ ID NO 18
<211> LENGTH: 11
<212> TYPE: PRT
<213> ORGANISM: Human immunodeficiency virus

<400> SEQUENCE: 18

Tyr Gly Arg Lys Lys Arg Arg Gln Arg Arg Arg
1               5                   10

<210> SEQ ID NO 19
<211> LENGTH: 10
<212> TYPE: PRT
<213> ORGANISM: Human immunodeficiency virus

<400> SEQUENCE: 19

Gly Arg Lys Lys Arg Arg Gln Arg Arg Arg
```

```
<210> SEQ ID NO 20
<211> LENGTH: 31
<212> TYPE: PRT
<213> ORGANISM: Artificial Sequence
<220> FEATURE:
<223> OTHER INFORMATION: Synthetic polypeptide

<400> SEQUENCE: 20

Tyr Gly Arg Lys Lys Arg Arg Gln Arg Arg Gly Gly Thr Asn Val
1               5                   10                  15

Phe Asn Ala Thr Phe Glu Ile Trp His Asp Gly Glu Phe Gly Thr
            20                  25                  30

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide

<400> SEQUENCE: 21

Cys Gly Arg Lys Lys Arg Arg Gln Arg Arg
1               5                   10

<210> SEQ ID NO 22
<211> LENGTH: 20
<212> TYPE: PRT
<213> ORGANISM: Artificial Sequence
<220> FEATURE:
<223> OTHER INFORMATION: Synthetic peptide

<400> SEQUENCE: 22

Tyr Gly Arg Lys Lys Arg Arg Gln Arg Arg Ala Lys Glu Gly Ala
1               5                   10                  15

Asn Val Ala Gly
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic peptide

<400> SEQUENCE: 23

Tyr Gly Arg Lys Lys Arg Arg Gln Arg Arg Tyr Lys Glu Gly Tyr
1               5                   10                  15

Asn Val Tyr Gly
            20

<210> SEQ ID NO 24
<211> LENGTH: 30
<212> TYPE: PRT
<213> ORGANISM: Artificial Sequence
<220> FEATURE:
<223> OTHER INFORMATION: Synthetic polypeptide

<400> SEQUENCE: 24

Arg Arg Arg Gln Arg Arg Lys Lys Arg Gly Gly Asp Ile Met Gly
1               5                   10                  15

Trp Gly Asn Glu Ile Phe Gly Ala Ile Ala Gly Phe Leu Gly
            20                  25                  30
```

```
<210> SEQ ID NO 25
<211> LENGTH: 20
<212> TYPE: PRT
<213> ORGANISM: Artificial Sequence
<220> FEATURE:
<223> OTHER INFORMATION: Synthetic peptide

<400> SEQUENCE: 25

Tyr Gly Arg Lys Lys Arg Arg Gln Arg Arg Lys Leu Ser Ser Ile
1               5                   10                  15

Glu Ser Asp Val
            20

<210> SEQ ID NO 26
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 26

Tyr Gly Arg Lys Lys Arg Arg Gln Arg Arg Gly Gly Gly Leu Asp
1               5                   10                  15

Lys Glu Phe Asn Ser Ile Phe Arg Arg Ala Phe Ala Ser Arg Val Phe
            20                  25                  30

Pro Pro Glu
        35

<210> SEQ ID NO 27
<211> LENGTH: 36
<212> TYPE: PRT
<213> ORGANISM: Artificial Sequence
<220> FEATURE:
<223> OTHER INFORMATION: Synthetic polypeptid

<400> SEQUENCE: 27

Tyr Gly Arg Lys Lys Arg Arg Gln Arg Arg Arg Gly Gly Gly Leu Leu
1               5                   10                  15

Asp Tyr Val Pro Ile Gly Pro Arg Phe Ser Asn Leu Val Leu Gln Ala
            20                  25                  30

Leu Leu Val Leu
        35

<210> SEQ ID NO 28
<211> LENGTH: 35
<212> TYPE: PRT
<213> ORGANISM: Artificial Sequence
<220> FEATURE:
<223> OTHER INFORMATION: Synthetic polypeptide

<400> SEQUENCE: 28

Tyr Gly Arg Lys Lys Arg Arg Gln Arg Arg Gly Gly Gly Ile Pro
1               5                   10                  15

Pro Val Tyr Phe Ser Arg Leu Asp Leu Asn Leu Val Val Leu Leu Leu
            20                  25                  30

Ala Gln Leu
        35
```

C3 FUSION PROTEIN AND METHODS OF MAKING AND USING THEREOF

CROSS REFERENCE TO RELATED APPLICATIONS

This application claims priority to U.S. Provisional Application No. 62/512,661, filed May 30, 2017; U.S. Provisional Application No. 62/512,673, filed May 30, 2017; U.S. Provisional Application No. 62/512,695, filed May 30, 2017; U.S. Provisional Application No. 62/675,659, filed May 23, 2018; U.S. Provisional Application No. 62/675,680, filed May 23, 2018; and U.S. Provisional Application No. 62/675,714, filed May 23, 2018, each of which are hereby incorporated by reference in their entirety.

REFERENCE TO SEQUENCE LISTING

The instant application contains a Sequence Listing which has been submitted electronically in ASCII format and is hereby incorporated by reference in its entirety. The ASCII copy, created on Aug. 27, 2020 is named 51245-017007_Sequence_Listing_8_27_20_ST25 and is 21,899 bytes in size.

BACKGROUND

Spinal cord injury is damage to any part of the spinal cord or nerves at the end of the spinal canal and often causes permanent changes in strength, sensation and other body functions below the site of the injury. A patient's ability to control their limbs after spinal cord injury depends on two factors: the place of the injury along the spinal cord and the severity of injury to the spinal cord. Spinal cord injuries of any kind may result in one or more of the following signs and symptoms: loss of movement, loss of sensation, including the ability to feel heat, cold and touch, loss of bowel or bladder control, exaggerated reflex activities or spasms, changes in sexual function, sexual sensitivity and fertility, pain or an intense stinging sensation caused by damage to the nerve fibers in the spinal cord, and difficulty breathing, coughing or clearing secretions the lungs. Currently there is no approved treatment that reverses damage to the spinal cord.

ADP-ribosyl transferase C3 fusion proteins are being developed as therapy for spinal cord injury and other CNS trauma.

SUMMARY

The present invention provides improved methods and compositions for the effective treatment of spinal cord injury and other CNS trauma and/or for facilitating axon growth or other tissue repair based on an ADP-ribosyl transferase C3 fusion protein. Among other things, the invention provides improved processes for producing and purifying a composition comprising a C3 fusion protein, which is particularly robust, reproducible and results in increased yield, increased protein purity, and/or increased drug substance concentration. Thus, improved processes described herein allow more efficient manufacturing of a drug product based on an ADP-ribosyl transferase C3 fusion protein. Furthermore, the present invention provides an improved method of using a C3 fusion protein as a therapeutics for treating spinal cord injury and other CNS trauma. In particular, the present invention encompasses the surprising observation that combining a C3 fusion protein first with a fibrinogen composition without thrombin eliminates proteinase cleavage, providing a safer and more efficacious therapeutic composition for neurite outgrowth.

In one aspect, the present disclosure provides a pharmaceutical composition comprising a population of polypeptides, each having an amino acid sequence at least 85% (e.g., at least 90%, 92%, 94%, 95%, 96%, 97%, 98%, or 99%%) identical to SEQ ID NO:1, wherein the first amino acid of each polypeptide is not a methionine and wherein the population of the polypeptides constitutes greater than 85% (e.g., greater than 88%, 90%, 92%, 94%, 95%, 96%, 97%, 98%, or 99%) of the total amount of polypeptides in the composition.

In some embodiments, the pharmaceutical composition comprises a population of polypeptides, each having an amino acid sequence at least 85% (e.g., at least 90%, 92%, 94%, 95%, 96%, 97%, 98%, or 99%%) identical to SEQ ID NO:1, wherein the amino acid sequence is not SEQ ID NO:2 and wherein the population of the polypeptides constitutes greater than 85% (e.g., greater than 88%, 90%, 92%, 94%, 95%, 96%, 97%, 98%, or 99%) of the total amount of polypeptides in the composition.

In some embodiments, the population of the polypeptides constitutes greater than 90% of the total amount of polypeptides in the composition.

In some embodiments, the population of the polypeptides constitutes greater than 95% of the total amount of polypeptides in the composition.

In some embodiments, the population of the polypeptides constitutes greater than 98% of the total amount of polypeptides in the composition.

In some embodiments, the population of the polypeptides constitutes greater than 99% of the total amount of polypeptides in the composition.

In some embodiments, the composition is substantially free of other polypeptides.

In some embodiments, the amount of the polypeptides in the composition is determined scanning densitometry or image analysis.

In some embodiments, the amino acid sequence is at least 90% identical to SEQ ID NO:1. In some embodiments, the amino acid sequence is at least 95% identical to SEQ ID NO:1. In some embodiments, the amino acid sequence is identical to SEQ ID NO:1.

In some embodiments, each polypeptide has 213-231 amino acids in total. In some embodiments, each polypeptide has 231 amino acids in total.

In one aspect, the present disclosure provides a pharmaceutical composition comprising: a first polypeptide and a second polypeptide, wherein the first polypeptide comprises an amino acid sequence at least 85% (e.g., at least 90%, 92%, 94%, 95%, 96%, 97%, 98%, or 99%%) identical to SEQ ID NO:1 but does not contain a methionine at the N-terminus, the second polypeptide is otherwise identical to the first polypeptide but contains a methionine at the N-terminus, and the weight ratio of the first polypeptide to the second polypeptide is at least 6:1.

In some embodiments, the weight ratio of the first polypeptide to the second polypeptide is at least 7:1, 8:1, 9:1, 10:1, 12:1, 15:1, 20:1, 50:1, or 100:1.

In some embodiments, the amino acid sequence is at least 90%, 95%, 96%, 97%, 98%, or 99% identical to SEQ ID NO:1.

In some embodiments, the amino acid sequence is identical to SEQ ID NO:1.

In one aspect, the present disclosure provides a pharmaceutical composition comprising a polypeptide having an amino acid sequence at least 85% (e.g., at least 90%, 92%, 94%, 95%, 96%, 97%, 98%, or 99%%) identical to SEQ ID NO:1, wherein the polypeptide does not contain a methionine at the N-terminus, and wherein the polypeptide is present at a concentration ranging from 1.0 mg/mL-40 mg/mL, as determined by UV spectrometry at 280 nm.

In some embodiments, the concentration of the polypeptide is in a range of about 5.0 mg/mL-40 mg/mL, as determined by UV spectrometry at 280 nm. In some embodiments, the concentration of the polypeptide is in a range of about 8.0 mg/mL-20 mg/mL, as determined by UV spectrometry at 280 nm. In some embodiments, the concentration of the polypeptide is in a range of about 10 mg/mL-15 mg/mL, as determined by UV spectrometry at 280 nm.

In some embodiments, the concentration of the polypeptide is in a range of about 9.0 mg/mL-11 mg/mL, as determined by UV spectrometry at 280 nm. In some embodiments, the concentration of the polypeptide is in a range of about 27.0 mg/mL-33 mg/mL, as determined by UV spectrometry at 280 nm.

In one aspect, the present disclosure provides a pharmaceutical composition comprising a polypeptide having an amino acid sequence at least 85% (e.g., at least 90%, 92%, 94%, 95%, 96%, 97%, 98%, or 99%%) identical to SEQ ID NO:1, wherein the polypeptide does not contain a methionine at the N-terminus, and wherein the composition contains less than 100 ng/mg host cell protein (HCP).

In some embodiments, the composition contains less than 90 ng/mg, less than 80 ng/mg, less than 70 ng/mg, less than 60 ng/mg, less than 50 ng/mg, less than 40 ng/mg, less than 30 ng/mg, less than 20 ng/mg, less than 10 ng/mg, or less than 10 ng/mg, or below the limit of detection of host cell protein (HCP).

In one aspect, the present disclosure provides a pharmaceutical composition comprising a polypeptide having an amino acid sequence at least 85% (e.g., at least 90%, 92%, 94%, 95%, 96%, 97%, 98%, or 99%%) identical to SEQ ID NO:1, wherein the polypeptide does not contain a methionine at the N-terminus, and wherein the composition contains less than $2.9 \times 10^{-4}$ EU/mg Endotoxin.

In one aspect, the present disclosure provides a pharmaceutical composition comprising a polypeptide having an amino acid sequence at least 85% (e.g., at least 90%, 92%, 94%, 95%, 96%, 97%, 98%, or 99%%) identical to SEQ ID NO:1, wherein the polypeptide does not contain a methionine at the N-terminus, and wherein the pharmaceutical composition comprises a buffer and has a pH ranging from 5.5-7.5 at 25° C.

In some embodiments, the buffer is a citrate buffer.

In various embodiments, a composition described herein has a purity of equal to or greater than 80% measured by main peak of IE-HPLC. In various embodiments, the purity is equal to or greater than 83% measured by the main peak of IE-HPLC. In various embodiments, the purity is equal to or greater than 85% measured by the main peak of IE-HPLC. In various embodiments, the purity is equal to or greater than 90% measured by the main peak of IE-HPLC.

In some embodiments, a composition described herein contains less than or equal to 15% total acidic peaks measured by IE-HPLC. In some embodiments, a composition described herein contains less than or equal to 10% total acidic peaks measured by IE-HPLC.

In some embodiments, a composition described herein contains less than or equal to 5% total basic peaks measured by IE-HPLC.

In one aspect, the present disclosure provides a pharmaceutical composition comprising a purified recombinant C3 fusion protein having an amino acid sequence at least 85% (e.g., at least 90%, 92%, 94%, 95%, 96%, 97%, 98%, or 99%%) identical to SEQ ID NO:1, wherein the purified recombinant C3 fusion protein has a purity of equal to or greater than 80% measured by main peak of IE-HPLC. In some embodiments, the purity is equal to or greater than 83% measured by the main peak of IE-HPLC. In some embodiments, the purity is equal to or greater than 85% measured by the main peak of IE-HPLC. In some embodiments, the purity is equal to or greater than 90% measured by the main peak of IE-HPLC.

In some embodiments, the composition contains less than or equal to 10% total acidic peaks measured by IE-HPLC. In some embodiments, the composition contains less than or equal to 15% total acidic peaks measured by IE-HPLC.

In some embodiments, the composition contains less than or equal to 5% total basic peaks measured by IE-HPLC.

In some embodiments, the purified recombinant C3 fusion protein does not have a methionine at the N-terminus.

In some embodiments, the pharmaceutical composition is substantially free of polypeptides comprising methionine as the first amino acid.

In some embodiments, a composition described herein further comprises fibrinogen and does not contain thrombin.

In some embodiments, a composition described herein further comprises albumin, one or more blood coagulation factors, globulin, and/or one or more plasminogen-activator inhibitors or plasmin inhibitors.

In some embodiments, the one or more plasminogen-activator inhibitors or plasmin inhibitors comprise aprotinin.

In some embodiments, a composition described herein further comprises thrombin. In some embodiments, a composition further comprises a tissue adhesive.

In one aspect, the present invention provides a method for producing recombinant ADP-ribosyl transferase C3 (C3 fusion protein), comprising: cultivating host cells comprising a nucleic acid encoding a recombinant C3 fusion protein having an amino acid sequence of SEQ ID NO:2 in a large scale vessel under conditions that promote expression of the C3 fusion protein at a titer concentration of or greater than 1 g/L (e.g., of or greater than 1.5 g/L, 2 g/L, 2.5 g/L, 3 g/L, 3.5 g/L, 4 g/L, 4.5 g/L, or 5 g/L).

In some embodiments, the conditions for cultivating cells involve a fermentation process.

In one aspect, the present invention provides a method for producing recombinant ADP-ribosyl transferase C3 (C3 fusion protein), comprising: cultivating host cells comprising a nucleic acid encoding a recombinant C3 fusion protein having an amino acid sequence of SEQ ID NO:2 in a large scale vessel under conditions that involve a fermentation process to promote expression of the C3 fusion protein.

In some embodiments, the fermentation process is a fed batch culturing process. In some embodiments, the fed batch culturing process includes a batch mode, a first stage of exponential feeding, and a second stage of constant feeding. In some embodiments, the carbon source is selected from glycerol, glucose, sucrose, lactose, arabinose, maltotriose, sorbitol, xylose, rhamnose, and/or mannose.

In some embodiments, the batch mode lasts for at least about 7-8 hours, the first stage of exponential feeding lasts for about 7-13 hours, the second stage of constant feeding lasts for about 1-9 hours.

In some embodiments, the batch mode lasts for at least about 7 hours, the first stage of exponential feeding lasts for about 7-8 hours and the second stage of constant feeding lasts for about 8 hours.

In some embodiments, the second stage of constant feeding is at a feed rate at the end of the exponential feeding stage.

In some embodiments, the method further comprises a third stage of constant feeding. In some embodiments, the feed rate at the third stage of constant feeding is the same as the second stage. In some embodiments, the third stage of constant feeding lasts for at least about 4 hours.

In some embodiments, the first exponential feeding stage is maintained at a temperature between 34° C. to 40° C., and the second and/or third constant feeding stage is maintained at a temperature between 24° C. to 32° C.

In some embodiments, the first exponential feeding stage is maintained at 37±2° C. In some embodiments, the second and/or third constant feeding stage is maintained at 28±2° C.

In some embodiments, the method comprises a step of adding an inducing agent to trigger expression of the C3 fusion protein. In some embodiments, the inducing agent is Isopropyl β-D-1-thiogalactopyranoside (IPTG). In some embodiments, the IPTG is added at a concentration range of 0.1 mM-10 mM. In some embodiments, wherein the IPTG is added at a concentration of 5 mM.

In some embodiments, the carbon source at the first stage is a first sugar and the carbon source at the second stage is a second sugar. In certain embodiments, the first sugar and second sugar are different sugars.

In some embodiments, the first sugar is selected from the group consisting of glycerol, glucose, sucrose, and any combination thereof and the second sugar is selected from the group consisting of glycerol, glucose, sucrose, and any combination thereof. In some embodiments, the first sugar and second sugar are identical sugars. In some embodiments, the identical sugars comprise glycerol.

In some embodiments, the large scale vessel is a bioreactor.

In some embodiments, the host cells are bacterial cells. In some embodiments the bacterial cells are *E. coli*.

In some embodiments, the method further comprises a step of recovering the expressed C3 fusion protein from the host cells. In some embodiments, the method further comprises purifying the expressed recombinant C3 fusion protein.

In some embodiments, the at least 80%, 85%, 90%, or 95% of the purified recombinant C3 fusion protein recovered from the host cells do not contain a methionine at the N-terminus.

In some embodiments, purifying recombinant ADP-ribosyl transferase C3 (C3 fusion protein), comprises providing a biological sample comprising a recombinant C3 fusion protein having an amino acid sequence of SEQ ID NO:1, and subjecting the biological sample to a series of chromatography steps comprising at least one cation exchange chromatography step and at least one hydrophobic interaction chromatography step.

In one aspect, the present invention provides a method of purifying recombinant ADP-ribosyl transferase C3 (C3 fusion protein), comprising providing a biological sample comprising a recombinant C3 fusion protein having an amino acid sequence of SEQ ID NO:1, and subjecting the biological sample to a series of chromatography steps comprising at least one cation exchange chromatography step and at least one hydrophobic interaction chromatography step. In some embodiments, the at least one cation exchange chromatography step includes two or more cation exchange chromatography steps. In some embodiments, the at least one cation exchange chromatography step includes a first cation exchange chromatography step and a second cation exchange chromatography step. In some embodiments, the at least one hydrophobic interaction chromatography step follows the at least cation exchange chromatography step. In some embodiments, the series of chromatography steps comprise a first cation exchange chromatography step, a second cation exchange chromatography step and a hydrophobic interaction chromatography step, in that order.

In some embodiments, the at least one cation exchange chromatography step uses a column comprising SP Sepharose.

In some embodiments, the at least one cation exchange chromatography step uses a column with a bed height of 5 cm-30 cm (e.g., a bed height of 5 cm, 10 cm, 15 cm, 20 cm, 25 cm, or 30 cm). In some embodiments, the at least one cation exchange chromatography step uses a column with a loading velocity of 100 cm/hr-200 cm/hr. In some embodiments, the at least one cation exchange chromatography step uses a column with a load conductivity of 7 mS/cm-8 mS/cm.

In some embodiments, the first and second cation exchange chromatography steps use identical columns. In some embodiments, the first and second cation exchange chromatography steps use different columns.

In some embodiments, the at least one hydrophobic interaction chromatography step uses a column comprising Butyl 650M resin.

In some embodiments, the at least one hydrophobic interaction chromatography step uses a column with a bed height of 5 cm-30 cm (e.g., a bed height of 5 cm, 10 cm, 15 cm, 20 cm, 25 cm, or 30 cm).

In some embodiments, the method further comprises one or more steps of Ultrafiltration/Diafiltration I (UF/DF I) and membrane adsorption before, between or after the chromatography steps.

In some embodiments, the method further comprises a step of concentrating the purified recombinant C3 fusion protein to a concentration of 0.1 mg/mL-40 mg/mL.

In some embodiments, the biological sample comprises homogenate of cells expressing the recombinant C3 fusion protein. In some embodiments, the cells are bacterial cells. In some embodiments, the cells comprise a nucleic acid encoding a recombinant C3 fusion protein having an amino acid sequence of SEQ ID NO: 2.

In some embodiments, at least 80%, 85%, 90%, 5%, 96%, 97%, 98%, or 99% of the purified recombinant C3 fusion protein do not contain a methionine at the N-terminus. In some embodiments, substantially all purified recombinant C3 fusion protein do not contain a methionine at the N-terminus.

In some embodiments, the purified recombinant C3 fusion protein has a purity of equal to or greater than 85% measured by main peak of IE-HPLC. In some embodiments, the purity is equal to or greater than 90% measured by the main peak of IE-HPLC.

In some embodiments, the purified recombinant C3 fusion protein has a protein concentration of about 31-37 mg/mL.

In one aspect, the present invention provides a C3 recombinant ADP-ribosyl transferase protein composition purified according to a method described herein.

In one aspect, the present invention provides a method of preparing a therapeutic composition, comprising mixing a therapeutically effective amount of a therapeutic protein with a fibrinogen composition that does not contain a thrombin to generate a therapeutic polypeptide-fibrinogen composition, wherein the therapeutic protein comprises a transport domain covalently linked to a therapeutic active domain, and wherein the transport domain is selected from a Tat peptide, an antennapedia peptide, a fragment or subdomain thereof, or a polypeptide having an amino acid sequence having at least 80% sequence identity thereto; and combining the therapeutic protein-fibrinogen composition with a thrombin composition to generate a therapeutic composition.

In some embodiments, the transport domain comprises an amino acid sequence of EFVMNPANAQGRHTPGTRL (SEQ ID NO: 10).

In some embodiments, the therapeutic active domain comprises an ADP-ribosyl transferase C3 protein.

In one aspect, the present invention provides a method for preparing a therapeutic composition to promote neuroregeneration or neuroprotection, or to treat spinal cord injury or facilitate axon growth, comprising: mixing a therapeutically effective amount of a pharmaceutical composition comprising a polypeptide having an amino acid sequence at least 85% (e.g., at least 90%, 92%, 94%, 95%, 96%, 97%, 98%, or 99%%) identical to SEQ ID NO:1 with a fibrinogen composition that does not contain a thrombin to generate a therapeutic protein-fibrinogen solution; and combining the therapeutic protein-fibrinogen solution with a thrombin composition to generate a therapeutic composition to promote neuroregeneration and neuroprotection.

In some embodiments, the therapeutically effective amount of the pharmaceutical composition is first added to a solution comprising one or more plasminogen-activator inhibitors or plasmin inhibitors before mixing with the fibrinogen composition.

In some embodiments, the fibrinogen composition comprises fibrinogen and, albumin, one or more blood coagulation factors, and/or globulin.

In some embodiments, the therapeutic protein-fibrinogen solution and the thrombin composition is combined using a Duploject Syringe.

In some embodiments, the therapeutic composition to promote neuroregeneration and neuroprotection is a tissue adhesive.

In one aspect, the present invention provides a method of treating spinal cord injury in a subject in need thereof, comprising: mixing a therapeutically effective amount of a pharmaceutical composition comprising a polypeptide having an amino acid sequence at least 85% (e.g., at least 90%, 92%, 94%, 95%, 96%, 97%, 98%, or 99%%) identical to SEQ ID NO:1 with a fibrinogen composition that does not contain a thrombin to generate a therapeutic protein-fibrinogen solution; combining the therapeutic protein-fibrinogen solution with a thrombin composition to generate a therapeutic composition to promote neuroregeneration and neuroprotection; and administering the therapeutic composition to the subject in need of treatment of spinal cord injury.

In one aspect, the present invention provides a method of facilitating axon growth in a subject in need thereof, comprising: mixing a therapeutically effective amount of a pharmaceutical composition comprising a polypeptide having an amino acid sequence at least 85% (e.g., at least 90%, 92%, 94%, 95%, 96%, 97%, 98%, or 99%%) identical to SEQ ID NO:1 with a fibrinogen composition that does not contain a thrombin to generate a therapeutic protein-fibrinogen solution; combining the therapeutic protein-fibrinogen solution with a thrombin composition to generate a therapeutic composition to promote neuroregeneration and neuroprotection; and administering the therapeutic composition to the subject in need of axon growth treatment.

In one aspect, the present invention provides a method of repairing tissue, comprising: mixing a therapeutically effective amount of a pharmaceutical composition comprising a polypeptide having an amino acid sequence at least 85% (e.g., at least 90%, 92%, 94%, 95%, 96%, 97%, 98%, or 99%%) identical to SEQ ID NO:1 with a fibrinogen composition that does not contain a thrombin to generate a therapeutic protein-fibrinogen solution; combining the therapeutic protein-fibrinogen solution with a thrombin composition to generate a therapeutic composition to promote neuroregeneration and neuroprotection; and administering the therapeutic composition to the subject in need of tissue repairing.

In some embodiments, the pharmaceutical composition is first added to a solution comprising one or more plasminogen-activator inhibitors or plasmin inhibitors before mixing with the fibrinogen composition.

In some embodiments, the one or more plasminogen-activator inhibitors or plasmin inhibitors comprises aprotinin.

In some embodiments, the thrombin composition comprises thrombin and calcium chloride.

In some embodiments, the therapeutic active-fibrinogen solution and the thrombin composition are combined and administered using a Duploject Syringe to the subject in need thereof.

In one aspect, the present invention provides a kit to promote neuroregeneration or neuroprotection, treating spinal cord injury, or facilitating axon growth comprising: a first container containing a pharmaceutical composition comprising a polypeptide having an amino acid sequence at least 85% (e.g., at least 90%, 92%, 94%, 95%, 96%, 97%, 98%, or 99%%) identical to SEQ ID NO:1; a second container containing a fibrinogen composition; and a third container containing a thrombin composition.

In some embodiments, the fibrinogen composition in the kit comprises fibrinogen and, albumin, one or more blood coagulation factors, and/or globulin.

In some embodiments, the kit further comprises an additional container containing a solution comprising one or more plasminogen-activator inhibitors or plasmin inhibitors. In some embodiments, the one or more plasminogen-activator inhibitors or plasmin inhibitors comprises aprotinin.

In some embodiments, wherein the kit further comprises a solution comprising calcium chloride.

In some embodiments, the kit further comprises a syringe. In some embodiments, the syringe is a Duploject Syringe.

In one aspect, the present invention provides a kit to promote neuroregeneration or neuroprotection, treating spinal cord injury, or facilitating axon growth, comprising: a first chamber containing a pharmaceutical composition comprising a polypeptide having an amino acid sequence at least 85% (e.g., at least 90%, 92%, 94%, 95%, 96%, 97%, 98%, or 99%%) identical to SEQ ID NO:1 and a fibrinogen composition; and a second chamber containing a thrombin composition.

In some embodiments, the first chamber further contains one or more plasminogen-activator inhibitors or plasmin inhibitors.

In some embodiments, the one or more plasminogen-activator inhibitors or plasmin inhibitors comprises aprotinin.

In some embodiments, the thrombin composition comprises thrombin and calcium chloride.

In some embodiments, the method or the kit comprises a polypeptide having an amino acid sequence at least 90% identical to SEQ ID NO:1.

In some embodiments, the method or the kit comprises a polypeptide having an amino acid sequence at least 95% identical to SEQ ID NO:1.

In some embodiments, the method or the kit comprises a polypeptide having an amino acid sequence identical to SEQ ID NO:1.

In some embodiments, the first amino acid of the polypeptide is not a methionine.

In some embodiments, the method or the kit comprises a polypeptide having an amino acid sequence identical to SEQ ID NO:1. In some embodiments, the method or the kit comprises a polypeptide having an amino acid sequence identical to SEQ ID NO: 8. In some embodiments, the method or the kit comprises a polypeptide having an amino acid sequence identical to SEQ ID NO: 9.

In one aspect, the present invention provides a method for preparing a therapeutic composition to promote neuroregeneration or neuroprotection, or to treat spinal cord injury or facilitate axon growth, comprising: mixing a therapeutically effective amount of a pharmaceutical composition comprising a purified recombinant C3 fusion protein having an amino acid sequence at least 85% identical to SEQ ID NO:1, wherein the purified recombinant C3 fusion protein has a purity of equal to or greater than 80% measured by main peak of IE-HPLC, with a fibrinogen composition that does not contain a thrombin to generate a therapeutic protein-fibrinogen solution; and combining the therapeutic protein-fibrinogen solution with a thrombin composition to generate a therapeutic composition to promote neuroregeneration and neuroprotection.

In some embodiments, the therapeutically effective amount of the pharmaceutical composition is first added to a solution comprising one or more plasminogen-activator inhibitors or plasmin inhibitors before mixing with the fibrinogen composition.

In some embodiments, the fibrinogen composition comprises fibrinogen and, albumin, one or more blood coagulation factors, and/or globulin.

In some embodiments, the therapeutic protein-fibrinogen solution and the thrombin composition is combined using a Duploject Syringe.

In some embodiments, the therapeutic composition to promote neuroregeneration and neuroprotection is a tissue adhesive.

In one aspect, the present invention provides, a method of treating spinal cord injury, facilitating axon growth, or repairing tissue, in a subject in need thereof, comprising: mixing a therapeutically effective amount of a pharmaceutical composition comprising a purified recombinant C3 fusion protein having an amino acid sequence at least 85% identical to SEQ ID NO:1, wherein the purified recombinant C3 fusion protein has a purity of equal to or greater than 80% measured by main peak of IE-HPLC, with a fibrinogen composition that does not contain a thrombin to generate a therapeutic protein-fibrinogen solution; combining the therapeutic protein-fibrinogen solution with a thrombin composition to generate a therapeutic composition to promote neuroregeneration and neuroprotection; and administering the therapeutic composition to the subject in need of treatment of spinal cord injury.

In some embodiments, the pharmaceutical composition is first added to a solution comprising one or more plasminogen-activator inhibitors or plasmin inhibitors before mixing with the fibrinogen composition.

In some embodiments, the one or more plasminogen-activator inhibitors or plasmin inhibitors comprises aprotinin.

In some embodiments, the thrombin composition comprises thrombin and calcium chloride.

In some embodiments, the therapeutic active-fibrinogen solution and the thrombin composition are combined and administered using a Duploject Syringe to the subject in need thereof.

In one aspect, the present invention provides a kit to promote neuroregeneration or neuroprotection, treating spinal cord injury, or facilitating axon growth comprising: (A) a first container containing a pharmaceutical composition comprising a purified recombinant C3 fusion protein having an amino acid sequence at least 85% identical to SEQ ID NO:1, wherein the purified recombinant C3 fusion protein has a purity of equal to or greater than 80% measured by main peak of IE-HPLC; a second container containing a fibrinogen composition; and a third container containing a thrombin composition; or (B) a first chamber containing a pharmaceutical composition comprising a purified recombinant C3 fusion protein having an amino acid sequence at least 85% identical to SEQ ID NO:1, wherein the purified recombinant C3 fusion protein has a purity of equal to or greater than 80% measured by main peak of IE-HPLC; and a second chamber containing a thrombin composition.

In some embodiments, the fibrinogen composition comprises fibrinogen and, albumin, one or more blood coagulation factors, and/or globulin.

In some embodiments, the kit further comprises an additional container containing a solution comprising one or more plasminogen-activator inhibitors or plasmin inhibitors. In some embodiments, the one or more plasminogen-activator inhibitors or plasmin inhibitors comprises aprotinin.

In some embodiments, the kit further comprises a solution comprising calcium chloride.

In some embodiments, the kit further comprises a syringe. In some embodiments, the syringe is a Duploject Syringe.

In some embodiments, pharmaceutical composition comprises the purified recombinant C3 protein having an amino acid sequence at least 90% identical to SEQ ID NO:1. In some embodiments, the purified recombinant C3 protein having an amino acid sequence at least 95% identical to SEQ ID NO:1. In some embodiments, the purified recombinant C3 protein having an amino acid sequence identical to SEQ ID NO:1. In some embodiments, the purified recombinant C3 protein has 213-231 amino acids in total. In some embodiments, the purified recombinant C3 protein has 213-231 amino acids in total. In some embodiments, the purified recombinant C3 protein has 213 the purified recombinant C3 protein having an amino acid sequence at least 90% identical to SEQ ID NO:1.

In some embodiments, the purified recombinant C3 protein having an amino acid sequence at least 95% identical to SEQ ID NO:1. In some embodiments, the purified recombinant C3 protein having an amino acid sequence identical to SEQ ID NO:1. In some embodiments, the purified recombinant C3 protein has 213-231 amino acids in total. In some embodiments, the purified recombinant C3 has 231 amino acids in total.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWING

The drawings are for illustration purposes only not for limitation.

DEFINITIONS

Figure 1:
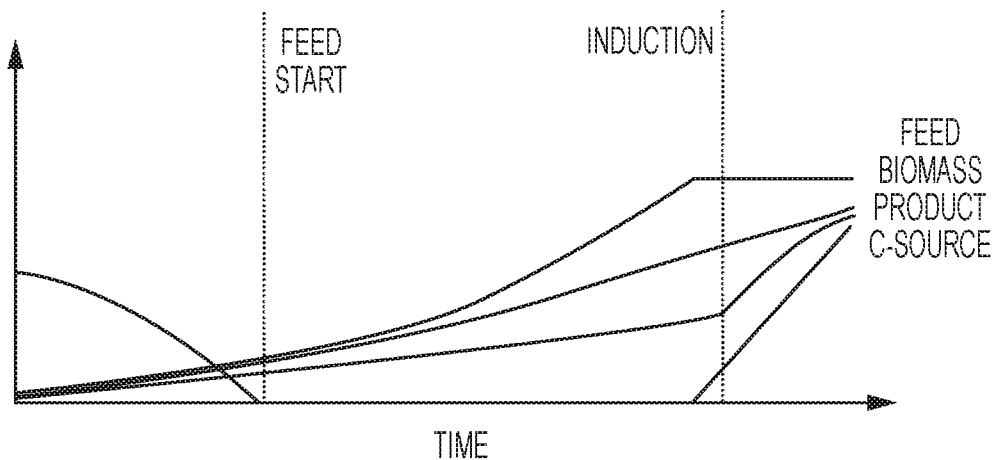
FIG. 1 shows a graphical representation of an exemplary exponential fermentation feed strategy that is carbon source (c-source) limiting with controlled growth.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Amino acid: As used herein, term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Batch culture or batch mode: The term "batch culture" or "batch mode" as used herein refers to a method of culturing cells in which the components that will ultimately be used in culturing the cells, including the medium (see definition of "medium" below) as well as the cells themselves, are provided at the beginning of the culturing process. Thus, a batch culture or batch mode typically refers to a culture allowed to progress from inoculation to conclusion of either the culture process or a density without refeeding the cultured cells with fresh medium. A batch culture is typically stopped at some point and the cells and/or components in the medium are harvested and optionally purified.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Bioreactor: The term "bioreactor" as used herein refers to a vessel used for the growth of microorganisms and mammalian cell culture. A bioreactor can be of any size so long as it is useful for the culturing cells. Typically, a bioreactor will be at least 1 liter and may be 5, 10, 15, 20, 30 100, 250, 300, 500, 1000, 2500, 5000, 8000, 10,000, 12,0000 liters or more, or any volume in between. Internal conditions of a bioreactor, including, but not limited to pH, osmolarity, CO2 saturation, O2 saturation, temperature and combinations thereof, are typically controlled during the culturing period. A bioreactor can be composed of any material that suitable for holding cells in media under the culture conditions of the present invention, including glass, plastic or metal. In some embodiments, a bioreactor may be used for performing animal cell culture. In some embodiments, a bioreactor may be used for performing mammalian cell culture. In some embodiments, a bioreactor may be used with cells and/or cell lines derived from such organisms as, but not limited to, mammalian cell, insect cells, bacterial cells, yeast cells and human cells. In some embodiments, a bioreactor is used for large-scale cell culture production and is typically at least 30 liters and may be 100, 200, 300, 500, 1000, 2500, 5000, 8000, 10,000, 12,0000 liters or more, or any volume in between. In some embodiments, a bioreactor may comprise a fermentor. One of ordinary skill in the art will be aware of and will be able to choose suitable bioreactors for use in practicing the present invention. As used herein, the term "bioreactor" and "fermentor" may be used interchangeably.

Cell density: The term "cell density" as used herein refers to that number of cells present in a given volume of medium.

Cell culture or culture: These terms as used herein refer to a cell population that is gown in a medium under conditions suitable to survival and/or growth of the cell population. As will be clear to those of ordinary skill in the art, these terms as used herein may refer to the combination comprising the cell population and the medium in which the population is grown. As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

Chromatography: As used herein, the term "chromatography" refers to a technique for separation of mixtures. Typically, the mixture is dissolved in a fluid called the "mobile phase," which carries it through a structure holding another material called the "stationary phase." Column chromatography is a separation technique in which the stationary bed is within a tube, i.e., column Cultivation: As used herein, the term "cultivation" or grammatical equivalents refers to a process of maintaining cells under conditions favoring growth or survival. The terms "cultivation" and "cell culture" or any synonyms are used inter-changeably in this application.

Culture vessel: As used herein, the term "culture vessel" refers to any container that can provide an aseptic environment for culturing cells. Exemplary culture vessels include, but are not limited to, glass, plastic, or metal containers.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery).

Elution: As used herein, the term "elution" refers to the process of extracting one material from another by washing with a solvent. For example, in ion-exchange chromatography, elution is a process to wash loaded resins to remove captured ions.

Eluate: As used herein, the term "eluate" refers to a combination of mobile phase "carrier" and the analyte material that emerge from the chromatography, typically as a result of eluting.

Equilibrate or Equilibration: As used herein, the terms "equilibrate" or "equilibration" in relation to chromatography refer to the process of bringing a first liquid (e.g., buffer) into balance with another, generally to achieve a stable and equal distribution of components of the liquid (e.g., buffer). For example, in some embodiments, a chromatographic column may be equilibrated by passing one or more column volumes of a desired liquid (e.g., buffer) through the column.

Expression: As used herein, "expression" of a nucleic acid sequence refers to translation of an mRNA into a polypeptide, assemble multiple polypeptides into an intact protein (e.g., enzyme) and/or post-translational modification of a polypeptide or fully assembled protein (e.g., enzyme). In some embodiments, protein expression encompasses the process of transcription of the DNA encoding a polypeptide of interest (e.g., a recombinant C3 fusion protein) into an mRNA transcript and translation of an mRNA transcript into a polypeptide, the assembly into an intact protein (e.g., enzyme) and/or post-translational modification of a polypeptide or fully assembled protein (e.g., enzyme). In this application, the terms "expression" and "production," and grammatical equivalent, are used inter-changeably.

Fed-batch culture or Fed-batch mode: The term "fed-batch culture" or "fed-batch mode" as used herein refers to a method of culturing cells in which additional components are provided to the culture at some time subsequent to the beginning of the culture process. The provided components typically comprise nutritional supplements for the cells which have been depleted during the culturing process. A fed-batch culture is typically stopped at some point and the cells and/or components in the medium are harvested and optionally purified.

Fermentor or Fermenter: As used herein, "fermentor" or "fermenter" refers to an apparatus that maintains optimal conditions for the growth of microorganisms. In some embodiments, a fermentor may be used in large-scale fermentation and in the commercial production of recombinant proteins. In some embodiments a bioreactor may also comprise a fermentor. Bioreactors such as steel fermentors can accommodate very large culture volumes. Bioreactors also typically allow for the control of culture conditions such as temperature, pH, oxygen tension, and carbon dioxide levels. For example, bioreactors are typically configurable, for example, using ports attached to tubing, to allow gaseous components, like oxygen or nitrogen, to be bubbled through a liquid culture. Other culture parameters, such as the pH of the culture media, the identity and concentration of trace elements, and other media constituents can also be more readily manipulated using a bioreactor. As used herein, the term "bioreactor", "fermentor" and "fermenter" may be used interchangeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Impurities: As used herein, the term "impurities" refers to substances inside a confined amount of liquid, gas, or solid, which differ from the chemical composition of the target material or compound. Impurities are also referred to as contaminants.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.). In some embodiments, percentage of purity is calculated using an assay such as SDS-PAGE (e.g., with Coomassie Blue staining or silver staining), SE-HPLC, RP-HPLC, IE-HPLC, to name but a few.

Load: As used herein, the term "load" refers to, in chromatography, adding a sample-containing liquid or solid to a column. In some embodiments, particular components of the sample loaded onto the column are then captured as the loaded sample passes through the column. In some embodiments, particular components of the sample loaded onto the column are not captured by, or "flow through", the column as the loaded sample passes through the column.

Local distribution or delivery: As used herein, the terms "local distribution," "local delivery," or grammatical equivalent, refer to tissue specific delivery or distribution. Typically, local distribution or delivery requires a protein (e.g., enzyme) encoded by mRNAs be translated and expressed intracellularly or with limited secretion that avoids entering the patient's circulation system.

Medium: The terms as used herein refer to a solution containing nutrients which nourish growing cells. Typically, these solutions may provide essential and non-essential amino acids, vitamins, energy sources, lipids, and trace elements required by the cell for minimal growth and/or survival. The solution may also contain components that enhance growth and/or survival above the minimal rate, including hormones and growth factors. In some embodiments, the medium may also comprise one or more antibiotics, which serve as selectable markers to ensure that virtually all cells retain the plasmid which encodes the target protein. In some embodiments, medium is formulated to a pH and salt concentration optimal for cell survival and proliferation. In some embodiments, medium may be a "chemically defined medium". In some embodiments, chemically defined medium is a medium in which all components within the medium have a known chemical structure.

Optical density: The term "optical density" refers to a reading of a bacterial culture which is a measure of the light scattering, which varies depending on the distance between the sample and the detector. Optical density (OD) is a common method to quantify the concentration of substances (Beer-Lambert law), since the absorbance is proportional to the concentration of the absorbing species in the sample Calibration of each individual spectrophotometer is required to facilitate accurate conversion of OD measurements into the number of cells per ml.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Pool: As used herein, the term "pool" in relation to chromatography refers to combining one or more fractions of fluid that has passed through a column together. For example, in some embodiments, one or more fractions which contain a desired component of a sample that has been separated by chromatography (e.g., "peak fractions") can be "pooled" together generate a single "pooled" fraction.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. In some embodiments, a protein can sometimes include more than one polypeptide chain, for example linked by one or more disulfide bonds or associated by other means. In some embodiments, polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Recombinant protein and Recombinant polypeptide: These terms as used herein refer to a polypeptide expressed from a host cell that has been genetically engineered to express that polypeptide. In some embodiments, a recombinant protein may be expressed in a host cell derived from an animal. In some embodiments, a recombinant protein may be expressed in a host cell derived from an insect. In some embodiments, a recombinant protein may be expressed in a host cell derived from a yeast. In some embodiments, a recombinant protein may be expressed in a host cell derived from a prokaryote. In some embodiments, a recombinant protein may be expressed in a host cell derived from *Escherichia coli* (e.g., BL21). In some embodiments, a recombinant protein may be expressed in a host cell derived from a mammal. In some embodiments, a recombinant protein may be expressed in a host cell derived from a human. In some embodiments, the recombinant expressed polypeptide may be identical or similar to a polypeptide that is normally expressed in the host cell. In some embodiments, the recombinantly expressed polypeptide may be foreign to the host cell, i.e. heterologous to peptides normally expressed in the host cell. Alternatively, in some embodiments the recombinantly expressed polypeptide can be a chimeric, in that portions of the polypeptide contain amino acid sequences that are identical or similar to polypeptides normally expressed in the host cell, while other portions are foreign to the host cell.

Seeding: The term "seeding" as used herein refers to the process of providing a cell culture to a bioreactor or another vessel for large scale cell culture production. In some embodiments a "seed culture" is used, in which the cells have been propagated in a smaller cell culture vessel, i.e. culture flask, culture plate, culture roller bottle, test tube, etc., prior to seeding. Alternatively, in some embodiments, the cells may have been frozen and thawed immediately prior to providing them to the bioreactor or vessel. The term refers to any number of cells, including a single cell.

Soluble: As used herein, the term "soluble" refers to the ability of a therapeutic agent to form a homogenous solution. In some embodiments, the solubility of the therapeutic agent in the solution into which it is administered and by which it is transported to the target site of action is sufficient to permit the delivery of a therapeutically effective amount of the therapeutic agent to the targeted site of action. Several factors can impact the solubility of the therapeutic agents. For example, relevant factors which may impact protein solubility include ionic strength, amino acid sequence and the presence of other co-solubilizing agents or salts (e.g., calcium salts). In some embodiments, therapeutic agents in accordance with the present invention are soluble in its corresponding pharmaceutical composition.

Stability: As used herein, the term "stable" refers to the ability of the therapeutic agent (e.g., a recombinant enzyme) to maintain its therapeutic efficacy (e.g., all or the majority of its intended biological activity and/or physiochemical integrity) over extended periods of time. The stability of a therapeutic agent, and the capability of the pharmaceutical composition to maintain stability of such therapeutic agent, may be assessed over extended periods of time (e.g., for at least 1, 3, 6, 12, 18, 24, 30, 36 months or more). In the context of a formulation a stable formulation is one in which the therapeutic agent therein essentially retains its physical and/or chemical integrity and biological activity upon storage and during processes (such as freeze/thaw, mechanical mixing and lyophilization). For protein stability, it can be measure by formation of high molecular weight (HMW) aggregates, loss of enzyme activity, generation of peptide fragments and shift of charge profiles.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated.

In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Therapeutic protein: As used herein, the term "therapeutic protein" refers to a protein with pharmacological activity. Therapeutic proteins can act by replacing a protein that is deficient or abnormal; augmenting an existing pathway; providing a novel function or activity; interfering with a molecule or organism; and/or delivering other compounds or proteins, such as a radionuclide, cytotoxic drug, or effector proteins. In some embodiments, therapeutic proteins can also be grouped based on their molecular types that include antibody-based drugs, Fc fusion proteins, anticoagulants, blood factors, bone morphogenetic proteins, engineered protein scaffolds, enzymes, growth factors, hormones, interferons, interleukins, and thrombolytics. In some embodiments, therapeutic proteins can be classified based on their molecular mechanism of activity as binding non-covalently to target, e.g., mAbs; affecting covalent bonds, e.g., enzymes; and exerting activity without specific interactions, e.g., serum albumin.

Treating: As used herein, the term "treat," "treatment," or "treating" refers to any method used to partially or completely alleviate, ameliorate, relieve, inhibit, prevent, repair, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, methods of producing and purifying therapeutic C3 transferase fusion proteins. In some embodiments, the present invention provides a method for producing C3 fusion proteins by cultivating host cells under conditions that promote expression at a specific productivity rate. In some embodiments, the present invention provides methods of producing C3 fusion proteins in a large scale vessel under conditions that involve fermentation. In some embodiments, the present invention provides a method of purifying a recombinant C3 fusion protein from an impure preparation (e.g., unprocessed biological materials, such as C3 fusion protein-containing cells and/or culture medium) using a series of chromatography steps (e.g., ion exchange, hydrophobic interaction chromatography).

In some embodiments, the present invention provides a pharmaceutical composition comprising a therapeutic C3 fusion protein. In some embodiments, the present invention provides a pharmaceutical composition comprising a mixture of therapeutic C3 fusion proteins. In various embodiments, pharmaceutical compositions provided by the present invention are used to effectively treat spinal cord injury or other CNS trauma, facilitate axon growth or aid in other tissue repair.

In some embodiments, the present invention provides a method of preparing a therapeutic composition by mixing a therapeutically effective amount of a therapeutic protein (e.g., an ADP-ribosyl transferase C3 protein) with a fibrinogen composition that does not contain a thrombin to generate a therapeutic protein-fibrinogen composition; and combining the therapeutic protein-fibrinogen composition with a thrombin composition to generate a therapeutic composition. In some embodiments, a therapeutic composition prepared according to the present invention is a tissue adhesive that may be administered to a spinal cord injury site to facilitate axon growth.

Various aspects of the invention are described in further detail in the following subsections. The use of subsections is not meant to limit the invention. Each subsection may apply to any aspect of the invention. In this application, the use of "or" means "and/or" unless stated otherwise.

C3 Fusion Protein

Among other things, the present invention is used to produce a C3 fusion protein containing an ADP-ribosyl transferase C3 domain and a transport domain. In some embodiments, a C3 fusion protein comprises an amino acid sequence of a transport domain covalently linked to an amino acid sequence of an ADP-ribosyl transferase C3 domain, wherein the amino acid sequence of said transport domain is selected from a Tat peptide or antennapedia peptide, a fragment or subdomain of Tat peptide or antennapedia peptide, a polypeptide derived from a nucleotide sequence encoding a Tat peptide or antennapedia peptide, or a polypeptide having an amino acid sequence having at least 80% (e.g., at least 85%, 90%, 92%, 94%, 95%, 96%, 97%, 98%, 99%, or 100%) sequence identity thereto and wherein the amino acid sequence of the active domain of the C3 fusion protein is selected from an ADP-ribosyl transferase C3, a fragment thereof retaining ADP-ribosyl transferase activity, or an amino acid sequence having at least 80% (e.g., at least 85%, 90%, 92%, 94%, 95%, 96%, 97%, 98%, 99%, or 100%) sequence identity thereto.

In some embodiments, a C3 fusion protein amino acid sequence is as follows:

```
                                             (SEQ ID NO: 1)
SAYSNTYQEFTNIDQAKAWGNAQYKKYGLSKSEKEAIVSYTKSASEINGK

LRQNKGVINGFPSNLIKQVELLDKSFNKMKTPENIMLFRGDDPAYLGTEF

QNTLLNSNGTINKTAFEKAKAKFLNKDRLEYGYISTSLMNVSQFAGRPII

TKFKVAKGSKAGYIDPISAFAGQLEMLLPRHSTYHIDDMRLSSDGKQIII

TATMMGTAINPKEFVMNPANAQGRHTPGTRL
```

In some embodiments, a C3 fusion protein amino acid sequence is as follows:

```
                                             (SEQ ID NO: 2)
MSAYSNTYQEFTNIDQAKAWGNAQYKKYGLSKSEKEAIVSYTKSASEING

KLRQNKGVINGFPSNLIKQVELLDKSFNKMKTPENIMLFRGDDPAYLGTE

FQNTLLNSNGTINKTAFEKAKAKFLNKDRLEYGYISTSLMNVSQFAGRPI

ITKFKVAKGSKAGYIDPISAFAGQLEMLLPRHSTYHIDDM

RLSSDGKQIIITATMMGTAINPKEFVMNPANAQGRHTPGTRL
```

In some embodiments, a C3 fusion protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with SEQ ID NO: 1. In some embodiments, a C3 fusion protein comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with SEQ ID NO: 2.

As used herein, the term "recombinant C3 fusion protein" refers to any molecule or a portion of a molecule that can substitute for at least partial activity of naturally-occurring ADP-ribosyl transferase C3 protein. As used herein, the terms "recombinant C3 enzyme" and "recombinant C3 protein", and grammatical equivalents, are used interchangeably. In some embodiments, the present invention is used to purify a recombinant C3 fusion protein that is a polypeptide, wherein the therapeutic protein comprises an amino acid sequence of a transport domain covalently linked to an amino acid sequence of an active domain, said amino acid sequence of said active domain is selected from an ADP-ribosyl transferase C3, a fragment thereof retaining ADP-ribosyl transferase activity, or an amino acid sequence having at least 80% sequence identity thereto, and wherein said amino acid sequence of said transport domain is selected from a subdomain of Tat peptide or antennapedia peptide, a fragment of Tat peptide or antennapedia peptide, a polypeptide derived from a nucleotide sequence encoding a Tat peptide or antennapedia peptide, or an amino acid sequence having at least 80% sequence identity thereto.

In some embodiments, the DNA sequence encoding a C3 fusion protein is as follows:

```
                                        (SEQ ID NO: 3)
ATGTCGGCTTATTCAAATACTTACCAGGAGTTTACTAATATTGATCAAGC

AAAAGCTTGGGGTAATGCTCAGTATAAAAAGTATGGACTAAGCAAATCAG

AAAAAGAAGCTATAGTATCATATACTAAAAGCGCTAGTGAAATAAATGGA

AAGCTAAGACAAAATAAGGGAGTTATCAATGGATTTCCTTCAAATTTAAT

AAAACAAGTTGAACTTTTAGATAAATCTTTTAATAAAATGAAGACCCCTG

AAAATATTATGTTATTTAGAGGCGACGACCCTGCTTATTTAGGAACAGAA

TTTCAAAACACTCTTCTTAATTCAAATGGTACAATTAATAAAACGGCTTT

TGAAAAGGCTAAAGCTAAGTTTTTAAATAAAGATAGACTTGAATATGGAT

ATATTAGTACTTCATTAATGAATGTTTCTCAATTTGCAGGAAGACCAATT

ATTACAAAATTTAAAGTAGCAAAAGGCTCAAAGGCAGGATATATTGACCC

TATTAGTGCTTTTGCAGGACAACTTGAAATGTTGCTTCCTAGACATAGTA

CTTATCATATAGACGATATGAGATTGTCTTCTGATGGTAAACAAATAATA

ATTACAGCAACAATGATGGGCACAGCTATCAATCCTAAAGAATTCGTGAT

GAATCCCGCAAACGCGCAAGGCAGACATACACCCGGTACCAGACTCTAG
```

In some embodiments, a DNA sequence encoding a C3 fusion protein comprises a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with SEQ ID NO: 3.

Production of Recombinant C3 Fusion Proteins

The present invention may be used to purify a recombinant C3 fusion protein produced by various means. For example, a C3 fusion protein may be recombinantly produced by utilizing a host cell system engineered to express a C3 fusion protein-encoding nucleic acid. Typically, cells that are engineered to express recombinant C3 fusion protein may comprise a transgene that encodes a recombinant C3 fusion protein described herein. It should be appreciated that the nucleic acids encoding recombinant C3 fusion protein may contain regulatory sequences, gene control sequences, promoters, non-coding sequences and/or other appropriate sequences for expressing the recombinant C3 fusion protein. Typically, the coding region is operably linked with one or more of these nucleic acid components. In some embodiments, SEQ ID NO: 3 is cloned into a pET9a vector with a Kanamycin resistance gene for antibiotic selection.

"Regulatory sequences" typically refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences. Sometimes, "regulatory sequences" are also referred to as "gene control sequences".

"Promoter" typically refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions.

The "3' non-coding sequences" typically refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

The "translation leader sequence" or "5' non-coding sequences" typically refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency.

Typically, the term "operatively linked" or "operably linked" refers to the association of two or more nucleic acid fragments on a single nucleic acid fragment so that the function of one is affected by the other. For example, a promoter is operatively linked with a coding sequence when it is capable of affecting the expression of that coding sequence (i.e., that the coding sequence is under the transcriptional control of the promoter). Coding sequences can be operatively linked to regulatory sequences in sense or antisense orientation.

The coding region of a transgene may include one or more silent mutations to optimize codon usage for a particular cell type. For example, the codons of a C3 fusion protein transgene may be optimized for expression in a vertebrate cell. In some embodiments, the codons of a C3 fusion protein transgene may be optimized for expression in a mammalian cell. In some embodiments, the codons of a C3 fusion protein transgene may be optimized for expression in a human cell.

Optionally, a construct may contain additional components such as one or more of the following: a splice site, an enhancer sequence, a selectable marker gene under the control of an appropriate promoter, an amplifiable marker gene under the control of an appropriate promoter, and a matrix attachment region (MAR) or other element known in the art that enhances expression of the region where it is inserted.

Once transfected or transduced into host cells, a suitable vector can express extrachromosomally (episomally) or integrate into the host cell's genome.

Host Cells

As used herein, the term "host cells" refers to cells that can be used to produce recombinant C3 fusion protein. In particular, host cells are suitable for producing recombinant C3 fusion protein at a large scale. In some embodiments, host cells are able to produce C3 fusion protein in an amount ranging from about or greater than 0.7 g/L of culture, 0.8 g/L of culture, 0.9 g/L of culture, 1.0 g/L of culture, 1.1 g/L of culture, 1.2 g/L of culture, 1.3 g/L of culture, 1.4 g/L of culture, 1.5 g/L of culture, 1.6 g/L of culture, 1.7 g/L of culture, 1.8 g/L of culture, 1.9 g/L of culture, 2.0 g/L of culture, 2.1 g/L of culture, 2.2 g/L of culture, 2.3 g/L of culture, 2.4 g/L of culture, 2.5 g/L of culture, 3 g/L of culture, 3.5 g/L of culture, 4 g/L of culture, 4.5 g/L of culture, or 5 g/L of culture according to the culturing conditions described herein.

Suitable host cells can be derived from a variety of organisms, including, but not limited to, mammals, plants, birds (e.g., avian systems), insects, yeast, and bacteria. In some embodiments, host cells are mammalian cells. Any mammalian cell susceptible to cell culture, and to expression of polypeptides, may be utilized in accordance with the present invention as a host cell. Non-limiting examples of mammalian cells that may be used in accordance with the present invention include human embryonic kidney 293 cells (HEK293), HeLa cells; BALB/c mouse myeloma line (NSO/l, ECACC No: 85110503); human retinoblasts (PER.C6 (CruCell, Leiden, The Netherlands)); monkey kidney CV1 line transformed by SV40 (COS-7, ATCC CRL 1651); human fibrosarcomacell line (e.g., HT-1080); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells +/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; a human hepatoma line (Hep G2), human cell line CAP and AGE1.HN, and Glycotope's panel.

Non-limiting examples of host cells suitable for the present invention include cells and cell lines derived from *Pichia pastoris, Pichia methanolica, Pichia angusta, Schizosacccharomyces pombe, Saccharomyces cerevisiae*, and *Yarrowia lipolytica* for yeast; *Sodoptera frugiperda, Trichoplusis ni, Drosophila melangoster* and *Manduca sexta* for insects; and *Escherichia coli, Salmonella typhimurium, Bacillus subtilis, Bacillus lichenifonnis, Bacteroides fragilis, Clostridia perfringens, Clostridia difficile* for bacteria; and *Xenopus laevis* from amphibian.

Additionally, any number of available hybridoma cell lines may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

Culture Medium

The term "medium" and "culture medium" (and grammatical equivalents) as used herein refers to a general class of solution containing nutrients suitable for maintaining and/or growing cells in vitro. Typically, media solutions provide, without limitation, essential and nonessential amino acids, vitamins, energy sources, lipids, and trace elements required by the cell for at least minimal growth and/or survival. In other embodiments, the medium may contain an amino acid(s) derived from any source or method known in the art, including, but not limited to, an amino acid(s) derived either from single amino acid addition(s) or from a peptone or protein hydrolysate addition(s) (including animal or plant source(s)). Vitamins such as, but not limited to, Biotin, Pantothenate, Choline Chloride, Folic Acid, Myo-Inositol, Niacinamide, Pyridoxine, Riboflavin, Vitamin B12, Thiamine, Putrescine and/or combinations thereof. Salts such as, but not limited to, $CaCl_2$, KCl, MgCl2, NaCl, Sodium Phosphate Monobasic, Sodium Phosphate Dibasic, Sodium Selenite, $CuSO_4$, $ZnCl_2$ and/or combinations thereof. Fatty acids such as, but not limited to, Arachidonic Acid, Linoleic Acid, Oleic Acid, Lauric Acid, Myristic Acid, as well as Methyl-beta-Cyclodextrin and/or combinations thereof). In some embodiments, media comprises additional components such as glucose, glutamine, Na-pyruvate, insulin or ethanolamine, a protective agent such as Pluronic F68. In some embodiments, the media may also contain components that enhance growth and/or survival above the minimal rate, including hormones and growth factors. Medium may also comprise one or more buffering agents. The buffering agents may be designed and/or selected to maintain the culture at a particular pH (e.g., a physiological pH, (e.g., pH 6.8 to pH 7.4)). A variety of buffers suitable for culturing cells are known in the art and may be used in the methods. Suitable buffers (e.g., bicarbonate buffers, HEPES buffer, Good's buffers, etc.) are those that have the capacity and efficiency for maintaining physiological pH despite changes in carbon dioxide concentration associated with cellular respiration. The solution is preferably formulated to a pH and salt concentration optimal for cell survival and proliferation.

In some embodiments, a medium may be a chemically defined medium. As used herein, the term "chemically-defined nutrient medium" refers to a medium of which substantially all of the chemical components are known. Defined media are media composed of pure ingredients in carefully measured concentrations dissolved in double distilled water i.e., the exact chemical composition of the medium is known. In some embodiments, they contain a simple sugar as the carbon and energy source, an inorganic nitrogen source, various mineral salts and, if necessary, growth factors (purified amino acids, vitamins, purines and pyrimidines). In some embodiments, a chemically defined medium can be prepared by combining various individual components such as, for example, essential and nonessential amino acids, vitamins, energy sources, lipids, salts, buffering agents, and trace elements, at predetermined weight or molar percentages or ratios.

In some embodiments, a medium may be a complex medium. As used herein, the term "complex medium" refers to a medium that may be rich in nutrients; they may contain water soluble extracts of plant or animal tissue (e.g., enzymatically digested animal proteins such as peptone and tryptone). In some embodiments, a sugar, often glucose, is added to serve as the main carbon and energy source. The combination of extracts and sugar creates a medium that is rich in minerals and organic nutrients, but since the exact composition is unknown, the medium is complex.

In some embodiments, a medium may be a selective/differential medium. As used herein, the term "selective/differential medium" are media based on either of the two categories above supplemented with growth-promoting or growth-inhibiting additives. The additives may be species- or organism-selective (e.g., an antibiotic such as kanamycin, a specific substrate, or an inhibitor such as cyclohexamide (artidione), which inhibits all eukaryotic growth and is typically used to prevent fungal growth in mixed cultures).

In some embodiments, a medium may be an enrichment medium. As used herein, the term "enrichment medium" may be a medium similar to selective media but designed to increase the numbers of desired microorganisms to a detectable level without stimulating the rest of the bacterial population.

In some embodiments, a medium may be a reducing medium. As used herein, the term "reducing medium" may be used to facilitate the growth of obligate anaerobes.

In some embodiments, an exemplary culture medium may be LB, Terrific, SuperBroth, YT, or 2×YT. In some embodiments, a medium suitable for the present invention is a mixture of one or more commercially available chemically-defined, complex, selective, or enrichment media. In various embodiments, a suitable medium is a mixture of two, three, four, five, six, seven, eight, nine, ten, or more commercially available chemically-defined media. In some embodiments, each individual commercially available chemically-defined medium (e.g., such as those described herein) constitutes, by weight, 1%, 2.5%, 5%, 7.5%, 10%, 12.5%, 15%, 20%, 25%, 30%, 35%, 40%, 45%, 50%, 55%, 60%, 65%, 70%, 75%, 80%, 85%, 90%, 95%, or more, of the mixture. Ratios between each individual component media may be determined by relative weight percentage present in the mixture.

Bioreactors

The invention also provides bioreactors that are useful for producing recombinant C3 fusion protein. Bioreactors may be, for example, perfusion, batch, fed-batch, repeated batch, or continuous (e.g., a continuous stirred-tank reactor model). Typically, the bioreactors comprise at least one vessel designed and configured to house medium (e.g., a chemically-defined nutrient medium). The vessel also typically comprises at least one inlet designed and configured to flow fresh nutrient media into the vessel. The vessel also typically comprises at least one outlet designed and configured to flow waste media out of the vessel. In some embodiments, the vessel may further comprise at least one filter designed and configured to minimize the extent to which isolated cells in the vessel are passed out through the at least one outlet with waste media. The bioreactor may also be fitted with one or more other components designed to maintain conditions suitable for cell growth. For example, the bioreactor may be fitted with one or more circulation or mixing devices designed and configured to circulate or mix the nutrient media within the vessel. Typically, the isolated cells that are engineered to express recombinant C3 fusion protein are suspended in the nutrient medium. Therefore, in some cases, the circulation device ensures that the isolated cells remain in suspension in the nutrient medium. In some embodiments, the cells are attached to a substrate. In some embodiments, the cells are attached to one or more substrates (e.g., microbeads) that are suspended in the nutrient medium. The bioreactor may comprise one or more ports for obtaining a sample of the cell suspension from the vessel. The bioreactor may be configured with one or more components for monitoring and/or controlling conditions of the culture, including conditions such as gas content (e.g., air, oxygen, nitrogen, carbon dioxide), flow rates, temperature, pH and dissolved oxygen levels, and agitation speed/circulation rate.

Culture Conditions

Seeding

The present invention provides a method of producing recombinant C3 fusion protein at a large scale. Typical large-scale procedures for producing a recombinant polypeptide of interest include batch cultures and fed-batch cultures. Batch culture processes traditionally comprise inoculating a large-scale production culture with a seed culture of a particular cell density, growing the cells under conditions (e.g., suitable culture medium, pH, and temperature) conducive to cell growth, viability, and/or productivity, harvesting the culture when the cells reach a specified cell density, and purifying the expressed polypeptide. Fed-batch culture procedures include an additional step or steps of supplementing the batch culture with nutrients and other components that are consumed during the growth of the cells. In some embodiments, a large-scale production method according to the present invention uses a fed-batch culture system.

Typically, a desired cell expressing C3 fusion protein is first propagated in an initial culture by any of a variety of methods well-known to one of ordinary skill in the art. The cell is typically propagated by growing it at a temperature and in a medium that is conducive to the survival, growth and viability of the cell. The initial culture volume can be of any size, but is often smaller than the culture volume of the production bioreactor used in the final production. The cell culture can be agitated or shaken to increase oxygenation of the medium and dispersion of nutrients to the cells. Alternatively or additionally, special sparging devices that are well known in the art can be used to increase and control oxygenation of the culture.

The cell density of the inoculum used to start a seed culture can be chosen by one of ordinary skill in the art. In some embodiments, a Master Cell Bank (MCB) vial or a Working Cell Bank (WCB) vial is used as the inoculum for the seed culture. In some embodiments, the MCB or WCB vial can be as low as a single cell per culture volume. In some embodiments, the MCB or WCB inoculum used to start the seed culture is greater than $1 \times 10^6$ colony forming units (CFU) per mL (e.g., greater than about $1.4 \times 10^7$, $1.4 \times 10^8$, $1.4 \times 10^9$, $1.4 \times 10^{10}$ CFU/mL and higher).

Initial cultures may be grown to any desired density before seeding a final production bioreactor. In some embodiments, once the optical density (OD) at 600 nm (OD600) reaches an optimal level, (e.g., 2-10, 2-8, 2-6, 2-4) the culture can be scaled up to the production bioreactor (e.g., a 30 L bioreactor). In some embodiments, the initial starting volume of the fermentor can be, for example, 1 L, 2 L, 3 L, 4 L, 5 L, 6 L, 7 L, 8 L, 9 L, 10 L, 11 L, 12 L, 13 L, 14 L, 15 L, 16 L, 17 L, 18 L, 19 L, or 20 L. In some embodiments, once the optical density (OD) at 600 nm (OD600) reaches an optimal level, (e.g., 2-10, 2-8, 2-6, 2-4) the culture can be scaled up to the production bioreactor (e.g., a 300 L bioreactor). In some embodiments, the initial starting volume of the fermentor can be, for example, 10 L, 20 L, 30 L, 40 L, 50 L, 60 L, 70 L, 80 L, 90 L, 100 L, 110 L, 120 L, 130 L, 140 L, 150 L, 160 L, 170 L, 180 L, 190 L, or 200 L.

In some embodiments, it may be desirable to wash the removed seed culture cells with a medium before seeding the next bioreactor to remove any unwanted metabolic waste products or medium components. The medium may be the medium in which the cells were previously grown or it may be a different medium or a washing solution selected by the practitioner of the present invention.

The cells may then be diluted to an appropriate density for seeding the production bioreactor. In some embodiments, the cells are diluted into the same medium that will be used in the production bioreactor. Alternatively, the cells can be diluted into another medium or solution, depending on the needs and desires of the practitioner of the present invention or to accommodate particular requirements of the cells themselves, for example, if they are to be stored for a short period of time prior to seeding the production bioreactor.

Fermentation

Process development focused on two main challenges: low yields and lack of robustness at the fermentation step. These challenges were addressed by developing a high-cell density (HCD) fermentation process, along with optimization of the medium composition and implementation of an exponential glycerol feeding strategy. An exemplary fermentation process is shown in FIG. 1.

In some embodiments, when the cells are ready for the fermentation process, the culture conditions may be changed to maximize the production of the recombinant protein of interest. In some embodiments, such change may be a shift in one or more of a number of culture conditions including, but not limited to, temperature, pH, osmolarity, carbon source and medium. In one embodiment, the carbon source of the culture is shifted. For example, the carbon source may be shifted from glucose in the batch phase to glycerol in the feeding phase. In some embodiments, this change in carbon source is rapid. In some embodiments, this change in carbon source occurs slowly over a prolonged period of time. In some embodiments, dissolved oxygen and pH is maintained at 15-50% (e.g., 20-40%, 20-30%) and 6.5-7.5 respectively throughout the production process.

In some embodiments, the temperature is shifted up or down from the batch phase to feed phase. For example, the temperature may be shifted up or down from batch phase to the feed phase by about 1.0° C., 2.0° C., 3.0° C., 4.0° C., 5.0° C., 6.0° C., 7.0° C., 8.0° C., 9.0° C., 10.0° C. or more.

In some embodiments, to maximize yield and robustness, a high-cell density (HCD) fermentation process may be used. In some embodiments, an HCD fermentation comprises one or more phases (e.g., batch-mode phase, fed-batch mode phase). In some embodiments, an HCD fermentation comprises one or more stages of feeding (e.g., exponential feeding, constant feeding). In some embodiments, the feeding stages are the same. In some embodiments, the feeding stages are not the same.

In certain embodiments, fermentation is started in batch mode, in which a defined amount of initial carbon source (glucose) is provided in the medium. After consumption of the glucose in the medium, (carbon source limitation), a fed-batch mode is started. In the fed-batch mode, a glycerol carbon source feed solution was introduced to the fermentor at an exponential rate (e.g., exponential feeding), followed by a second phase of constant feeding. Thus, in certain embodiments, the feeding strategy consists of two stages: a first stage of exponential feeding, and a second stage of constant feeding. The feed parameters are summarized below:

$1^{st}$ stage: Exponential feeding was controlled using:

$$\text{Exp. Feed}\left[\frac{g}{h}\right] = 1000 * \left[\left(\frac{\mu}{Y_{\frac{x}{s}}} + m\right) \cdot V_0 \cdot X_0 \cdot \frac{1}{S_F} \cdot e^{(\mu \cdot t)}\right]$$

Where;
Specific growth rate, $\mu$, (1/h)
Biomass yield on glucose, Yx/s, (g/g)
Maintenance factor, m, (g/g/hr)
Initial volume of reactor before the start of feed, $V_0$, (L)
Biomass concentration before the start of feed, $X_0$, (g/L)
Feed concentration, $S_F$, (g/kg)
Time, t, (hrs)

$2^{nd}$ stage: Constant feed rate=Feed rate at the end of the exponential feeding stage.

In some embodiments, the specific growth rate, $\mu$, is in a range between 0.12-0.18/hr, the biomass yield on glucose, Yx/s, ranges from 0.32-0.48 g/g, the maintenance factor, m, ranges from 0.03-0.04 g/g/hr, the initial volume of the reactor before the start of feed, $V_0$, ranges from 12 L, the biomass concentration before the start of feed, $X_0$, ranges from 8-12 g/L, the feed concentration, $S_F$, ranges from 480-720 g/kg, and the time, t, ranges from 7-8 hrs.

In certain other embodiments, fermentation is started in batch mode, in which a defined amount of initial carbon source (glucose) is provided in the medium. After consumption of the glucose in the medium, (carbon source limitation), a fed-batch mode is started. In some embodiments, the fed-batch mode occurs in three stages wherein a glycerol carbon source feed solution is introduced to the fermentor at an exponential rate (e.g., exponential feeding), followed by a second phase of constant feeding. Following the second stage of constant feeding, a third stage of constant feeding wherein the feed rate may be the same as the feed rate in the second stage. In some embodiments, the feed rate in the third stage is reduced constant feeding at a feed rate about 0.7 times that of the second feeding stage. Thus, in certain embodiments, the feeding strategy involves three stages: a first stage of exponential feeding, a second stage of constant feeding, and a third stage of constant or reduced constant feeding. The feed parameters are summarized below:

$1^{st}$ stage: Exponential feeding was controlled using:

$$\text{Exp. Feed}\left[\frac{g}{h}\right] = 1000 * \left[\left(\frac{\mu}{Y_{\frac{x}{s}}} + m\right) \cdot V_0 \cdot X_0 \cdot \frac{1}{S_F} \cdot e^{(\mu \cdot t)}\right]$$

Where;
Specific growth rate, $\mu$, (1/h)
Biomass yield on glucose, Yx/s, (g/g)
Maintenance factor, m, (g/g/hr)
Initial volume of reactor before the start of feed, $V_0$, (L)
Biomass concentration before the start of feed, $X_0$, (g/L)
Feed concentration, $S_F$, (g/kg)
Time, t, (hrs)

$2^{nd}$ stage: Constant feed rate=Feed rate at the end of the exponential feeding stage.

3rd stage: Constant feed rate=rate at the end of $2^{nd}$ state, or Reduced constant feed rate=0.7×Feed rate of the 2nd stage (constant feeding).

Induction

In some embodiments, cells are induced with an inducing agent, wherein the inducing agent is Isopropyl β-D-1-thiogalactopyranoside (IPTG). In some embodiments, the IPTG is added at a concentration range of 0.1 mM-10 mM. In certain embodiments, the induction phase begins when the OD is between 145-175. In certain embodiments, the induction phase begins after 8-9 hours of constant feeding. In some embodiments, the third stage of constant feeding is the induction phase. In some embodiments, constant feeding is maintained during the induction phase. In other embodiments, induction triggers a reduced feed rate. In some embodiments, the temperature is shifted (e.g., reduced) during the induction phase. In some embodiments, the induction time is between 3-10 hours (e.g., 3-8, 3-6, 3-5, 4-5, 4-6, 4-7, 4-8, or 4-10 hours).

Purification of C3 Fusion Protein

Figure 2:
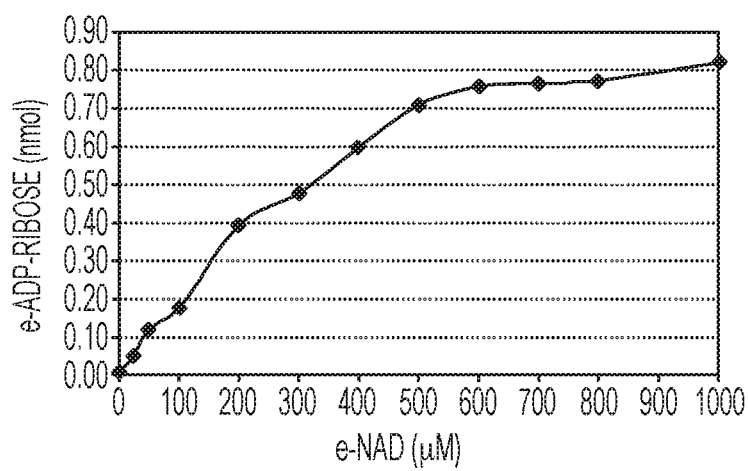
FIG. 2 shows an example of C3 fusion protein activity dependence on c-NAD concentration.

Embodiments of the invention include purification processes for the production of C3 fusion protein drug substances. A variety of techniques, in whole or in part, optionally with modifications as described herein, may be used to produce purified C3 fusion protein drug substance. For example, FIGS. 1 and 2 show exemplary flow diagrams of embodiments of the invention.

In some embodiments, the present invention provides a method of purifying recombinant C3 fusion protein from an impure preparation using a process based on one or more (e.g., two or more) of cation-exchange and hydrophobic interaction chromatography. In some embodiments, an inventive method according to the present invention involves fewer than 4 (e.g., less than 3, less than 2, or less than 1) chromatography steps. In some embodiments, an inventive method according to the present invention involves 2, 3, 4 or 5 chromatography steps. In some embodiments, an inventive method according to the present invention involves 3 chromatography steps. In some embodiments, an inventive method according to the present invention conducts one or more (e.g., two- or more) cation-exchange chromatography and hydrophobic interaction chromatography in that order. In some embodiments, an inventive method disclosed herein further includes one or more steps (e.g., two or more steps, three or more steps) of ultrafiltration/diafiltration. In some embodiments, an inventive method disclosed herein further includes one or more steps of membrane adsorption.

Cation Exchange Chromatography

In some embodiments, provided methods for purifying recombinant C3 fusion protein include one or more steps of cation-exchange chromatography. In some embodiments, provided methods for purifying recombinant C3 fusion protein include two or more steps of cation-exchange chromatography. In brief, cation exchange chromatography is a chromatographic technique which relies on charge-charge interactions between a positively charged compound and a negatively charged resin. In some embodiments, the cation-exchange chromatography is strong cation-exchange chromatography.

Cation exchange chromatography is generally practiced with either a strong or weak cation exchange column, containing a sulfonium ion, or with a weak cation exchanger, having usually a carboxymethyl (CM) or carboxylate (CX) functional group. Many suitable cation exchange resins are known in the art and are commercially available and include, but are not limited to SP-Sepharose® (e.g., SP-Sepharose XL resin), CM Sepharose®; Amberjet® resins; Amberlyst® resins; Amberlite® resins (e.g., Amberlite® IRA120); Capto resins (e.g, Capto SP ImpRes); Fractogel® resins (e.g., Fractogel EMD SO3); YMC-BioPro resins (e.g., YMC-BioPro S30); POROS® resins (e.g., POROS XS); Nuvia™ resins (e.g., Nuvia H-RS); ProPac® resins (e.g., ProPac® SCX-10, ProPac® WCX-10, ProPac® WCX-10); Praesto™ resins (e.g., Praesto SP45); TSK-GEL® resins (e.g., TSKgel BioAssist S; TSKgel SP-2SW, TSKgel SP-5PW; TSKgel SP-NPR; TSKgel SCX; TSKgel SP-STAT; TSKgel CM-5PW; TSKgel OApak-A; TSKgel CM-2SW, TSKgel CM-3SW, and TSKgel CM-STAT); and Acclaim® resins. In certain embodiments, one or more (e.g., 1, 2, 3, 4, 5) cation exchange columns are used. In certain embodiments, the cation exchange resin is a SP-Sepharose resin. In certain embodiments, the cation exchange resin is a SP-Sepharose resin, such as SP-Sepharose XL resin. In certain embodiments, the cation exchange resin is a YMC BioPro resin, such as YMC BioPro S30 resin. In further embodiments one or more cation exchange chromatography steps include a SP Sepharose resin (e.g., SP-Sepharose XL resin) and a YMC BioPro resin (e.g., YMC BioPro S30 resin).

Various bed height for the cation exchange chromatography column may be used. In some embodiments, a suitable cation exchange chromatography column has a bed height of 5 cm-30 cm. In some embodiments, a suitable cation exchange chromatography column has a bed height of 5 cm, 10 cm, 15 cm, 20 cm, 25 cm, or 30 cm. In particular embodiments, a suitable cation exchange chromatography column has a bed height of 10 cm.

Typical mobile phases for cationic exchange chromatography include relatively polar solutions, such as water, or solutions containing a buffer, such as 2-(N-morpholino)-ethanesulfonic acid (MES), 4-(2-hydroxyethyl)-1-piperazineethanesulfonic acid (HEPES), Tris (tris(hydroxymethyl) aminomethane) buffer, or phosphate buffer (e.g., sodium phosphate buffer). Thus, in certain embodiments, the mobile phase includes about 0%, 1%, 2%, 4%, 6%, 8%, 10%, 12%, 14%, 16%, 18%, 20%, 25%, 30%, 35%, 40%, 45%, 50%, 55%, 60%, 65%, 70%, 75%, 80%, 85%, 90%, 95%, or about 100% polar solution. In certain embodiments, the mobile phase includes between about 1% to about 100%, about 5% to about 95%, about 10% to about 90%, about 20% to about 80%, about 30% to about 70%, or about 40% to about 60% polar solution at any given time during the course of the separation.

Generally, a mobile phase includes a salt. For example, a salt (e.g., sodium chloride, etc.) can elute a bound protein from a cation exchange column (e.g., the counter ion is sodium and it is exchanged for the target protein, which is then released). In some embodiments, the mobile phase includes a salt concentration between about 0 to about 1.0M, e.g., between about 0 to about 0.8M, between about 0 to about 0.6M, between about 0 to about 0.5M, between about 0 to about 0.4M, between about 0.05M to about 0.50M, between about 0.10M to about 0.45M, between about 0.10M to about 0.40M, between about 0.250 to about 0.5M, between about 0 to about 0.075M, between about 0.250 to about 0.5M, between about 0.075 to about 0.5M, or between about 0.15M to about 0.40M. In some embodiments, the mobile phase includes a salt concentration of approximately 0.01M, 0.02M, 0.03M, 0.04M, 0.05M, 0.06M, 0.07M, 0.08M, 0.09M, 0.1M, 0.2M, 0.3M, 0.4M, 0.5M, 0.6M, 0.7M, 0.8M, 0.9M, or 1.0M. In some embodiments, the salt concentration in the mobile phase is a gradient (e.g., linear or non-linear gradient). In some embodiments, the salt concentration in the mobile phase is constant. In some embodiments, the salt concentration in the mobile phase may increase or decrease stepwise.

Typically, the mobile phase is buffered. In certain embodiments, the mobile phase is not buffered. In certain embodiments, the mobile phase is buffered to a pH between about 5 to about 14. In certain embodiments, the mobile phase is buffered to a pH between about 5 to about 10. In certain embodiments, the mobile phase is buffered to a pH between about 6 to about 8. In certain embodiments, the mobile phase is buffered to a pH of about 7.5. In certain embodiments, the mobile phase is buffered to a pH of about 7.0. In certain embodiments, the mobile phase is buffered to a pH of about 6.0, 6.5, 7.0, 7.5, or 8.0.

In some embodiments, an impure preparation or an intermediate eluate or flow-through is adjusted to conductivity ranging between about 1 mS/cm and 20 mS/cm (e.g., between about 1 mS/cm and 15 mS/cm, between about 1 mS/cm and 10 mS/cm, between about 1 mS/cm and 8 mS/cm, between about 1 mS/cm and 6 mS/cm, between about 1 mS/cm and 4 mS/cm, between about 2 mS/cm and 4 mS/cm) prior to loading in the cation-exchange chromatography column (e.g., SP column or YMC-BioPro S30 column). In particular embodiments, an impure preparation or an intermediate eluate or flow-through is adjusted to conductivity ranging between about 2 mS/cm and 4 mS/cm (e.g., 2, 2.5, 3, 3.5, or 4 mS/cm) prior to loading in the cation-exchange chromatography column (e.g., SP column or YMC-BioPro S30 column). The conductivity may be adjusted by diluting an impure preparation or an intermediate eluate or flow-through with $H_2O$ at, e.g., 1:1, 1.1:1, 1.2:1, 1.3:1, 1.4:1, 1.5:1, 2.0:1, 2.5:1, 3.0:1, 4.0:1, 5.0:1, or 10:1 ratio. The conductivity may also be adjusted by diafiltration into a desired buffer. In some embodiments, a cation-exchange chromatography column is run at a pH of about 6.5-8.0 (e.g., about 6.5, 7.0, 7.5 or 8.0). In some embodiments, a suitable pH is about 7.0-7.5 (e.g., about 7.0, 7.1, 7.2, 7.3, 7.4 or 7.5).

In some embodiments, prior to loading, the column may be equilibrated. In some embodiments, the equilibration occurs in one or more steps (e.g., 1, 2 or 3 steps). In some embodiments, each equilibration step uses a different buffer. In some embodiments, the equilibration is performed with one or more column volumes per step (e.g., 1, 2, 3, 4 or 5 CV).

In some embodiments, prior to loading a bulk sample comprising C3 fusion protein onto a chromatography column, the cell lysate is clarified. In some embodiments, the cell lysate is clarified and loaded onto a cation exchange column. In certain embodiments, the clarified cell lysate is generated by TFF, which results in TFF permeate. In some embodiments, the TFF permeate containing C3 fusion protein may be conditioned to an optimal conductivity between 7 and 9 mS/cm (e.g., 7.5±0.5 mS/cm) with a dilution buffer prior to loading on the cation exchange column. In some embodiments, the dilution buffer is a HEPES buffer. In certain embodiments, HEPES is present in the dilution buffer at a concentration between 10-100 mM. In certain embodiments, HEPES is present in the dilution buffer at a concentration of 20 mM. In some embodiments, the dilution buffer further comprises EDTA. In certain embodiments, EDTA is present in the dilution buffer at a concentration ranging from 0.1-10 mM, 0.1-5 mM, 1-5 mM (e.g., 1, 2, 3, 4, 5), 0.1-0.60 mM (e.g., 0.1. 0.2, 0.3, 0.4, 0.5, 0.6).

In further embodiments, to capture the C3 fusion proteins from most host-cell derived impurities, a cation exchange resin (e.g., SP Sepharose XL) column may be equilibrated with at least two column volumes (CV) of equilibration buffer. In some embodiments, the equilibration buffer comprises 40-50 mM HEPES, 50-250 mM NaCl, 0.3-0.5 mM EDTA, pH 7.0-8.0.

In some embodiments, the conditioned permeate containing the C3 fusion is loaded onto the capture column comprising the cation exchange resin (e.g., SP Sepharose XL), washed and then eluted in a single step with one or more CV of elution buffer (e.g., 1 CV, 2 CV, 3 CV, 4 CV, 5 CV, 6 CV). In some embodiments, the elution buffer comprises 40-50 mM HEPES, 75-250 mM NaCl, 0.3-0.5 mM EDTA, at pH 7-8.0. In some embodiments the peak eluate may be collected. In particular embodiments, the collection of the C3 fusion protein product begins when the ascending elution peak reaches an absorbance of 500 mAU and continues until the absorbance drops on the tailing edge of the peak to 500 mAU (peak eluate).

In some embodiments, column buffers may be a sodium phosphate buffer (e.g., 20-50 mM $NaH_2PO_4$). In some embodiments the buffer further comprises 0-500 mM NaCl, 20-30 mM citric acid, 0.3-0.5 mM EDTA, pH 7.0. After loading, the column may be washed with one or more column volumes of buffer. In some embodiments, the wash buffer may be the same as the equilibration buffer. In some embodiments, the recombinant C3 fusion protein is eluted using an elution buffer. Protein elution may be performed be performed using a linear gradient method, a stepwise gradient method, a combination of gradient and stepwise elution method, or an isocratic solution method. The gradient can be increasing or decreasing salt (e.g., NaCl) or pH. In certain embodiments, the elution is performed with a linear gradient method. In particular embodiments, the gradient may be started with 5% elution buffer and continued for 7 CV, at 5% elution buffer per CV, until 40% elution buffer is reached.

Hydrophobic Interaction Chromatography

Hydrophobic Interaction Chromatography (HIC) is a separation technique that uses the properties of hydrophobicity to separate proteins from one another. In this type of chromatography, hydrophobic groups such as phenyl, octyl, or butyl, are attached to the stationary column. Proteins that pass through the column that have hydrophobic amino acid side chains on their surfaces are able to interact with and bind to the hydrophobic groups on the column. HIC columns are known, and include for example, Butyl Sepharose. Various bed height for a HIC column may be used. In some embodiments, a suitable HIC column has a bed height of 5 cm-30 cm. In particular embodiments, a suitable HIC column has a bed height of 5 cm, 10 cm, 15 cm, 20 cm, 25 cm, or 30 cm.

HIC separations are often designed using the opposite conditions of those used in ion exchange chromatography. In general, a buffer with a high ionic strength, usually ammonium sulfate, is initially applied to the column. The salt in the buffer reduces the solvation of sample solutes thus as solvation decreases, hydrophobic regions that become exposed are adsorbed by the medium. The stationary phase is generally designed to form hydrophobic interactions with other molecules. These interactions are generally too weak in water, however, addition of salts (e.g., $Na_2SO_4$, $K_2SO_4$, $(NH_4)_2SO_4$, NaCl, $NH_4Cl$, NaBr, and NaSCN) to the buffer results in hydrophobic interactions. In some embodiments, the mobile phase includes a salt concentration between about 0.1M to about 3.0M, e.g., between about 0.1M to about 1.6M, between about 0.2M to about 1M, or between about 0.3M to about 0.75M.

In certain embodiments, the mobile phase is buffered. In certain embodiments, the mobile phase is not buffered. In certain embodiments, the mobile phase is buffered to a pH between about 6 to about 8. In certain embodiments, the mobile phase is buffered to a pH between about 6.5 to about 7.5. In certain embodiments, the mobile phase is buffered to a pH of about 7.5. In certain embodiments, the mobile phase is buffered to a pH of about 7.5.

In some embodiments, an impure preparation or an intermediate eluate or flow-through is adjusted to salt (e.g., $(NH_4)_2SO_4$) concentration ranging from about 0.5 M to about 2.0 M (e.g., about 0.5 M, 1.0 M, 1.1 M, 1.2 M, 1.3 M, 1.4 M, 1.5 M, 1.6 M, 1.7 M, 1.8 M, 1.9 M, or 2.0 M) at pH of about 6.0-8.0 (e.g., about 6.0, 6.5, 7.0, 7.3, or 7.5), prior to loading onto the hydrophobic interaction chromatography column (e.g., butyl column). Once loaded, a hydrophobic interaction chromatography column may be washed using a wash buffer comprising salt (e.g., $(NH_4)_2SO_4$) concentration ranging from about 0.5 M to about 2.0 M (e.g., about 0.5 M, 0.75M, 1.0 M, 1.1 M, 1.2 M, 1.3 M, 1.4 M, 1.5 M, 1.6 M, 1.7 M, 1.8 M, 1.9 M, or 2.0 M) at pH of about 6.0-8.0 (e.g., about 6.0, 6.5, 7.0, 7.3, or 7.5). In some embodiments, the hydrophobic interaction chromatography column is eluted using a elution buffer comprising salt (e.g., $(NH_4)_2SO_4$) concentration ranging from about 0.1 M to about 0.75 M (e.g., about 0.3 M, 0.4 M, 0.5 M, 0.6 M, 0.7 M or 0.75M) at pH of about 6.0-8.0 (e.g., about 6.0, 6.5, 7.0, 7.3, or 7.5).

Ultrafiltration/Diafiltration

In some embodiments, the purification methods disclosed herein include one or more steps of ultrafiltration/diafiltration. Ultrafiltration/diafiltration, as used herein, refers to membrane filtration with filter pore sizes on the magnitude of 0.001 and 0.1 μm, which may be used for concentrating and desalting dissolved molecules (proteins, peptides, nucleic acids, carbohydrates, and other biomolecules), exchanging buffers, and gross fractionation. Methods of ultrafiltration for use in embodiments of the invention include tangential flow ultrafiltration or crossflow filtration.

Tangential flow filtration and ultrafiltration, as used herein, refers to arrangements where the feed stream passes parallel to the membrane face as one portion passes through the membrane (permeate) while the remainder (retentate) is recirculated back to the feed reservoir. In some embodiments, pore size of tangential flow ultrafiltration filters is chosen to allow recombinant C3 fusion protein to permeate through the filter. In other embodiments, pore size is chosen so as to retain substantially all C3 fusion protein in the feed passing across the filter. As noted elsewhere, C3 fusion protein is approximately 25.7 kD. Using SDS-PAGE analysis, exemplary C3 fusion protein major band migrates between 21 and 31 kDa. The pH of the feed may be adjusted in combination with selection of appropriate pore size to either retain C3 fusion protein on the filter membrane or allow it to pass through as a permeate.

In some embodiments, supernatant may be clarified by a Tangential Flow Filtration (TFF) system. In some embodiments, the TFF system is equipped flat sheet membrane or a hollow fiber membrane (e.g., modified Polyethersulfone (mPES), Mixed Cellulose Ester (ME), Polysulfone (PS) and Polyethersulphone (PES)). In certain embodiments, the TFF system is equipped with a Sartorius Sartocon slice membrane (1000 kDa, 0.5 m²). The filtration may be performed in two steps: a concentration phase and a diafiltration phase. Within the diafiltration phase, the retentate may be continuously washed. In some embodiments, the retentate is continuously washed with up to 5.0 column volumes, (CV) (e.g., 1 CV, 2CV, 3, CV, 4, CV, 5 CV) volumes of diafiltration buffer. In some embodiments the diafiltration buffer is a HEPES buffer. In certain embodiments, HEPES is present in the diafiltration buffer at a concentration between 10-100 mM. In some embodiments, the diafiltration buffer further comprises EDTA. In certain embodiments, EDTA is present in the diafiltration buffer at a concentration between 50-150 mM.

Pore size may be selected with molecular weight cutoffs of at least 5 kDa, at least 10 kDa, at least 20 kDa, at least 30 kDa, at least 40 kDa, at least 50 kDa, at least 60 kDa, at least 70 kDa, at least 80 kDa, at least 90 kDa, at least 100 kDa, at least 200 kDa, at least 300 kDa, at least 400 kDa, at least 500 kDa, 600 kDa, 700 kDa, 800 kDa, 900 kDa, 1000 kDa, or at least 1500 kDa. For example, a filter with a pore size of at least 5 kDa will retain in the feed a majority of proteins with molecular weights higher than approximately 5 kDa. As another example, a filter of a pore size of at least 400 kDa will retain a majority of proteins with molecular weights higher than 400 kDa. In some embodiments, the feed retention rate is at least 75%, at least 80%, at least 85%, at least 90%, at least 95%, or higher. Likewise, pore size may be selected for isolation of permeates of particular size. For example, a filter with a pore size of at least 500 kDa will allow a majority of proteins with molecular weights less than 500 kDa to permeate through. In some embodiments, the permeation rate is at least 75%, at least 80%, at least 85%, at least 90%, at least 95% or higher.

Filtration area or capacity may also be optimized for use in the processes disclosed herein. Considerations impacting selection of filtration area include robustness, cost, feed flow rate (i.e., crossflow velocity), transmembrane pressure, permeate flux rate, plant fit and throughput. In some embodiments, the permeate flux is about 50-100 liter per meter per hour ("LMH"). In some embodiments, the feed flow is about 250-600 LMH, inclusive. In some embodiments, the feed flow is about 250-350 LMH, inclusive. In some embodiments, the feed flow is about 175-245 LMH, inclusive. In some embodiments, the feed flow is about 170-230 LMH, inclusive. In some embodiments, the feed flow is about 120-160 LMH, inclusive. In some embodiments, the feed flow is about 15-30 LMH, inclusive. In some embodiments, the fee flow is about 11-21 LMH, inclusive. In some embodiments, the filtration area is about 0.02 m², about 0.14 m², about 0.7 m², or about 3.5 m². In particular embodiments, the transmembrane pressure is about 55-60 psi, inclusive. In some embodiments, the transmembrane pressure is about 15-25 psi, inclusive. In some embodiments, the transmembrane pressure is about 10-20 psi, inclusive. In some embodiments, the transmembrane pressure is about 5-15 psi, inclusive.

Ultrafiltration filters for use in embodiments of the invention may comprise membrane materials known to those of skill in the art, including but not limited to polyethersulfone and stabilized cellulose. One exemplary filter cassette for use in embodiments of the invention is the Pellicon 3 Ultracell 5 kDa MWCO. In some embodiments, the filter is preconditioned with buffer before concentration and/or diafiltration. In some embodiments, the conditioning or diafiltration buffer comprises $NaH_2PO_4$. In some embodiments, the $NaH_2PO_4$ is present at a concentration ranging from 5 mM to 50 mM.

Membrane Adsorption

Generally, membrane adsorbers are thin, synthetic, microporous or macroporous membranes that are derivatized with functional groups akin to those on the equivalent resins. The membranes are stacked 10-15 layers deep in a comparatively small cartridge, allowing for increased flow rate and speed in purification in processing. Adsorption is efficient because the transport of solutes to their binding sites in a membrane adsorber occurs mainly by convection, while pore diffusion (the predominant mechanism in resins) is minimal. Membrane adsorbers are capable of linear scale-up for parameters such as frontal surface area, bed volume, flow rate, and static binding capacity.

Exemplary membrane adsorbers include the Sartobind® membrane adsorbers (MA) for ion exchange chromatography. The Sartobind® membrane displays a microporous structure with pore size of >3 Ligands for ion exchange are bound covalently to the complete internal surface of the membrane, resulting in separation media of high binding capacity combined with very high flow rates. Binding of ion exchange ligands is very stable and allows many cycles of re-use without loss of binding capacity. Sartobind® MA units for ion exchange are available as strong or weak anion (Q and D) and strong cation (S) type. Sartobind® MA units are equipped with standard Luer Lock connectors and can be run with high-performance liquid chromatography (HPLC) or fast protein liquid chromatography (FPLC) systems or by hand with a syringe.

In some embodiments, Sartobind® Q membrane adsorbers display a macro-porous structure with pore size of >3 Quaternary ammonium ligands are bound covalently to the complete internal surface of the membrane, resulting in separation media of high binding capacity combined with exceptionally high flow rates. In some embodiments, Sartobind Q membrane may be used for the flow-through polishing of purified proteins (e.g., C3 fusion protein). The bed volumes can be kept sufficiently small during the removal of viruses, DNA, host cell proteins, leached Protein A, and endotoxins from such pharmaceutical proteins.

Purified C3 Fusion Protein Composition

Composition Comprising C3 Fusion Protein

Purified recombinant C3 fusion protein may be characterized using various methods. In some embodiments, stability indicating methods (e.g., SDS-PAGE, SE-HPLC, SEC-UV, RP-HPLC, IEX-HPLC, and LC-MS) may be used to assess the protein purity. According to the present invention, circular dichroism (CD) can be used for secondary structure, and differential scanning calorimetry (DSC) for tertiary structure analysis. The bioactivity may be assessed by a functional assays such as GH-Assay and/or ADP-ribosylation activity.

In some embodiments, a C3 fusion protein comprising SEQ ID NO: 1 is a recombinant protein composed of 231 amino acids with a theoretical molecular weight of 25,726 daltons (in some embodiments, a nominal molecular weight of 26-28 kDa is used for analytical purposes) and theoretical isoelectric point (pI) of 9.6. The extinction coefficient has been determined by amino acid analysis to be 0.72 units of absorbance at $A_{280\ nm}$ per mg of protein.

In certain embodiments, upon expression and purification of the coding region comprising SEQ ID NO: 3, according to the present invention, the N-terminal methionine is absent as determined by mass spectrometry in peptides or peptides derived or related to C3 fusion polypeptides. Peptide mapping providing 97%-100% coverage can be used to confirm the theoretical protein sequence without an N-terminal methionine, and the amino acid sequence results correspond with those expected the theoretical sequence.

In some embodiments, a C3 fusion protein composition comprises a population of C3 fusion polypeptides. In some embodiments, a purified C3 fusion protein composition comprises a population of C3 fusion polypeptide, each having an amino acid sequence described herein, wherein the first amino acid of each polypeptide is not a methionine and wherein the population of the polypeptides constitutes greater than 70%, 75%, 80%, 85%, 90%, 92%, 94%, 95%, 96%, 97%, 98%, 99% of the total amount of polypeptides in the composition. In some embodiments, a purified C3 fusion protein composition comprises a C3 fusion protein that does not comprise a methionine as the first amino acid.

In some embodiments, a purified C3 fusion protein composition comprises a population of C3 fusion polypeptide that comprising a first polypeptide and a second polypeptide, each having an identical amino acid sequence described herein except wherein the first polypeptide does not contain a methionine at the N-terminus. In some embodiments, the weight ratio of the first polypeptide to the second polypeptide is at least 6:1, 7:1, 8:1, 9:1, 10:1, 12:1, 15:1, 20:1, 50:1, or 100:1.

The protein concentration of a purified C3 fusion protein composition may be determined by any suitable method known in the art for determining protein concentrations. In some embodiments, the protein concentration is determined by an ultraviolet light absorbance assay. In some embodiments, such absorbance assays are typically conducted at about a 280 nm wavelength ($A_{280}$). In some embodiments, a C3 fusion protein composition may comprise C3 fusion protein at a high concentration (e.g., greater than about 8 mg/ml, 9 mg/ml, 10 mg/ml, 13 mg/ml, 15 mg/ml, 19 mg/ml, 20 mg/ml, 25 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml or more). In some embodiments, a C3 fusion protein composition comprises a purified C3 fusion protein at a concentration ranging from about 0.1 mg/ml to about 50 mg/ml, about 1 mg/ml to about 40 mg/ml, about 5 mg/ml to about 40 mg/ml, about 8 mg/ml to about 40 mg/ml, about 10 mg/ml to about 40 mg/ml, about 13 mg/ml to about 40 mg/ml, about 15 mg/ml to about 40 mg/ml, about 19 mg/ml to about 40 mg/ml, about 25 mg/ml to about 40 mg/ml, about 25 mg/ml to about 35 mg/ml, about 26 mg/ml to about 34 mg/ml, about 27 mg/ml to about 33 mg/ml, about 30 mg/ml to about 40 mg/ml, about 31 mg/ml to about 38 mg/ml, about 31 mg/ml to about 37 mg/ml, about 33 mg/ml to about 40 mg/ml, about 37 mg/ml to about 40 mg/ml, about 10 mg/ml to about 38 mg/ml, about 10 mg/ml to about 35 mg/ml, about 10 mg/ml to about 30 mg/ml, about 10 mg/ml to about 25 mg/ml, about 10 mg/ml to about 20 mg/ml, about 10 mg/ml to about 15 mg/ml. In some embodiments, a purified C3 fusion protein composition comprises a C3 fusion protein at a concentration of about 1 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml or 37 mg/ml.

Purity

The purity of a purified C3 fusion protein composition is typically measured by the percentage of the target C3 fusion protein in the total amount of purified composition using various assays. In some embodiments, the purity of a purified recombinant C3 fusion protein composition is measured by the level of various impurities (e.g., host cell protein or host cell DNA) present in the purified composition including final product. In some embodiments, the level of host cell protein (HCP) is measured by Host Cell Proteins Immunoassay (such as ELISA), SDS-PAGE, or size-exclusion chromatography. In some embodiments, ELISA assays are used to quantify the level of HCP in a purified C3 fusion protein composition. In some embodiments, various antibodies against host cell proteins may be used including those commercially available antibodies against host cell proteins from various cell types (e.g., bacterial cells such as E. coli, mammalian cells such as human cells, CHO cells, or others). In some embodiments, the purified recombinant C3 fusion protein composition contains less than 150 ng HCP/mg C3 fusion protein (e.g., less than 140, 130, 120, 110, 100, 90, 80, 70, 60, 50, 40, 30, 30, 20, 10 ng HCP/mg C3 fusion protein). Various assays may be used to measure the level of host cell DNA in a purified C3 fusion protein composition. In some embodiments, the purified recombinant C3 fusion protein composition contains less than about 150 pg/mg, 140 pg/mg, 130 pg/mg, 120 pg/mg, 110 pg/mg, 100 pg/mg, 90 pg/mg, 80 pg/mg, 70 pg/mg, 60 pg/mg, 50 pg/mg, 40 pg/mg, 30 pg/mg, 20 pg/mg, or 10 pg/mg Host Cell DNA.

In some embodiments, the purified recombinant C3 fusion protein composition, when subject to SDS-PAGE with Coomassie Brilliant Blue staining, has no new bands with intensity greater than the 0.05%, 0.01%, 0.15%, 0.2%, 0.25%, 0.3%, 0.35%, 0.4%, 0.45%, or 0.5% assay control. In some embodiments, the purified recombinant C3 fusion protein composition, when subject to SDS-PAGE with Western blotting against HCP, has no bands with intensity greater than the 15 kDa HCP band assay control, and no new bands with intensity greater than the 0.05%, 0.01%, 0.15%, 0.2%, 0.25%, 0.3%, 0.35%, 0.4%, 0.45%, 0.5%, or 1.0% assay control. In some embodiments, the purified recombinant C3 fusion protein composition, when subject to SDS-PAGE with silver staining, has no new bands with intensity greater than the 0.05%, 0.01%, 0.15%, 0.2%, 0.25%, 0.3%, 0.35%, 0.4%, 0.45%, or 0.5% assay control. In some embodiments, the host cell protein (HCP) log reduction value (LRV) is between about 0.3 and about 0.6, e.g., between about 0.4 and 0.5. Various assay controls may be used, in particular, those acceptable to regulatory agencies such as FDA.

The purity of a purified recombinant C3 fusion protein composition may also be determined by one or more of size exclusion chromatography-high performance liquid chromatography (SEC-HPLC), capillary electrophoresis-SDS PAGE (CE-SDS PAGE), ion-exchange high performance liquid chromatography (IE-HPLC) and/or reverse phase-high performance liquid chromatography (RP-HPLC). In some embodiments, the purity of a purified C3 fusion protein composition is represented by the percentage of the major peak in the chromatogram that corresponds to the major species of C3 fusion protein. In some embodiments, the purity of a purified C3 fusion protein composition is characterized by percentages of different peaks indicative of different species of C3 fusion protein present in the purified composition. In some embodiments, the purity of a purified C3 fusion protein composition is measured by the percentage of total impurities present in the composition. Parameters that may be altered or optimized to increase resolution include gradient conditions, organic modifier, counter ion, temperature, column pore size and particle size, solvent composition and flow rate. Purity levels may be discerned by peak percentages, as known to those of skill in the art. For example, purity may be determined by integrating the main and side peaks observed and calculating the main peak's percentage of the total area.

In some embodiments, the purity of a purified C3 fusion protein composition is determined by SEC-HPLC. In some embodiments, the purity of a C3 fusion protein composition purified by the methods disclosed herein is determined by SEC-HPLC. In some embodiments, the purity of C3 fusion protein composition is measured by the main peak percentage of SEC-HPLC and is greater than or equal to about 90%, about 95%, about 96%, about 97%, about 98%, about 99% or higher. The main peak of SEC-HPLC represents the monomers of C3 fusion protein. In some embodiments, the purity of a C3 fusion protein composition is indicated by the percentage of total impurities measured by SEC-HPLC. In some embodiments, the total impurities measured by SEC-HPLC is less than or equal to about 10%, about 8%, about 6%, about 5%, about 4%, about 3%, about 2%, about 1%, about 0.5%, about 0.1% or less.

In some embodiments, the purity of a C3 fusion protein composition purified by the methods disclosed herein is determined by RP-HPLC. In some embodiments, the purity of C3 fusion protein composition is measured by the main peak percentage of RP-HPLC and is greater than or equal to about 80%, about 85%, about 90%, about 95%, about 96%, about 97%, about 98%, about 99% or higher. In some embodiments, the purity of a C3 fusion protein composition is indicated by the percentage of total impurities measured by RP-HPLC. In some embodiments, the total impurities measured by RP-HPLC is less than or equal to about 20%, about 18%, about 15%, about 10%, about 8%, about 6%, about 5%, about 4%, about 3%, about 2%, about 1%, about 0.5%, about 0.1% or less.

In some embodiments, the purity of a C3 fusion protein composition purified by the methods disclosed herein is determined by IE-HPLC (also known as IEX-HPLC). In some embodiments of the invention, the purity of C3 fusion protein is determined by main peak percentage of IE-HPLC and is greater than or equal to about 80%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or higher. The major peak of IE-HPLC is indicative of the main species of C3 fusion protein which represents the main product of C3 fusion protein with a specific charge profile. In some embodiments, the purity of a C3 fusion protein composition can also be determined by percentages of side peaks of IE-HPLC. Typical side peaks of IE-HPLC include, but not limited to, acidic peaks and basic peaks. In some embodiments, the percentage of total acidic peaks is less than or equal to about 15%, about 12%, about 11%, about 10%, about 8%, about 6%, about 5%, about 4%, about 3%, about 2%, about 1%, about 0.5%, about 0.1% or less. In some embodiments, the percentage of total basic peaks is less than or equal to about 10%, about 8%, about 6%, about 5%, about 4%, about 3%, about 2%, about 1%, about 0.5%, about 0.1% or less. In some embodiments, the purified C3 fusion protein composition comprises greater than 83% main peak of IE-HPLC. In some embodiments, the purified C3 fusion protein composition comprises greater than 85% main peak of IE-HPLC, less than 10% total acidic peaks and less than 5% total basic peaks.

Glycohydrolase (GH) Activity Assay

The intracellular action of C3 exoenzymes and C3 fusion proteins results from transfer of an ADP-ribose moiety to an asparagine residue in Rho GTPase, trapping this GTPase in its inactive conformation. An exemplary C3 fusion protein is an ADP-ribosyltransferase that catalyzes hydrolysis of NAD in the absence of the specific protein substrate, Rho. C3 fusion protein catalyzes transfer of an ADP-ribose moiety to the RhoA, RhoB and RhoC members of the Rho family of small GTPases. In neurons, the predominant species is RhoA, so the numbering system for RhoA and the abbreviation "Rho" is used. A spectrofluorometric glycohydrolase (GH) activity assay was used to measure glycohydrolase (GH) as the formation of a fluorescent product, which gives a sensitive and reliable method to serve as a test of identity and potency.

The GH assay measures the formation of ε-ADP-ribose produced as a result of hydrolysis of ε-NAD by C3-variants.

Glycohydrolase activity of C3-variants converts ε-NAD$^+$ into ε-ADP-ribose, a molecule with 10 times higher fluorescence intensity at the selected wavelengths. The fluorescence intensity of ε-ADP-ribose is used to measure the amount of ε-ADP ribose formed by using a standard curve of fluorescence of known concentrations of ε-AMP. The fluorescence intensities of ε-AMP and ε-ADP-ribose are measured by exciting the reaction at 305 nm and recording the emission at 410 nm. A unit of activity is defined as nmoles ADP-ribose formed in 30 minutes at 37° C. In some embodiments, the purified C3 fusion protein has the activity to form about 5-60 nmol, about 10-50 nmol, or about 20-40 nmol of ADP-ribose per mg protein in 30 minutes at 37° C. The assay is linear with up to at least 12 μg of C3-variant protein and up to least 180 minutes of incubation time. This assay has been found to be precise, accurate and reproducible. This assay has also been found to be useful in measuring decreases in enzymatic activity after incubation at 70° C., and can be considered to be stability-indicating when used in a well-designed stability study.

Other Attributes

Other attributes of the purified C3 fusion protein composition according to the present invention are characterized including, but not limited to, appearance, pH, molecular weight, the endotoxin level, osmolality, sterility, subvisible particulate matter, sub 10 μm particulate matter, and/or container closure integrity (or dye immersion test). In some embodiments, a purified C3 fusion protein according to the present invention has an appearance of a clear, colorless liquid, substantially free of visible particulates. In some embodiments, a purified C3 fusion protein according to the present invention has a pH of about 5.5-8.0, about 5.8-7.8, about 6.0-7.5, about 6.0-7.2, or about 6.0-7.0. In some embodiments, a purified C3 fusion protein according to the present invention has a major band with a molecular weight of 21-31 kDa when measured by SDS-PAGE with Coomassie blue staining. In some embodiments, a purified C3 fusion protein according to the present invention contains an endotoxin (LAL) level of less than or equal to about 1 EU/mg, about 0.8 EU/mg, about 0.6 EU/mg, about 0.5 EU/mg, about 0.1 EU/mg, or less. In some embodiments, a purified C3 fusion protein according to the present invention contains subvisible particulate matter less than or equal to about 6000 (e.g., less than or equal to about 5000, about 4000, about 3000, about 2000, about 1000, about 800, about 700, about 600, about 500, or less) NMT with ≥10 μm per container, and/or subvisible particulate matter less than or equal to about 800 (e.g., less than or equal to about 700, about 600, about 500, about 400, about 300, about 200, about 100, or less) NMT with ≥25 μm per container. In some embodiments, no dye detected in the purified C3 fusion protein according to the present invention when tested in dye immersion test for container closure integrity.

Pharmaceutical Compositions

A recombinant C3 fusion protein or a pharmaceutical composition containing the same can be formulated with a physiologically acceptable carrier or excipient to prepare a pharmaceutical composition. The carrier and therapeutic agent can be sterile. The formulation should suit the mode of administration.

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interfere with their activity.

The composition or medicament, if desired, can also contain minor amounts of wetting or emulsifying agents, or pH buffering agents. The composition can be a liquid solution, suspension, emulsion, sustained release formulation, or powder. The composition or medicament can be formulated in accordance with routine procedures as a pharmaceutical composition adapted for administration to human beings. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent.

In some embodiments, the C3 fusion protein pharmaceutical composition further comprises fibrinogen and does not contain thrombin. In some embodiments, the C3 fusion protein pharmaceutical composition further comprises albumin, one or more blood coagulation factors, globulin, and/or one or more plasminogen-activator inhibitors or plasmin inhibitors. In some embodiments, the C3 fusion protein the pharmaceutical composition comprises aprotinin. In some embodiments, the C3 fusion protein pharmaceutical composition further comprises thrombin. In some embodiments, the C3 fusion protein pharmaceutical composition is a tissue adhesive.

In some embodiments, the C3 fusion protein pharmaceutical composition may promote neuroregeneration and neuroprotection. In some embodiments, the C3 fusion protein pharmaceutical composition may be used in a method to treat CNS trauma. In some embodiments, CNS trauma occurs in the form of spinal cord injury, for example, resulting in the loss of axons and the subsequent inability of axons to regrow and find appropriate targets. In some embodiments, spinal cord injury may result in immediate tear of axons. In some embodiments, spinal cord trauma may cause axons to deteriorate due to the disruption of vital transport of molecules and cell components to and from the ends of axons. In some embodiments, CNS trauma comprises traumatic brain injury. In some embodiments, CNS trauma comprises stroke.

In some embodiments, the C3 fusion protein pharmaceutical composition may be used to facilitating axon growth or tissue repair (e.g., repair of a central nervous system (CNS) lesion site or a peripheral nervous system (PNS) lesion site). Treatment with pharmaceutical compositions according to the present invention can be used to enhance the rate of axon growth of peripheral nerves and thereby be effective for repair of peripheral nerves after surgery, for example after reattaching severed limbs. Also, treatment with pharmaceutical compositions according to the present invention may be effective for the treatment of various peripheral neuropathies because of their axon growth promoting effects.

Therapeutic Uses

A pharmaceutical composition based on a C3 fusion protein described herein may be used for various therapeutic purposes. In particular, the present invention pertains to the field of mammalian nervous system repair (e.g., repair of a central nervous system (CNS) lesion site or a peripheral nervous system (PNS) lesion site). The methods described herein may be extended to use in many other diseases including, but not limited to, cancer, metastasis, hypertension, cardiac disease, stroke, diabetic neuropathy, and neurodegenerative disorders such as stroke, Alzheimer's disease, Parkinson's disease, and amyotrophic lateral sclerosis (ALS). Treatment with therapeutic compositions according to the present invention can be used to enhance the rate of axon growth of peripheral nerves and thereby be effective for repair of peripheral nerves after surgery, for example after reattaching severed limbs. Also, treatment with therapeutic compositions according to the present invention is expected to be effective for the treatment of various peripheral neuropathies because of their axon growth promoting effects.

Spinal Cord Injury

As used herein, the term "spinal cord injury site" refers to a site of traumatic nerve injury or nerve injury caused by disease. The spinal cord injury site may be a single nerve (e.g., sciatic nerve) or a nerve tract comprised of many nerves (e.g., damaged region of the spinal cord). The spinal cord injury site may be in the central nervous system or peripheral nervous system or in any region needing repair. The spinal injury site may form as a result of damage caused by stroke.

Spinal cord injuries result from damage to the vertebrae, ligaments or disks of the spinal column or to damage to the spinal cord itself. In some embodiments, a spinal cord injury is a traumatic injury. In some embodiments, a spinal cord injury is a nontraumatic injury. A traumatic spinal cord injury may stem from a sudden, traumatic blow to the spine that fractures, dislocates, crushes, or compresses one or more vertebrae. It also may result from a gunshot or knife wound that penetrates and cuts the spinal cord. Common causes of traumatic spinal cord injury include motor vehicle accidents, falls, acts of violence and sports and recreation injuries. Additional damage usually occurs over days or weeks because of bleeding, swelling, inflammation and fluid accumulation in and around the spinal cord. A nontraumatic spinal cord injury may be caused by arthritis, cancer, inflammation, infections or disk degeneration of the spine.

Symptoms of spinal cord injury depend on two factors: the location of the spinal cord injury along the spinal cord and the severity of the injury. The lowest part of the spinal cord that functions normally after spinal cord injury is referred to as the neurological level of the injury. The severity of the injury is often called the "completeness" is often classified as either complete or incomplete. A spinal cord injury is complete if almost all feeling (sensation) and all ability to control movement (motor function) are lost below the spinal cord injury. A spinal cord injury is incomplete if some motor or sensory function exists below the level of the spinal cord injury. There are varying degrees of incomplete injury. Paralysis from a spinal cord injury may be referred to as tetraplegia (quadriplegia) or paraplegia. Tetraplegia means that the arms, hands, trunk, legs, and pelvic organs are all affected by the spinal cord injury. Paraplegia means that all or part of the trunk, legs and pelvic organs are affected by the spinal cord injury.

Spinal cord injuries may result in one or more of the following signs and symptoms: loss of movement, loss of sensation, including the ability to feel heat, cold and touch, loss of bowel or bladder control, exaggerated reflex activities or spasms, changes in sexual function, sexual sensitivity and fertility, pain or an intense stinging sensation caused by damage to the nerve fibers in the spinal cord, difficulty breathing, coughing or clearing secretions from the lungs.

In some embodiments, the present invention provides methods to promote neuroregeneration and neuroprotection. In some embodiments, the present invention provides methods for treating CNS trauma. In some embodiments, CNS trauma occurs in the form of spinal cord injury, for example, resulting in the loss of axons and the subsequent inability of axons to regrow and find appropriate targets. In some embodiments, spinal cord injury may result in immediate tear of axons. In some embodiments, spinal cord trauma may cause axons to deteriorate due to the disruption of vital transport of molecules and cell components to and from the ends of axons. In some embodiments, CNS trauma comprises traumatic brain injury. In some embodiments, CNS trauma comprises stroke.

The Rho family of GTPases regulates axon growth and regeneration. Inactivation of Rho with a therapeutic protein as described above (e.g., a C3 transferase) can stimulate regeneration and sprouting of injured axons. See, for example, Saito et al., 1995, FEES Lett 371:105-109; Wilde et al 2000. J. Biol. Chem. 275:16478.

In one embodiment, in the present invention provides methods of treating spinal cord injury in a subject in need thereof. In some embodiments, spinal cord injury results from injury or disease. In some embodiments, spinal cord injury comprises injury to the cervical spinal cord. In some embodiments, spinal cord injury comprises injury to the thoracic spinal cord. In some embodiments, spinal cord injury comprises injury to the lumbar spinal cord. In some embodiments, spinal cord injury comprises injury to the sacral spinal cord. In some embodiments, spinal cord injury comprises incomplete spinal cord injury wherein the spinal cord is partially severed. In some embodiments, spinal cord injury comprises complete spinal cord injury, wherein the spinal cord is completely severed.

In one embodiment, the present invention provides methods of treating acute spinal cord injury in a subject in need thereof.

In one embodiment, the present invention provides methods of treating nerve injury or compression of a nerve in the peripheral nervous system, such as a nerve root that extends from the spinal cord such as a dorsal root (sensory nerve) or a motor root (motor nerve).

In other embodiments, the present invention provides method of treating peripheral nerve injury, such as may occur during brachial plexus injury where facilitating nerve growth is needed.

In some embodiments the present invention facilitates peripheral nerve injury. Peripheral nerve injury includes injury to peripheral nerves located in arms, hand, legs, feet or injury to a hand. In some instances peripheral nerve injury may occur after biopsy for diagnosis of neurological disease, such as removal of a segment of sural nerve.

In one embodiment, the present invention provides methods of facilitating axon growth in a subject in need thereof. In some embodiments facilitating axon growth comprises promoting axon growth. In some embodiments, facilitating axon growth comprises facilitating axon regeneration and/or regrowth. In some embodiments, axon growth according to the present invention occurs in the CNS. In some embodiments, axon growth according to the present invention occurs in the PNS.

In one embodiment, the present invention provides methods of repairing tissue in a subject in need thereof. In some embodiments, the tissue is neuronal tissue. In some embodiments, the tissue is in the CNS. In some embodiments, the tissue is in the PNS. In some embodiments, the tissue is non-neuronal tissue.

Therapeutic Proteins

An ADP-ribosyl transferase C3 protein described herein may be used to treat spinal cord injury or other CNS trauma. Various methods known in the art may be used to prepare and administer a therapeutic composition containing an ADP-ribosyl transferase C3 protein described herein.

In some embodiments, the present invention provides an improved method of preparing a therapeutic composition by mixing a therapeutically effective amount of an ADP-ribosyl transferase C3 protein with a fibrinogen composition that does not contain a thrombin to generate a therapeutic protein-fibrinogen composition; and combining the therapeutic protein-fibrinogen composition with a thrombin composition to generate a therapeutic composition. In some embodiments, a therapeutic composition prepared according to the present invention is a tissue adhesive that may be administered to a spinal cord injury site to facilitate axon growth.

In addition to the various C3 fusion protein described herein, other therapeutic protein may be prepared and administered using the improved methods described herein. For example, the improved methods described herein may be used to prepare and administer other inhibitors of Rho hyperactivation that can cause growth-inhibiting proteins to stop axons from regenerating. The methods described herein are particularly useful for preparing a therapeutic composition comprising a therapeutic protein containing a transport domain covalently linked to an amino acid sequence of an active domain (e.g., a purified C3 fusion protein).

Transport Domain

A transport domain comprises a peptide domain that can freely cross cell membranes. Several transport domains have been identified that allow a fused protein to efficiently cross cell membranes in a process known as protein transduction. Studies have demonstrated that a Tat (twin-arginine translocation) peptide derived from the HIV Tat protein has the ability to transduce peptides or proteins into various cells.

In some embodiments, the transport domain comprises a wild-type Tat peptide or antennapedia peptide, or a fragment or subdomain thereof, or a polypeptide derived therefrom. In some embodiments, the transport domain comprises a wild Tat peptide or antennapedia peptide. In some embodiments, the transport domain comprises a polypeptide having an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with a wild-type Tat peptide or antennapedia peptide. In some embodiments, the transport domain comprises a fragment or subdomain of Tat peptide or antennapedia peptide. In some embodiments, the transport domain comprises a polypeptide having an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with a fragment or subdomain of wild-type Tat peptide or antennapedia peptide. In some embodiments, the transport domain comprises a polypeptide derived from a nucleotide sequence encoding a wild-type Tat peptide or antennapedia peptide. In some embodiments, the transport domain comprises a polypeptide having an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with a polypeptide derived from a nucleotide sequence encoding a wild-type Tat peptide or antennapedia peptide.

In some embodiments, a Tat peptide or antennapedia peptide comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with a polypeptide selected from Table 1. In some embodiments, a Tat peptide or antennapedia peptide comprises an amino acid sequence selected from Table 1.

TABLE 1

| Transport Domain | Amino Acid Sequence | SEQ ID NO: |
|---|---|---|
| Antennapedia Leader Peptide (CT) | KKWKMRRNQFWVKVQRG | 15 |
| Antennapedia Peptide | RQIKIWFQNRRMKWKK | 16 |
| HIV-1 Tat (48-60) | GRKKRRQRRRPPQ | 17 |
| TAT (47-57) | YGRKKRRQRRR | 18 |
| Tat (48-57) | GRKKRRQRRR | 19 |
| Tat-Beclin-1 | YGRKKRRQRRRGGTNVFNAT FEIWHDGEFGT | 20 |
| Tat-C (48-57) | CGRKKRRQRRR | 21 |
| TAT-GluR23A Fusion Peptide | YGRKKRRQRRRAKEGANVAG | 22 |
| Tat-GluR23Y | YGRKKRRQRRRYKEGYNVYG | 23 |
| TAT-HA2 Fusion Peptide | RRRQRRKKRGGDIMGEWGNE IFGAIAGFLG | 24 |
| Tat-NR2Bct | YGRKKRRQRRRKLSSIESDV | 25 |
| TAT-NSF222 Fusion Peptide | YGRKKRRQRRR-GGG- LDKEFNSIFRRAFASRVFPPE | 26 |
| TAT-NSF700 Fusion Peptide | YGRKKRRQRRR-GGG-L LDYVPIGPRFSNLVLQALLVL | 27 |
| TAT-NSF700scr | YGRKKRRQRRRGGGIPPVYFS RLDLNLVVLLLAQL | 28 |

In some embodiments, a transport domain amino acid sequence is as follows:

(SEQ ID NO: 10)
EFVMNPANAQGRHTPGTRL

In some embodiments, a transport domain amino acid sequence is as follows:

(SEQ ID NO: 11)
EFVMNPANAQGR.

In some embodiments, a transport domain comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with SEQ ID NO: 10. In some embodiments, a transport domain comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with SEQ ID NO: 11.

Among other things, the present invention may be used to prepare and administer a C3 fusion protein containing an ADP-ribosyl transferase C3 domain and a transport domain described herein. In some embodiments, a C3 fusion protein comprises an amino acid sequence of a transport domain covalently linked to an amino acid sequence of an ADP-ribosyl transferase C3 domain, wherein the amino acid sequence of said transport domain is selected from a Tat peptide or antennapedia peptide, a fragment or subdomain of Tat peptide or antennapedia peptide, a polypeptide derived from a nucleotide sequence encoding a Tat peptide or antennapedia peptide, or a polypeptide having an amino acid sequence having at least 80% sequence identity thereto and wherein the amino acid sequence of the active domain of the C3 fusion protein is selected from an ADP-ribosyl transferase C3, a fragment thereof retaining ADP-ribosyl transferase activity, or an amino acid sequence having at least 80% sequence identity thereto. In some embodiments, the transport domain is a cell penetrating peptide or a fusogenic peptide. In certain embodiments, the transport domain is a proline-rich fusogenic peptide. In some embodiments, the transport domain is a highly basic, arginine-rich sequence corresponding to a reverse Tat sequence. Exemplary transport domains are described in Winton et al., 2002 J. Biol. Chem. 277:32820-32829, which is hereby incorporated by reference.

Active Domain

In accordance with the present invention, the active domain of a therapeutic protein may comprise a C3 transferase. C3 transferases cause the addition of one or more ADP-ribose moieties to Rho-like proteins. In some embodiments, the C3 transferase is from *Clostridium botulinum* (C3bot1 and 2). In some embodiments, the C3 transferase is from *Clostridium limosum* (C3lim). In some embodiments, the C3 transferase is from *Bacillus cereus* (C3cer). In some embodiments, the C3 transferase is from *Staphylococcus aureus* (C3stau1, 2 and 3).

In some embodiments, the active domain comprises an ADP-ribosyl transferase C3. In some embodiments, the active domain comprises a polypeptide having an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with an ADP-ribosyl transferase C3. In some embodiments, the active domain comprises a fragment of an ADP-ribosyl transferase C3 that retains ADP-ribosyl transferase activity. In some embodiments, the active domain comprises a polypeptide having an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with a fragment of an ADP-ribosyl transferase C3 that retains ADP-ribosyl transferase activity. In some embodiments, the active domain comprises the amino acid sequence of ADP-ribosyl transferases that act on Rho (Wilde et al. 2001. Biol. Chem. 275-16478-16483; Wilde et al 2001. J. Biol. Chem. 276:9537-9542).

In some embodiments, an active domain amino acid sequence is as follows:
Wild-Type C3 Transferase of *C. botulinum* (Swiss-Prot Entry P15879)

(SEQ ID NO: 12)
MKGLRKSILCLVLSAGVIAPVTSGMIQSPQKCYAYSINQKAYSNTYQEFT

NIDQAKAWGNAQYKKYGLSKSEKEAIVSYTKSASEINGKLRQNKGVINGF

PSNLIKQVELLDKSFNKMKTPENIMLFRGDDPAYLGTEFQNTLLNSNGTI

NKTAFEKAKAKFLNKDRLEYGYISTSLMNVSQFAGRPIITKFKVAKGSKA

GYIDPISAFAGQLEMLLPRHSTYHIDDMRLSSDGKQIIITATMMGTAINP

K

In some embodiments, an active domain amino acid sequence is as follows:

(SEQ ID NO: 13)
SAYSNTYQEFTNIDQAKAWGNAQYKKYGLSKSEKEAIVSYTKSASEINGK

LRQNKGVINGFPSNLIKQVELLDKSFNKMKTPENIMLFRGDDPAYLGTEF

QNTLLNSNGTINKTAFEKAKAKFLNKDRLEYGYISTSLMNVSQFAGRPII

TKFKVAKGSKAGYIDPISAFAGQLEMLLPRHSTYHIDDMRLSSDGKQIII

TATMMGTAINPK

In some embodiments, an active domain amino acid sequence is as follows:

(SEQ ID NO: 14)
MSAYSNTYQEFTNIDQAKAWGNAQYKKYGLSKSEKEAIVSYTKSASEING

KLRQNKGVINGFPSNLIKQVELLDKSFNKMKTPENIMLFRGDDPAYLGTE

FQNTLLNSNGTINKTAFEKAKAKFLNKDRLEYGYISTSLMNVSQFAGRPI

ITKFKVAKGSKAGYIDPISAFAGQLEMLLPRHSTYHIDDMRLSSDGKQII

ITATMMGTAINPK

In some embodiments, an active domain comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with SEQ ID NO: 12. In some embodiments, an active domain comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with SEQ ID NO: 13. In some embodiments, an active domain comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or 100% sequence identity with SEQ ID NO: 14.

Fibrinogen Composition

In accordance with the present invention, therapeutic compositions for use as tissue adhesives, sealants or hemostatic agents can be made using the proteins fibrinogen and thrombin, Cronkite, E. P. et al., J.A.M.A., 124, 976 (1944), Tidrick, R. T. and Warner, E. D., Surgery, 15, 90 (1944). Fibrinogen is a soluble protein found in the blood plasma of all vertebrates that when contacted by thrombin (another plasma protein) becomes polymerized to an insoluble gel-like network. In polymerized form, the fibrinogen is referred to as fibrin. The conversion of fibrinogen to fibrin is crucial to normal hemostasis in vertebrates.

There are numerous potential advantages, relative to the use of synthetic materials, associated with the use of fibrinogen as an adhesive, sealant or hemostatic agent. For example, when applied to a wound, polymerized fibrinogen (fibrin) forms a network or scaffolding through which it is more likely that immunologically active cells (to defend against invading pathogens) and also epithelial cells (for tissue regeneration and repair) can migrate. Additionally, fibrin materials may be dissolved gradually by the body (a process termed fibrinolysis) after treatment.

Figure 10:
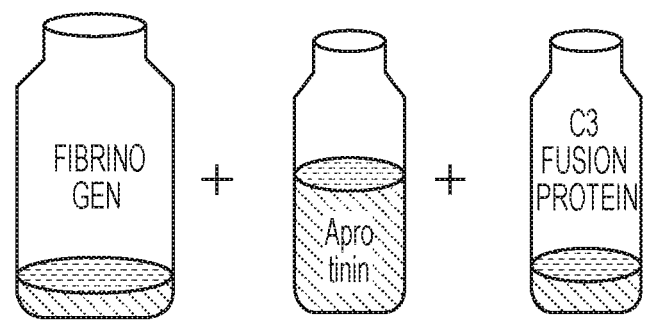
FIG. 10 depicts an exemplary illustration of combining fibrinogen, aprotinin and a C3 fusion protein to create a C3 fusion protein-fibrinogen solution and separately combining thrombin and $CaCl_2$ to create a thrombin solution and then putting each solution in a separate chamber of a Duploject Syringe.
Figure 10:
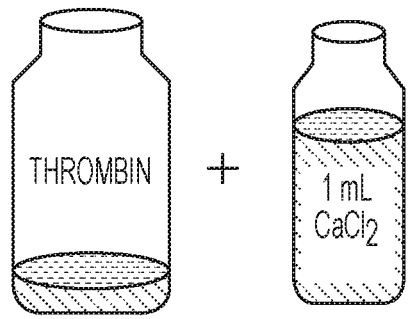
Figure 10:
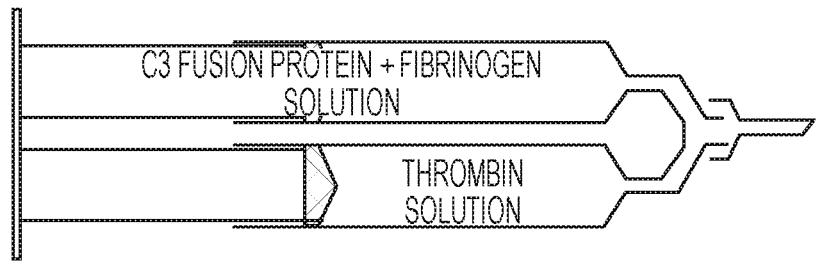
Figure 11:
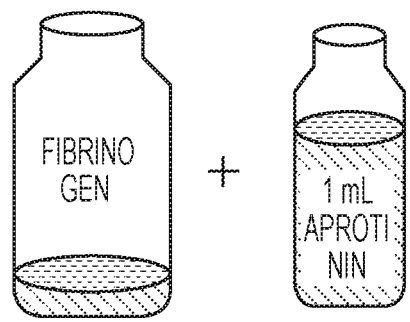
FIG. 11 depicts an exemplary illustration of combining fibrinogen and aprotinin fibrinogen solution and separately combining thrombin, $CaCl_2$ and a C3 fusion protein to create a C3 fusion protein-thrombin solution and then putting each solution in a separate chamber of a Duploject Syringe.
Figure 11:
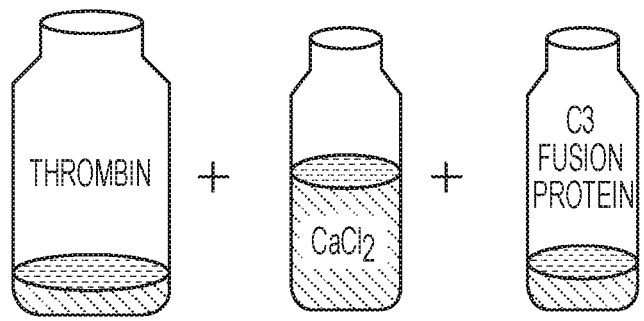
Figure 11:
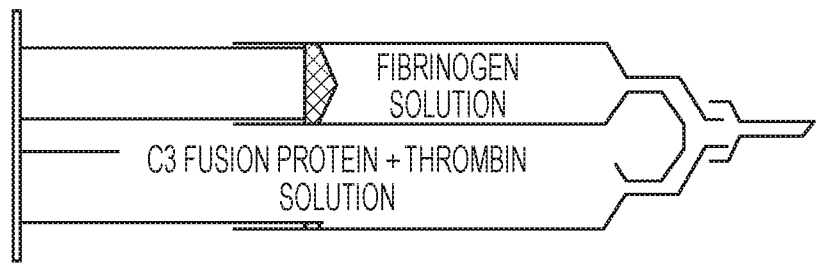

In some embodiments, a pharmaceutically effective amount of a therapeutic protein as described above is combined with a fibrinogen composition to generate a therapeutic protein-fibrinogen composition (see, for example, FIG. 10). The notation "therapeutic protein-fibrinogen" or "therapeutic polypeptide-fibrinogen" simply indicates that the composition comprises both components (the therapeutic protein/polypeptide and fibrinogen), rather than indicating some form of bond (e.g., covalent bond) between the components. In some embodiments, a pharmaceutically effective amount of a therapeutic protein as described above is first added to a solution comprising one or more plasminogen-activator inhibitors or plasmin inhibitors before mixing with the fibrinogen composition. In some embodiments, the one or more plasminogen-activator inhibitors or plasmin inhibitors comprises aprotinin. In some embodiments, the fibrinogen composition comprises a protease inhibitor before it is combined with a pharmaceutically effective amount of a therapeutic protein as described above. In some embodiments, the fibrinogen composition comprises aprotinin. In some embodiments, a suitable fibrinogen composition further contains albumin, one or more blood coagulation factors, and/or globulin. In some embodiments, a pharmaceutically effective amount of a therapeutic protein as described above is combined with a thrombin composition before it is combined with a fibrinogen composition (see, for example, FIG. 11).

In some embodiments, a pharmaceutically effective amount of a therapeutic protein as described above is combined with a commercially available fibrin sealant. In some embodiments, the commercially available fibrin sealant is TISSEEL. In some embodiments, the commercially available fibrin sealant comprises fibrinogen, thrombin, Factor XIII, plasmafibronectin, plasminogen, aprotinin solution and calcium chloride solution.

Compositions provided by the invention, or used in the invention, can be defined as "does not contain a thrombin". This statement indicates that the composition is free from thrombin, or that any thrombin that is present cannot be detected because it is below the limit of quantification when the composition is analyzed by one or more of size exclusion chromatography-high performance liquid chromatography (SEC-HPLC), SDS-PAGE, capillary electrophoresis-SDS PAGE (CE-SDS PAGE), and/or reverse phase-high performance liquid chromatography (RP-HPLC).

Thrombin Composition

In accordance with the present invention, a therapeutic composition comprises a pharmaceutically effective amount of a therapeutic protein as described above and a fibrinogen composition that comprises a protease inhibitor, such as aprotinin, and may further comprise a serine protease, such as, for example, a thrombin composition.

Thrombin converts soluble fibrinogen into insoluble strands of fibrin, as well as catalyzing many other coagulation-related reactions. In some embodiments, a thrombin composition comprising thrombin is combined with a therapeutic protein-fibrinogen composition to generate a therapeutic protein-fibrinogen-thrombin composition. In some embodiments, a therapeutically effective amount of a therapeutic protein is combined with each of a fibrinogen composition comprising a fibrinogen and a thrombin composition to generate a therapeutic protein-fibrinogen-thrombin composition, wherein the therapeutic protein comprises an amino acid sequence of a transport domain covalently linked to an amino acid sequence of an active domain, said amino acid sequence of said active domain is selected from an ADP-ribosyl transferase C3, a fragment thereof retaining ADP-ribosyl transferase activity, or an amino acid sequence having at least 80% sequence identity thereto, and wherein said amino acid sequence of said transport domain is selected from a subdomain of Tat peptide or antennapedia peptide, a fragment of Tat peptide or antennapedia peptide, a polypeptide derived from a nucleotide sequence encoding a Tat peptide or antennapedia peptide, or an amino acid sequence having at least 80% sequence identity thereto. In some embodiments, the thrombin composition comprises calcium chloride.

Administration

The present invention provides methods for preparing and administering therapeutic compositions comprising a therapeutic protein-fibrinogen-thrombin composition to subjects in need thereof. In some embodiments, administration comprises contacting a tissue, nerve injury site, open wound, etc. with a therapeutic composition of the present invention in a pharmaceutically effective amount sufficient to promote the therapeutic effect of the therapeutic protein (e.g., facilitating axon growth, tissue repair, etc.). Application of the therapeutic compositions can be done by any suitable method known in the art. Specific examples include dripping or spraying using a cannula or spray set, etc. See, for example, Tisseel product monograph (2013) and Evicel product monograph (2010). In some embodiments, the therapeutic compositions are applied as a layer(s) onto a subject's tissue. In some embodiments, the therapeutic compositions are applied (e.g., sprayed or dripped) onto the tissue in short bursts (for example, 0.1 to 0.2 mL). In some embodiments, the therapeutic compositions are applied as a layer onto a patient undergoing surgery. In some embodiments, each of the pharmaceutical compositions described above is independently employed as the therapeutic composition in such methods for preparing and administering therapeutic compositions.

Kits

One aspect of the invention relates to kits for the use of treating spinal cord injury, comprising a therapeutic protein as described above, for use in facilitating axon growth, treating spinal cord injury (e.g., nerve injury arising from traumatic nerve injury or nerve injury caused by disease), preventing (e.g., diminishing, inhibiting) cell apoptosis, suppressing the inhibition of neuronal axon growth, treating ischemic damage related to stroke, suppressing Rho activity, regenerating injured axons (e.g., helping injured axon to recover, partially or totally, their function), and/or facilitating the formation of new neuronal connections (e.g., developing axons, dendrites, neurites) with other (surrounding) cells (e.g., neuronal cells), in a mammal, (e.g., human).

In some embodiments, a kit to promote neuroregeneration and neuroprotection comprises a first container containing a pharmaceutical composition comprising a therapeutic protein described herein, a second container containing a fibrinogen composition, and a third container containing a thrombin composition. In some embodiments, a fibrinogen composition comprises fibrinogen, albumin, one or more blood coagulation factors, and/or globulin. In some embodiments, a kit further comprises an additional container containing a solution comprising one or more plasminogen-activator inhibitors or plasmin inhibitors. In some embodiments, one or more plasminogen-activator inhibitors or plasmin inhibitors comprise aprotinin. In some embodiments, a kit further comprises a solution comprising calcium chloride.

In some embodiments, a kit further comprises a syringe. In some embodiments, a syringe is a Duploject Syringe (Baxter Product Code 1501252). As used herein, the term "Duploject Syringe" may be replaced by a syringe which is defined as one which: comprises a clip for two disposable syringes for simultaneous application of two-component products, e.g., a fibrin sealant; is a device that enables the mixing of the contents of two syringes and then the mixed contents exit through one outlet; is a device that discharges the contents of two syringes as if the contents of both syringes were already mixed in one syringe; and/or enables the mixing of the contents of two syringes and then the expulsion through one outlet, when a force is applied to the syringes.

In more detail, the syringe defined in the previous paragraph is a device comprising two syringes, wherein the plunger for each syringe is joined together at one end, wherein in the nozzle of each syringe is attached to a Y-shaped connector; so when a force a applied via the plungers, it is applied equally to each syringe, causing the contents of each syringe to be forced out via the nozzle into the Y-shaped connector, where the contents mix, and then the mixed contents exit through the single outlet of the Y-shaped connector. The single outlet of the Y-shaped connector can be fitted with a cannula.

In some embodiments, the syringe defined in the previous two paragraphs comprises a syringe of therapeutic polypeptide-fibrinogen composition and a syringe of thrombin, wherein the plunger of each syringe is joined together at one end, wherein in the nozzle of each syringe is attached to a Y-shaped connector; so when a force is applied via the plungers, the force is applied equally to each syringe, causing the contents of each syringe to be forced out via the nozzle into the Y-shaped connector, where the contents mix, initiating fibrin production, and then the mixed contents exit through the single outlet of the Y-shaped connector. The single outlet of the Y-shaped connector can be fitted with a cannula.

In some embodiments, a kit to promote neuroregeneration and neuroprotection comprises a first chamber containing a pharmaceutical composition comprising a therapeutic protein described herein and a fibrinogen composition, and a second chamber containing a thrombin composition. In some embodiments, a first chamber further contains one or more plasminogen-activator inhibitors or plasmin inhibitors. In some embodiments, one or more plasminogen-activator inhibitors or plasmin inhibitors comprises aprotinin. In some embodiments, a thrombin composition comprises thrombin and calcium chloride. In some embodiments, each of the pharmaceutical compositions described above is independently employed as the therapeutic composition in the first chamber of the kits.

EXAMPLES

While certain compounds, compositions and methods of the present invention have been described with specificity in accordance with certain embodiments, the following examples serve only to illustrate the compounds of the invention and are not intended to limit the same.

Example 1. Bacterial Culture Process of C3 Fusion Proteins

In one exemplary process, C3 fusion protein is expressed from a T7 promoter-driven vector and *E. coli* BL21 (DE3) microbial host expression system yielding a high level of intracellular expression upon the induction of IPTG. Following expression, cells are harvested and homogenized, releasing C3 fusion protein and other host-cell-derived impurities into the culture broth. The homogenate is cleared of cell debris by centrifugation and subsequent tangential flow filtration (TFF). C3 fusion protein is purified by various chromatography steps, followed by a buffer-exchange step to condition the material for filtration by a Q-membrane adsorber. Finally, purified C3 fusion protein is concentrated and exchanged into drug substance (DS) formulation buffer.

Overview of the Host Vector System

An exemplary C3 fusion protein was expressed from a T7 promoter driven vector with a Kanamycin selectable marker from an *E. coli* BL21 (DE3) microbial host expression system. BL21 has been widely used as an *E. coli* host background for expressing recombinant proteins. It does not contain the Lon protease and also is deficient in the outer membrane protease, OmpT. The lack of the two key proteases reduces degradation of heterologous proteins expressed in the strains.

BL21 (DE3) is a DE3 derivative of BL21. The DE3 designation indicates that the strain contains the λDE3 lysogen that carries the gene T7 polymerase under the control of the lac UV5 promoter. cDNA comprising SEQ ID NO: 3 encoding an exemplary C3 fusion protein was cloned into a protein expression vector. The combination of a T7 promoter-driven vector and a BL21 (DE3) host strain yielded a high level of expression of mRNA encoding the recombinant protein upon induction of IPTG. Clone selection was based on SDS-PAGE analysis (Coomassie staining and scanning densitometry) of the crude extracts from the inductions. The clone expressing the highest level of C3 fusion protein was selected and used to establish a Working Cell Bank.

This example demonstrates that a bacterial culture system may be used to successfully express C3 fusion proteins.

Seed Culture

A pre-culture shake flask containing growth medium was inoculated with a Working Cell Bank vial. The Working Cell Bank vial may refer to any number of cells, including a single cell. The cells were cultivated at 37° C. to reach an optical density (OD, measured at 600 nm) optimal level (e.g., 2-10 OD). This culture was used for inoculation of the production bioreactor to a starting OD of 0.004.

Fermentation

Figure 4A:
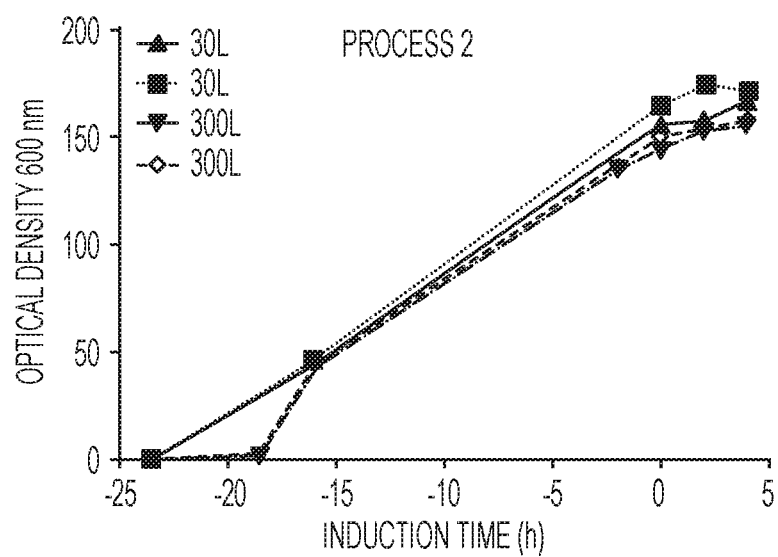
FIGS. 4A and 4B show exemplary cell growth profiles using the HCD fermentation method (FIG. 4A) and the standard fermentation method (FIG. 4B).
Figure 4B:
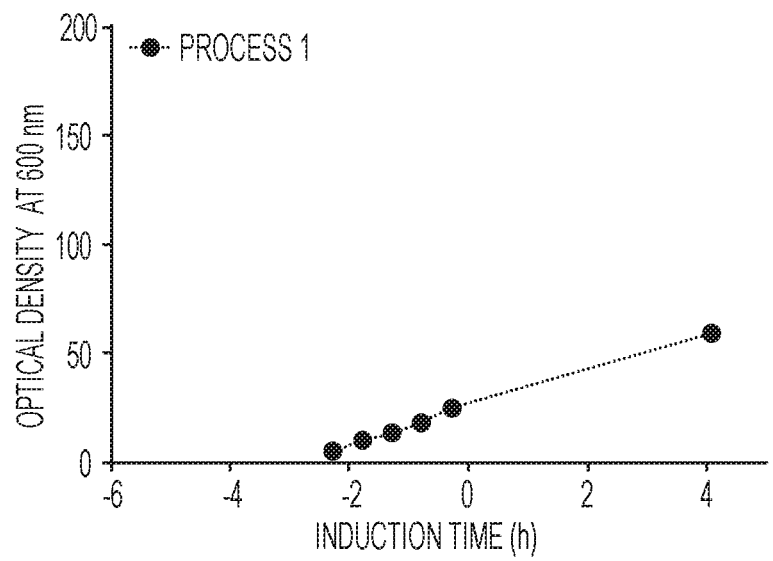

To maximize yield and robustness, a high-cell density (HCD) fermentation process was used. Cell growth profiles using the HCD fermentation method provided three times higher OD values (FIG. 4A) compared to the standard fermentation method (FIG. 4B). The fermentation process producing exemplary C3 fusion protein was performed in a Sartorius bioreactor set up. Dissolved oxygen and pH was controlled throughout the production process. Fermentation started in batch mode, in which a defined amount of initial carbon source (glucose) was provided in the medium. After consumption of the glucose in the medium, (carbon source limitation, typically within 7.5 hours), a fed-batch mode was started. In the fed-batch mode, a glycerol carbon source feed solution was introduced to the fermentor at an exponential rate, followed by a second phase of constant feeding. Thus, the feeding strategy consisted of two phases: a first stage of exponential feeding, which lasted 7-8 hours and a second stage of constant feeding for 8.5 hours (8-9 hours). An exemplary fermentation process is shown in FIG. 1.

$1^{st}$ stage: Exponential feeding was controlled using:

$$\text{Exp. Feed}\left[\frac{g}{h}\right] = 1000 * \left[\left(\frac{\mu}{Y_{\frac{x}{s}}} + m\right) \cdot V_0 \cdot X_0 \cdot \frac{1}{S_F} \cdot e^{(\mu \cdot t)}\right]$$

Where;

Specific growth rate, $\mu$, (1/h)=0.12-0.18/hr,

Biomass yield on glucose, Yx/s, (g/g)=0.32-0.48 g/g,

Maintenance factor, m, (g/g/hr)=0.32-0.48 g/g/hr,

Initial volume of reactor before the start of feed, $V_0$, (L)=12 L,

Biomass concentration before the start of feed, $X_0$, (g/L)=8-12 g/L,

Feed concentration, $S_F$, (g/kg)=480-720 g/kg

Time, t, (hrs)=7-8 hrs $2^{nd}$ stage: Constant feed rate=Feed rate at the end of the exponential feeding stage.

Figure 3:
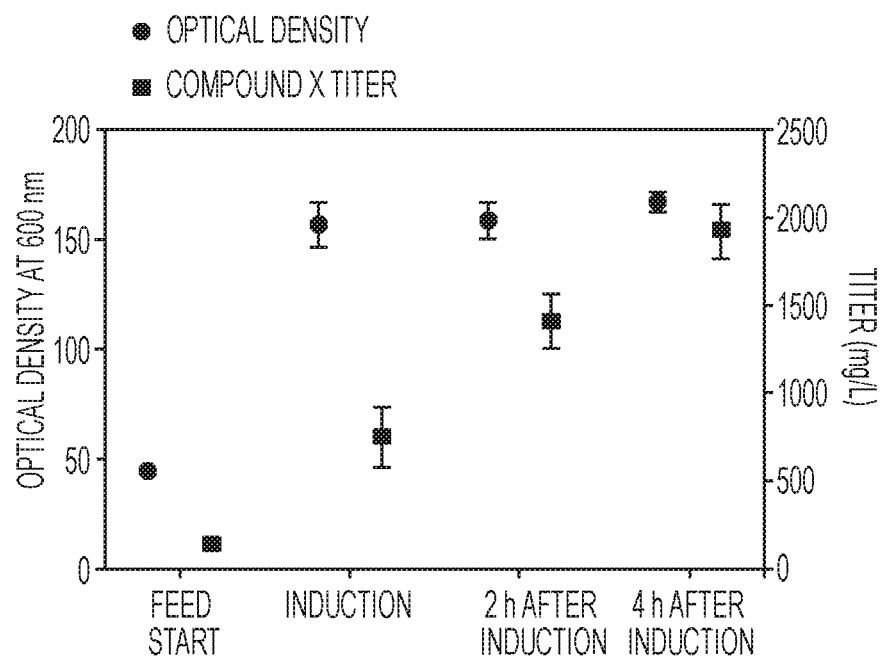
FIG. 3 shows exemplary C3 fusion protein (Compound X) production titer at 30 liter development scale.

The temperature during the initial batch mode and the fed batch mode was maintained at 37° C. until the start of induction. C3 fusion protein production was triggered by the addition of an inducing agent, 5 mM IPTG (Isopropyl β-D-1-thiogalactopyranoside) after the first 8.5 hours of constant feeding ($2^{nd}$ stage). The constant feed rate of the $2^{nd}$ stage was maintained during induction. At the start of induction, the temperature was shifted to 28° C. After 4 hours of induction, the fermentor was further cooled to 8° C. (within an hour) and the culture was harvested for homogenization. Exemplary C3 fusion protein production is shown in FIG. 1 and FIG. 3.

Homogenization

Harvested cells were homogenized in APV1000 (homogenizer) to lyse the cells. Pressure was maintained at 690 bar with 3 cycles of homogenization. During this time, the temperature of the feed and homogenate was maintained at 8° C.-11° C.

Centrifugation

Centrifugation was performed in a semi-continuous mode using a CEPA centrifuge (model Z41). Flow was maintained at 30 L/hr in a 17000 g centrifugal force. The temperature of the supernatant was maintained at 15° C.

Tangential Flow Filtration

The supernatant comprising the cell lysate was clarified by a Tangential Flow Filtration (TFF) system equipped with a Sartorius Sartocon slice membrane (1000 kDa, 0.5 m$^2$). The filtration was performed in two steps: a concentration phase and a diafiltration phase. Within the concentration phase, the supernatant was reduced by volume factor of 2. Within the diafiltration phase, the retentate was continuously washed with 5 volumes of diafiltration buffer while the product was collected on the permeate side. The temperature of the retentate was maintained at 15° C. throughout the TFF operation. The permeate was then sterile-filtered before loading onto the Cation Exchange Column I.

Example 2. C3 Fusion Protein Capture and Purification Process

This example demonstrates that a simplified downstream purification process may be used to capture and purify C3 fusion proteins. C3 fusion protein is purified by various chromatography steps, followed by a buffer-exchange step to condition the material for filtration by a Q-membrane adsorber. Finally, purified C3 fusion protein is concentrated and exchanged into drug substance (DS) formulation buffer.

Cation Exchange Column I

TFF permeate containing C3 fusion protein was conditioned to an optimal conductivity and then filtered using a Sartoban filter. To capture the C3 fusion proteins from most host-cell derived impurities, a SP Sepharose cation exchange resin column was equilibrated and the conditioned permeate containing the C3 fusion was loaded onto the capture column comprising the cation exchange resin, washed and then eluted in a single step by increasing salt concentration (e.g., NaCl). The peak eluate containing the C3 fusion protein was collected.

Cation Exchange Column II

Figure 8:
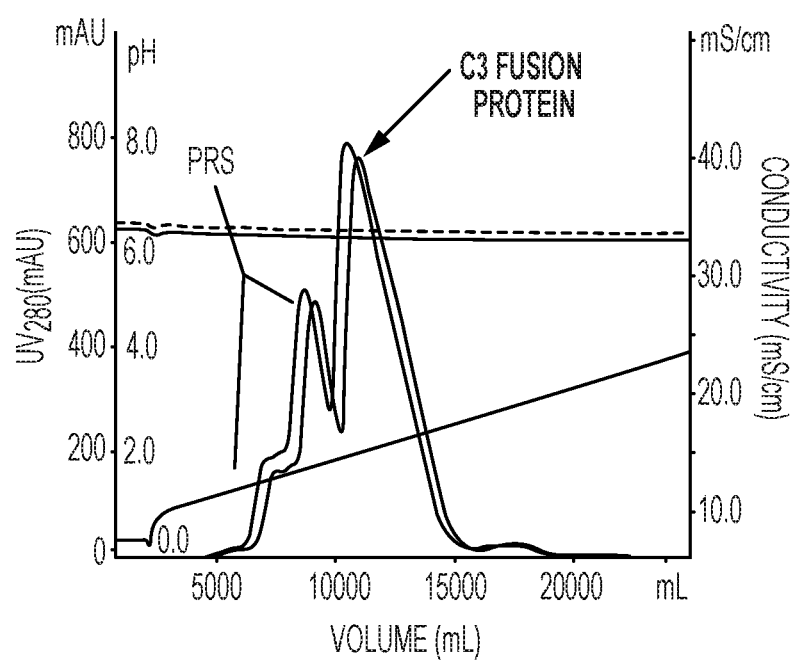
FIG. 8 shows exemplary chromatograms from two exemplary batches of C3 fusion protein drug substance purified with Process 2 including an intermediate cation exchange column.

The peak eluate pool was then conditioned to a conductivity of 7.5±0.5 mS/cm by diluting with a 10 mM NaH2PO4, 10 mM citric acid, 0.5 mM EDTA, pH 7.0 buffer. The pool containing the C3 fusion was loaded onto an intermediate chromatography column with a strong cation exchange resin (e.g., YMC Biopro S30) to resolve and isolate C3 fusion protein product from protein contaminants with highly similar biophysical properties. Prior to loading, the column was equilibrated. After loading, the column was washed and then eluted using a linear salt gradient (e.g., NaCl). The addition of an intermediate chromatography column with a strong cation exchange resin (e.g., YMC Biopro S30) increased the purity of C3 fusion protein and reduced batch to batch variability (FIG. 8).

Hydrophobic Interaction Chromatography

The product collection pool from the intermediate cation exchange column (e.g., YMC Biopro S30) was adjusted to a final $(NH_4)_2SO_4$ concentration of 1.6±0.1 M. The pool was then filtered using a Sartoban P 0.2 µm filter and loaded onto a hydrophobic interaction chromatography (HIC) column (e.g., Butyl 650M), whereby proteins bind at a high lyotropic salt concentration and elute at low lyotropic salt concentration. HIC column was equilibrated using one or more column volumes of equilibration buffer. After loading, the column was washed and the C3 fusion protein was eluted from the column in a single step by altering the salt concentration of the mobile phase. The peak eluate containing the C3 fusion protein was collected.

Ultrafiltration/Diafiltration I

The HIC collection eluate was then loaded onto an ultrafiltration/diafiltration (UF/DF) membrane (Pellicon 3 Ultracell 5 kDa MWCO) pre-conditioned with elution buffer from the HIC column. Diafiltration was performed with 6 diavolumes of Q-membrane Adsorber buffer to buffer exchange the peak eluate from the HIC column containing C3 fusion protein.

Q-Membrane Adsorption

The diafiltration retentate was loaded onto an ion exchange membrane to remove negatively charged contaminants such as DNA, host-cell proteins and endotoxins. The ion exchange membrane (e.g., Sartobind Q Single Sep Mini) was equilibrated and the diafiltration retentate was loaded in flow-through mode. The main fraction collection began when the ascending elution peak reached absorbance of 50 mAU and continued until absorbance dropped on the tailing edge of the peak to 50 mAU. The flow-through containing the C3 fusion protein was then filtered using a Sartoban P 0.2 µm filter.

Ultrafiltration/Diafiltration II

C3 fusion protein was then loaded onto a pre-conditioned UF/DF membrane (e.g., Pellicon Ultracell 5 kDa MWCO). Concentration was performed until the target C3 fusion protein concentration was reached (e.g., 10-15 or 30-37 mg/mL). Subsequently, diafiltration was performed with 5 mM sodium citrate, pH 6.5, until 8 diavolumes were completed. The product was then filtered using a Sartoban P 0.2 µm filter. The filtered UF/DF II retentate was the C3 fusion protein Drug Substance.

Example 3. Exemplary High Cell Density Process for Producing Recombinant C3 Fusion Protein Table 2 shows fermentation parameters for an exemplary process.

TALE 2

| Parameter | | |
|---|---|---|
| Feeding | C-source | Glycerol |
| | Feed trigger | pH spike (~7.5 h) (OD 40-50) |
| | Feed profile | 7.5 h exponential 8.5 h constant |
| Induction | $OD_{600}$ | 145-175 |
| | Time (h) | 4 |
| End of Fermentation | $OD_{600}$ | 145-195 |
| | Time (h) | 27.5 |
| | Titer | 2 |

Table 3 shows process steps for an exemplary process.

TABLE 3

| Manufacturing Process Step | |
|---|---|
| Drug Substance | |
| Fermentation Scale | 300 L |
| Fermentation | HCD process |
| Cell Harvest | Fermentation broth taken directly to homogenization |
| Clarification (Centrifugation) | Homogenate is centrifuged to clear cell debris |
| Clarification (Tangential Flow Filtration) | Sartocon Slice 0.1 µm membrane, high-salt diafiltration buffer, 15° C. |
| Cation-Exchange Chromatography I | 10 ± 2 cm bed height |
| Cation-Exchange Chromatography II | Intermediate purification step |
| Target Concentration of Bulk Drug Substance (BDS) | 31-37 mg/mL |
| Packaging | Polycarbonate |
| Drug Product | |
| Concentration step | Dilute as necessary for each dose (27-33 mg/mL) |

C3 fusion protein was produced by high cell density fermentation with an exponential feeding strategy as described above. After IPTG induction, cells were harvested and homogenized such that C3 fusion protein was released directly into the fermentation broth. The resulting mixture was centrifuged and clarified using TFF as described in Example 1. Following TFF, the resulting permeate was sterile filtered and purified according to Example 2. C3 fusion protein purified as described above resulted in a composition of C3 fusion protein at a concentration of 31-37 mg/mL with an improved purity profile as shown in Table 6.

Example 4. Analytical Methods of Recombinant C3 Fusion Protein

Glycohydrolase (GH) Enzyme Assay

The intracellular action of C3 exoenzymes and C3 fusion proteins results from transfer of an ADP-ribose moiety to an asparagine residue in Rho GTPase, trapping this GTPase in its inactive conformation. An exemplary C3 fusion protein is an ADP-ribosyltransferase that catalyzes hydrolysis of NAD+ in the absence of the specific protein substrate, Rho. C3 fusion protein catalyzes transfer of an ADP-ribose moiety to the RhoA, RhoB and RhoC members of the Rho family of small GTPases. In neurons the predominant species is RhoA, so the numbering system for RhoA and the abbreviation "Rho" is used. A spectrofluorometric glycohydrolase (GH) activity assay was used to measure glycohydrolase (GH) as the formation of a fluorescent product, which gives a sensitive and reliable method to serve as a test of identity and potency.

The GH assay measures the formation of ε-ADP-ribose produced as a result of hydrolysis of ε-NAD by C3-variants. Glycohydrolase activity of C3-variants converts ε-$NAD^+$ into ε-ADP-ribose, a molecule with 10 times higher fluorescence intensity at the selected wavelengths. The fluorescence intensity of ε-ADP-ribose is used to measure the amount of ε-ADP ribose formed by using a standard curve of fluorescence of known concentrations of ε-AMP. The fluorescence intensities of ε-AMP and ε-ADP-ribose are measured by exciting the reaction at 305 nm and recording the emission at 410 nm. A unit of activity is defined as nmoles ADP-ribose formed in 30 min at 37° C. The assay is linear with up to at least 12 µg of C3-variant protein and up to least 180 min of incubation time. This assay has been found to be precise, accurate and reproducible. This assay has also been found to be useful in measuring decreases in enzymatic activity after incubation at 70° C., and can be considered to be stability-indicating when used in a well-designed stability study.

Using the spectrofluorometric GH assay, experiments were performed with exemplary C3 fusion protein with increasing concentrations of ε-NAD (FIG. 2). At 600 µM to 1000 µM ε-NAD, the plateau in the amount of ε-ADP-ribose formed indicates a saturating concentration of the substrate. The concentration of substrate chosen for the assay was 0.4 mM ε-NAD in order to allow more sensitivity in detecting GH activity.

Glycohydrolase (GH) Enzyme Assay as a Stability-Indicating Assay

Hydrolysis, oxidation, deamidation, aggregation, denaturation or other breakdown pathways during fermentation, purification, transport or storage of C3-variants could decrease the specific activity of a preparation. The stability-indicating potential of the GH enzyme assay using an accelerated temperature stability experiment was carried out at 70° C.

Purity Profile of Exemplary C3 Fusion Protein

The purity of C3 fusion protein was evaluated using RP-HPLC, SEC-HPLC, and SDS-PAGE analysis. Purity levels of product materials from development batches routinely exceeded 95%. In an E. coli-derived recombinant protein product, pyrogenicity, bioburden and residual DNA levels are critical for safety. Another impurity to be minimized for safety reasons is host cell protein. This is addressed directly by a quantitative ELISA and indirectly by purity estimate on SDS-PAGE. Additionally, a significant host cell contaminant may give a signal upon N-terminal or C-terminal sequencing or mass spectrometry. Taken together, the purity/impurity profile for general safety issues associated with E. coli as a host cell is tolerable. Accelerated stability studies and release testing indicated a very small amount of multimers, detected by SE-HPLC. These are known not to be mediated by cysteine-linked disulfide bond formation, because the exemplary C3 fusion protein lacks a cysteine residue. The impurities detected by RP-HPLC are in general <1%.

Exemplary C3 fusion protein drug substance test results are indicated in Table 4. Test results shown in Table 4 correspond to drug substance produced using Process 1. Process 1 includes production using standard fermentation that does not employ high cell density fermentation with an exponential feeding strategy. After IPTG induction, cells were harvested by centrifugation and homogenized. The resulting lysate was clarified using TFF. The TFF permeate was subjected to cation exchange, followed by HIC, UF/DF, Q-membrane adsorption and a second UF/DF.

TABLE 4

Exemplary test results

| Test Type | Test Method | Specification | Test Results |
|---|---|---|---|
| Strength | | | |
| Protein Concentration | UV Analysis[1] | 13-19 mg/mL | 15.7 mg/mL |
| Potency | | | |
| Biological Activity | Glycohydrolase Enzyme Assay[2] (Units/mg C3 fusion protein) | 20-40 Units | 33 Units |
| Identity | | | |
| Molecular Size | Reduced SDS-PAGE | Compares to reference standard; major band migrates between 21 and 31 kDa | Meets criteria |
| pH | cIEF | 10.0-10.2 | 10.1 |
| Purity | | | |
| Quality | RP-HPLC | >95% | 99% |
| | SEC-HPLC | >95% monomer | 100% |
| | Reduced SDS-PAGE | ≥95% as determined by scanning densitometry or image analysis | 96.6% |
| Appearance | Visual Inspection | Clear, colorless liquid, essentially free of visible particles | Clear, colorless liquid, essentially free of visible particles |

TABLE 4-continued

Exemplary test results

| Test Type | Test Method | Specification | Test Results |
|---|---|---|---|
| pH @ 25° C. | pH Measurement | 6.8-7.8 | 7.2 |
| E. coli. Residual DNA | Hybridization Method[3] | <1 ng/mg[4] | ≤11 pg/mg |
| Host Cell Proteins | Host Cell Proteins Immunoassay | <10 µg/mg | 0.86 µg/mg |
| Safety | | | |
| Endotoxin | LAL | ≤1 EU/mg | 0.74 EU/mg |
| Bioburden | Membrane Filtration | <1 CFU/10 mL | 0 CFU/10 mL |

N.T. = not tested
[1]Extinction coefficient is 0.72 as determined by amino acid analysis
[2]Unit definition: 1 unit = 1 nmol of ADP-ribose/(mg protein × 30 min) @ 37° C.
[3]Selected as a replacement for PicoGreen method.
[4]Current WHO guidelines specify <10 ng/dose. If a drug product of exemplary C3 fusion protein dose containing 10 mg of C3 fusion protein is assumed, then the limit becomes <1 ng/mg.

Further characterization attributes may be measured using LC-MS based methods to determine deamidation, methionine oxidation and peptide mapping. Additional characterization can include immunochemical homogeneity via Western blot; residual levels of PPG-200 defoamer, IPTG, and edetate disodium dihydrate, molecular ion measurements with MALDI-TOF-MS or high resolution mass spectrometry; N-terminal and C-terminal sequencing with digestion and/or Edman degradation; amino acid analysis with HCl hydrolysis; osmolality; Far-UV Circular Dichroism; Near-UV Circular Dichroism; Fourier transform infrared spectroscopy (FTIR); Intrinsic fluorescence; differential scanning calorimetry (DSC); and sedimentation velocity analytical ultracentrifugation (SV-AUC).

Example 5. Analytical Methods of Recombinant C3 Fusion Protein

This example demonstrates characterization of an exemplary purified C3 fusion protein. Specifically, a C3 fusion protein comprising SEQ ID NO: 1 is a recombinant protein composed of 231 amino acids with a theoretical molecular weight of 25,726 daltons (a nominal molecular weight of 26-28 kDa is used for analytical purposes) and theoretical isoelectric point (pI) of 9.6. The extinction coefficient has been determined by amino acid analysis to be 0.72 units of absorbance at $A_{280\,nm}$ per mg of protein.

Upon expression and purification of the coding region comprising SEQ ID NO: 3, according to the present invention, the N-terminal methionine is present in fewer than 15% of the molecules, as determined by mass spectrometry. Confirmation of this sequence and the primary structure of C3 fusion protein have been completed using amino acid analysis, peptide mapping, N-terminal sequencing, C-terminal sequencing, and mass spectrometry. The C-terminal sequence was determined to be FVMNPANAQGRHTPGTRL (SEQ ID NO: 4), in agreement with the theoretical sequence. Molecular ion by MALDI-TOF was reproducibly found to be approximately 25,726 m/z. This corresponds to a polypeptide of 231 amino acids matching the theoretical peptide sequence, at least 85% of the molecules missing the N-terminal methionine residue. Peptide mapping providing 97%-100% coverage has confirmed the theoretical protein sequence, and the amino acid sequence results correspond with those expected the theoretical sequence.

Exemplary characterization results are shown in Table 5.

TABLE 5

Exemplary characterization results

| Test type | Method | Target acceptance criteria | Result |
|---|---|---|---|
| N-terminal sequencing | Edman degradation | (M)SAYSNTYQEF (SEQ ID NO: 5) | (M)SAYSNTYQEFTNIDQA (SEQ ID NO: 6) |
| C-terminal sequencing | MS/MS | QGRHTPGTRL (SEQ ID NO: 7) | FVMNPANAQGRHTPGTRL (SEQ ID NO: 4) |
| Immunochemical homogeneity | Immunoblot with RAb-01 antiserum | Immunoreactive 26 kDa band | Immunoreactive 26 kDa band |
| Deamidation | TBD | To be determined | N.T. |
| Methionine oxidation | Tryptic RP-HPLC | <15% overall average | ~10% overall average |
| Amino Acid analysis | HCl hydrolysis | 90-110% of expected mass | 100% of expected mass |
| Peptide mapping | Tryptic RP-HPLC | >95% coverage | 100% coverage |
| Molecular ion | MALDI-TOF MS | 25,726 m/z | 25,726 m/z |
| Biological Activity | Bioassay at two concentrations | Neurite outgrowth; Increased >2 fold at low conc. >3 fold increase at high conc. | 2.8-fold (low) 6.2-fold (high) |

Figure 6:
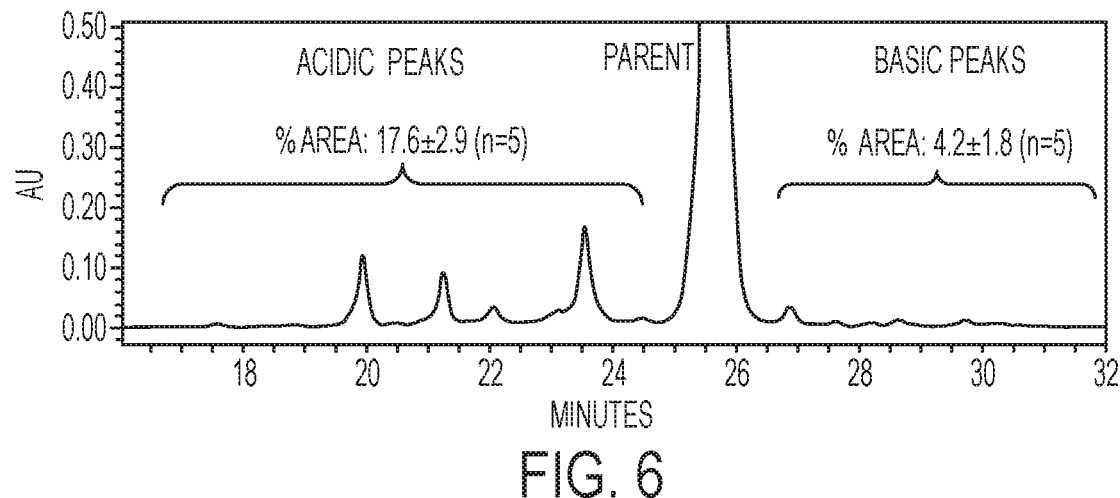
FIG. 6 shows characterization of exemplary C3 fusion protein drug substance produced by Process 1 using IE-HPLC.
Figure 7A:
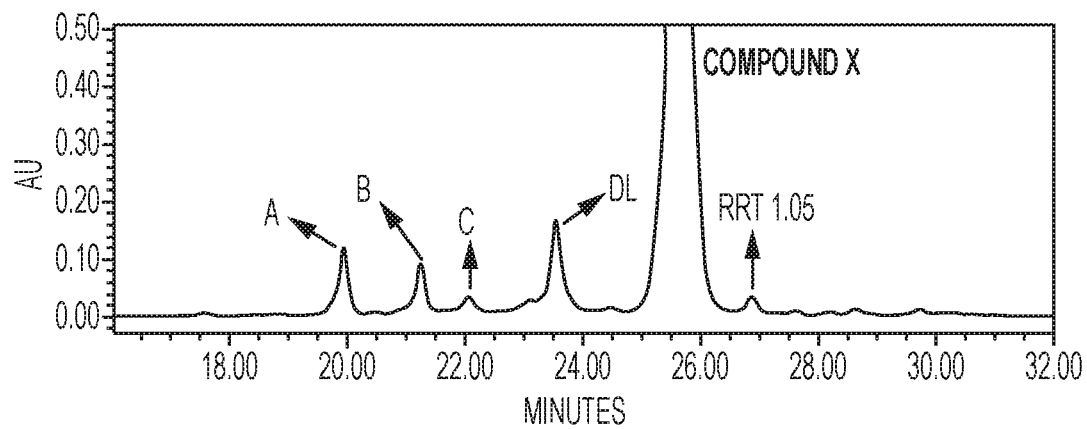
FIG. 7A shows characterization of exemplary C3 fusion protein drug substance produced by Process 1 after the fermentation and downstream processes and Process 2 after the fermentation but prior to the downstream processes.
Figure 7B:
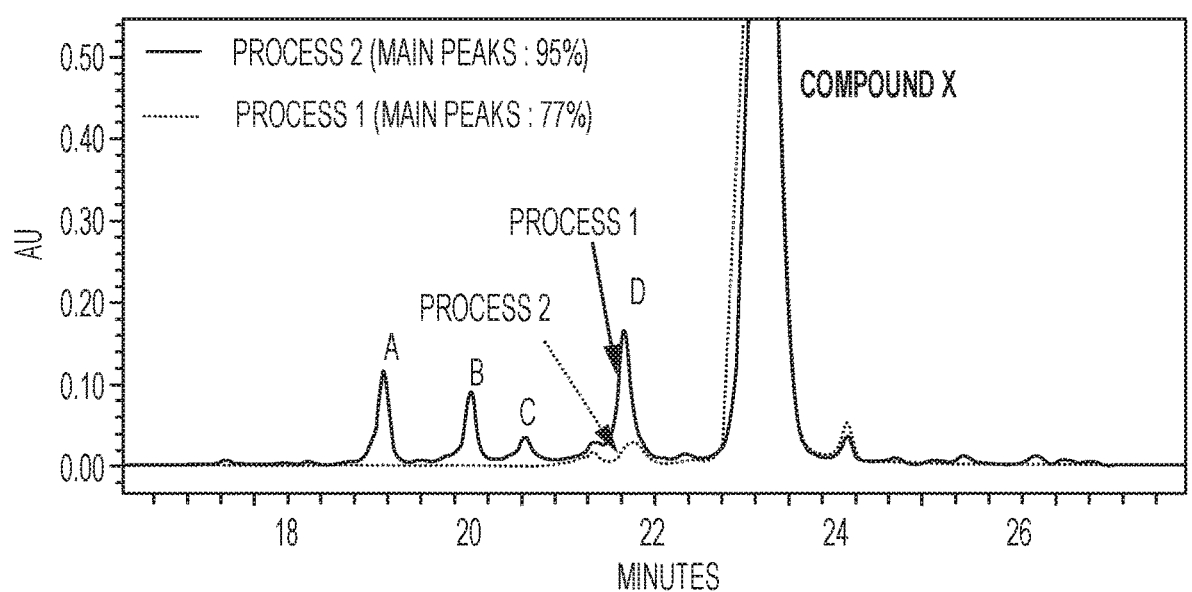
FIG. 7B shows characterization of exemplary C3 fusion protein drug substance produced by Process 1 and Process 2 after the fermentation and downstream processes for both.

Ion exchange HPLC (IE-HPLC) was used to measure purity and/or identify product related substances (PRS). Characterization of exemplary C3 fusion protein drug substance produced by Process 1 for the final drug substance after the downstream processing using IE-HPLC is shown in FIG. 6. FIG. 7A shows an intermediate stage (after the fermentation but prior to the downstream processing) of Process 2. Characterization of exemplary C3 fusion protein drug substance produced by Process 2 for the final drug substance after the downstream processing using IE-HPLC is shown in FIG. 7B which is superimposed with the IE-HPLC of FIG. 6. As shown in FIGS. 6, 7A and 7B, in addition to the main peak corresponding to C3 fusion protein (compound X), IE-HPLC identified peaks A, B, C, D, and 1.05 as product related peaks. Process 1 corresponds to C3 fusion protein production with standard fermentation that does not employ high cell density fermentation with an exponential feeding strategy and without an intermediate cation-exchange column (cation exchange column II described in Example 2). Process 2 corresponds to C3 fusion protein produced with high cell density fermentation with an exponential feeding strategy and an intermediate cation exchange column (cation exchange column II described in Example 2) during the downstream processing. In FIG. 7B, the main peaks for Processes 1 and 2 were about 77% and 95%, respectively. Exemplary samples from Process 2 after the downstream processing showed ≥85.0% main product; ≤10.0% total acidic peaks; and ≤5.0% total basic peaks, as shown in Table 7 below.

Figure 5:
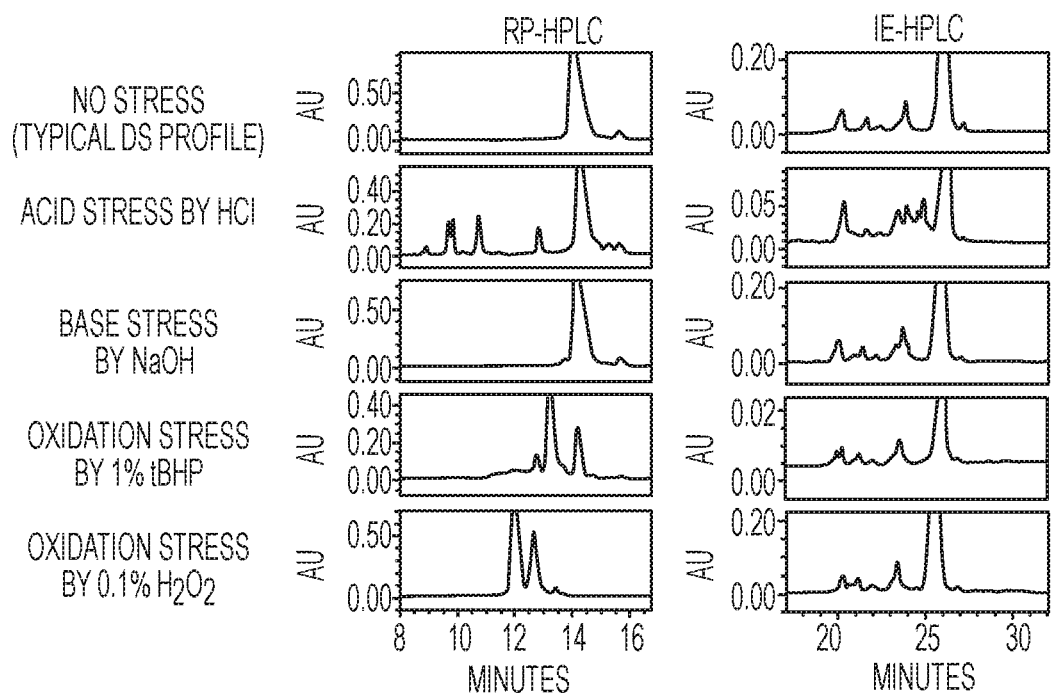
FIG. 5 shows exemplary stability profiles of exemplary C3 fusion protein drug substance before and after stress measured by RP-HPLC and IE-HPLC methods.

Stability of C3 fusion protein was tested using acid stress by HCl, base stress by NaOH, oxidation stress by 1% tBHP and by 1% $H_2O_2$. RP-HPLC and IE-HPLC (IEP) were used to determine the drug substance profile of C3 fusion protein after the stability stress tests (FIG. 5).

Figure 9:
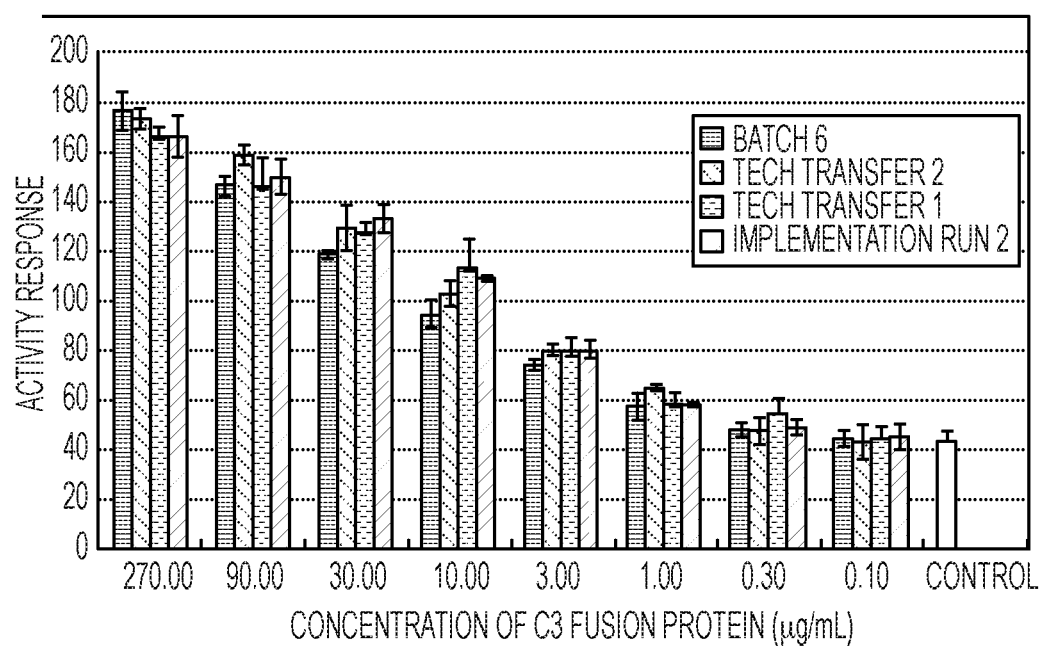
FIG. 9 shows biological activity of exemplary C3 fusion protein produced by Process 1 and Process 2.

Exemplary analytics shown in Table 6 from development runs show the exemplary Process 2 is robust and reproducible. As shown in FIG. 9, purified C3 fusion protein from various batches of the exemplary Process 2 described herein, exhibits comparable biological activity by a neurite outgrowth assay.

TABLE 6

Exemplary analytics

| Method | Process 1 | Process 2 (30 L) | Process 2 (300 L) |
|---|---|---|---|
| UV (g/L) | 12 | 35.8 | 35.0 |
| SDS-PAGE (band %) | 99.6 | 100.0 | 100.0 |
| IEP (area %) | 77.0 | 93.5 | 94.2 |
| SEC (area %) | 96.5 | 100.0 | 100.0 |
| RPLC (area %) | 93.6 | 92.5 | 93.3 |
| GH Assay (units) | 24 | 25 | 33 |
| Endotoxin (EU/mg) | <1 | $5.1 \times 10^{-4}$ | $2.9 \times 10^{-4}$ |
| Bioburden (cfu/10 mL) | <1 | <1 | <1 |

TABLE 6-continued

Exemplary analytics

| Method | Process 1 | Process 2 (30 L) | Process 2 (300 L) |
|---|---|---|---|
| DNA qPCR (ppb) | <1 | <8 | <9 |
| HCP (ppm) | <1 | 0.2 | <0.1 |

C3 fusion protein produced and purified according to Example 1 and 2 (Process 2), resulted in a protein composition that is a clear colorless liquid, with a pH between 6.0-7.0. The protein concentration was between 31-37 mg/ml. The identity was confirmed by isoelectric point (pI) using capillary isoelectric focusing and SDS-PAGE with Coomassie Blue staining. The pI compared to a reference standard with a pI±0.1. The SDS-PAGE confirmed C3 fusion protein migrates between 21 and 31 kDa. Purity and impurity analysis was performed with SDS-PAGE and Coomassie Blue staining ≥95.0% band purity and ≤5.0% band total impurities. Purity and impurity analysis of the C3 fusion protein composition was performed by SE-HPLC and confirmed ≥95.0% monomer and ≤5.0% total impurities. Purity and impurity analysis of the C3 fusion protein composition was performed by RP-HPLC and confirmed ≥85.0% purity and ≤15.0% total impurities. Purity and impurity analysis of the C3 fusion protein composition was performed by IE-HPLC and confirmed ≥85.0% major product, ≤10% total acidic peaks and ≤5.0% total basic peaks. The Glycohydrolase (GH) enzyme assay confirmed enzyme activity was between 20-40 Units (nmol of ADP-ribose/(mg protein×30 min) at 37° C. Residual DNA was measured by Real-Time PCR and confirmed to be ≤1000 pg/mg protein. Host cell proteins were measured by ELISA using standard off the shelf anti-HCP antibodies and confirmed to be ≤1000 ng/mg protein. Endotoxin (LAL) was confirmed ≤1 EU/mg protein. Bioburden (TAMC and TYMC) was confirmed ≤1 cfu/10 mL.

Additional attributes measured include Osmolality, Deamidation (RPLC-MS), Methionine oxidation (RPLC-MS), Peptide Map confirming ≥95.0% coverage (RPLC-MS), Molecular ion confirming molecular weight of 25,726±2 Da (RPLC-MS), and immunochemical homogeneity confirming a major band migrates between 21 and 31 kDa (Western blot). N-terminal sequencing by Edman Degradation confirmed (M)SAYSNTYQEF (SEQ ID NO: 5) and C-terminal sequencing by MS/MS and Edman degradation confirmed QGRHTPGTRL (SEQ ID NO: 7). Amino acid analysis by HCl hydrolysis confirmed 90-110% of expected mass. Additional attributes measured include Residual PPG-2000 Defoamer (LC-MS), Residual Isopropyl β-D-1-thio-galactopyranoside (IPTG) (LC-MS), Residual Edetate Disodium Dihydrate (CE), Far-UV Circular Dichroism, Near-UV Circular Dichroism, FTIR, Intrinsic Fluorescence, DSC, and Sedimentation velocity analytical ultracentrifugation (SV-AUC). Exemplary attributes of C3 fusion protein purified using Process 2 are shown in Table 7.

TABLE 7

Exemplary Attributes of Purified C3 Fusion Protein

| ATTRIBUTE | ACCEPTANCE CRITERIA |
|---|---|
| Appearance | Clear, colorless liquid |
| pH (at 25° C.) | 6.0-7.0 |
| Protein Concentration (UV at 280 nm) | 31-37 mg/mL |
| Identity Isoelectric Point (pI) (Capillary Isoelectric Focusing)$^a$ | Compares to reference standard (sample band is within reference material pI ± 0.1) |
| Identity (SDS-PAGE, Coomassie Blue Staining)$^a$ | Compares to reference standard (major band migrates between 21 and 31 kDa) |
| Purity and Impurity (SDS-PAGE, Coosmassie Blue Staining) | ≥95.0 band-% purity; ≤5.0% band-% total impurities |
| Purity and Impurity (SE-HPLC) | ≥95.0% monomer; ≤5.0% total impurities |
| Purity and Impurity (RP-HPLC) | ≥85.0% purity; ≤15.0% total impurities |
| Purity and Impurity (IE-HPLC) | ≥85.0% major product; ≤10.0% total acidic peaks ≤5.0% total basic peaks |
| Glycohydrolase Enzyme Assay | 20-40 nmol of ADP-ribose/ (mg protein × 30 min) at 37° C. |
| Residual DNA$^a$ (Real-Time PCR) | ≤1000 pg/mg protein |
| Host Cell Proteins$^a$ (ELISA) | ≤1000 ng/mg protein |
| Endotoxin (LAL) | ≤1 EU/mg |
| Bioburden | ≤1 cfu/10 mL |
| TAMC TYMC | ≤1 cfu/10 mL |
| Osmolality$^a$ | Report Results |
| Deamidation (RPLC-MS) | Report Results |
| Methionine oxidation (RPLC-MS) | Report Results |
| Peptide Map$^a$ (RPLC-MS) | Report Results (Target coverage: ≥95%) |
| Molecular ion$^a$ (RPLC-MS) | Report Results (Target value: molecular weight 25,726 ± 2 Da) |
| Immunochemical homogeneity$^a$ (Western blot) | Report Results (Target value: major band migrates between 21 and 31 kDa) |
| N-terminal sequencing$^a$ (Edman degradation) | Report Results (Target value: (M)SAYSNTYQEF (SEQ ID NO: 5)) |
| C-terminal sequencing$^a$ (MS/MS and Edman degradation) | Report Results (Target value: QGRHTPGTRL (SEQ ID NO: 7)) |
| Amino acid analysis$^a$ (HCl Hydrolysis) | Report Results (Target value: 90-110% of expected mass) |
| Residual PPG-2000 Defoamer$^a$ [LC-MS] | Report Results |
| Residual Isopropyl-β-D-thiogalatopyranoside (IPTG)$^a$ (LC-MS) | Report Results |
| Residual Edetate Disodium, Dihydrate$^a$ (CE) | Report Results |
| Far-UV Circular Dichroism$^a$ | Report Results |
| Near-UV Circular Dichroism$^a$ | Report Results |
| FTIR$^a$ | Report Results |
| Intrinsic Fluorescence$^a$ | Report Results |
| DSC$^a$ | Report Results |
| Sedimentation velocity analytical ultracentrifugation (SV-AUC)$^a$ | Report Results |

Table 8 below summarizes exemplary attributes of a purified C3 fusion protein composition suitable as drug product. Specifically, a protein drug product containing a purified C3 fusion protein is a clear, colorless liquid, essentially free of visible particulates. It has a pH of 6.0-7.0, with a protein concentration between 27-33 mg/mL. In addition to the quality attributes described above (see Table 7), the protein product was further evaluated for osmolality and sterility. Subvisible particulate matter was ≥10 μm: NMT 6000 per container or ≥25 μm: NMT 600 per container. Sub 10 μm particulate matter was measured and categorized as 2-5 μm particulate and 5-10 μm particulate. Container closure integrity was measured by the Dye immersion test and confirmed no dye detected.

TABLE 8

Exemplary attributes of a final product

| ATTRIBUTE | ACCEPTANCE CRITERIA |
|---|---|
| Appearance (Visual) | Clear, colorless liquid, essentially free of visible particulates |
| pH (at 25° C.) | 6.0-7.0 |
| Protein Concentration (UV at 280 nm) | 27-33 mg/mL |
| Identity (SDS-PAGE, Coomassie Blue Staining)$^a$ | Compares to reference standard; major band migrates between 21 and 31 KDa |
| Purity and Impurity (SDS-PAGE, Coomassie Blue Staining) | ≥95.0 band-% purity; ≤5.0% band-% total impurities |
| Purity and Impurity (SE-HPLC) | ≥95.0% monomer; ≤5.0% total impurities |
| Purity and Impurity (RP-HPLC) | ≥85.0% purity; ≤15.0% total impurities |
| Purity and Impurity (IE-HPLC) | ≥85.0% major product; ≤10.0% total acidic peaks ≤5.0% total basic peaks |
| Glycohydrolase Enzyme Assay | 20-40 nmol of ADP-ribose/ (mg protein × 30 min) at 37° C. |
| Endotoxin (LAL) | ≤1 EU/mg |
| Osmolality$^a$ | Report Results (mOsm/kg) |
| Sterility$^a$ | Sterile |
| Subvisible Particulate Matter | ≥10 μm: NMT 6000 per container ≥25 μm: NMT 600 per container |
| Sub 10 urn Particulate Matter | 2-5 μm: Report Results 5-10 μm: Report Results |
| Container Closure Integrity (Dye immersion test) | No dye detected |

Example 6. Compatibility Evaluation of C3 Fusion Protein and Fibrin Sealant Components This example illustrates exemplary methods, compositions and results for determining the compatibility and in-use stability of a C3 fusion protein when mixed with separate fibrin sealant components.

The exemplary C3 fusion protein used in these experiments was SEQ ID NO:1.

Initial methods comprised pre-mixing a C3 fusion protein at 37° C. with a calcium chloride-thrombin solution. Specifically, after premixing with thrombin, the product was to be administered within one hour. The fibrinogen was prepared separately by reconstituting with a solution containing aprotinin. Thrombin with a C3 fusion protein was administered simultaneously with fibrinogen/aprotinin using a Duploject Syringe to create the fibrin clot at the site of spinal cord injury. Several studies have been conducted to evaluate the compatibility and in-use stability of a C3 fusion protein when mixed with the separate fibrin sealant components using three methods: HPLC-MS, a neurite outgrowth bioassay, and glycohydrolase enzymatic activity (GH assay).

Assessment of C3 Fusion Protein+Thrombin Compatibility

When the SDS-PAGE method was used to assess the stability of a C3 fusion protein in a thrombin solution, a slightly faster migrating form was observed and, at the time, it was ascribed to limited digestion by proteolysis. Re-evaluation of this finding using high-performance liquid chromatography-mass spectrometry (HPLC-MS) confirmed that in the presence of thrombin there was a time-dependent proteolysis of the C3 fusion protein. The identified proteolytic site was located 7 amino acids from the C-terminal end of the protein and truncated the transport sequence as shown below. SEQ ID NO: 10 is an exemplary full length transport sequence, while SEQ ID NO: 11 is a truncated version of the exemplary transport sequence. The proteolytic site was not within the enzymatic region of the protein and it did not affect enzymatic activity as confirmed by the GH assay. The specific activity of the C3 fusion protein with a truncated transport sequence prepared in-house retained enzymatic activity similar to that of the full-length C3 fusion protein.

```
                                      (SEQ ID NO: 10)
EFVMNPANAQGRHTPGTRL (SEQ ID NO: 11)
EFVMNPANAQGR
```

Figure 12:
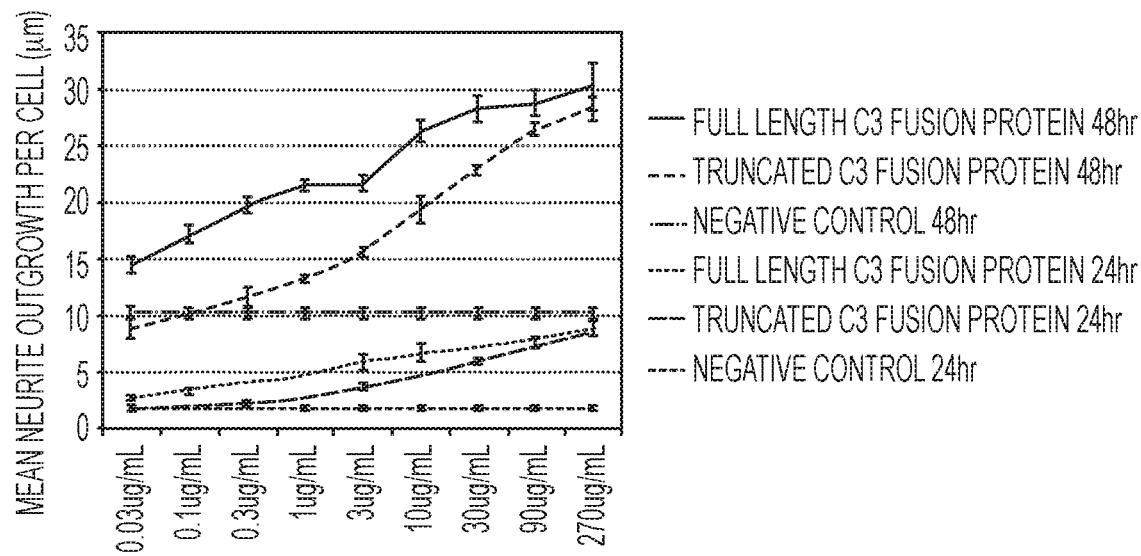
FIG. 12 depicts an exemplary comparison of neurite outgrowth assay results for a C3 fusion protein and a C3 fusion protein with a truncated transport sequence using dissociated primary human neurons at 24 and 48 hours in vitro.

An in vitro neurite outgrowth model was used to confirm the biological activity of the C3 fusion protein and the C3 fusion protein with truncated transport sequence. A comparison of neurite outgrowth induced by the full length C3 fusion protein or by the C3 fusion protein with truncated transport sequence was measured as a function of C3 fusion protein concentration. Dissociated primary human neurons were treated with either C3 fusion protein or C3 fusion protein with a truncated transport sequence (treated with thrombin and purified) at the indicated concentrations, fixed and the average neurite length per cell was measured using automated software. As shown in FIG. 12, when neurite outgrowth was observed at 24 and 48 hours after treatment, both the C3 fusion protein and C3 fusion protein with truncated transport sequence led to an increase in neurite outgrowth over the negative control. A modest difference in neurite outgrowth was observed between samples treated with the lower concentrations of the full length or truncated C3 fusion protein, while higher concentrations of both versions of the C3 fusion protein led to similar neurite outgrowth. Comparable results in neurite outgrowth were confirmed using cells from the rodent neuronal cell line, NG108 (not shown).

Assessment of C3 Fusion Protein+Fibrin Compatibility

To limit the effect of proteolysis, while still maintaining the order of addition used for the Ph1/2a studies, the amount of time for which the C3 fusion protein and thrombin were combined in the Duploject Syringe prior to administration could be limited to 1 hour. However, changing the order of addition such that the C3 fusion protein is added to the fibrinogen component in the Duploject Syringe was also considered. In either scenario, all components are mixed upon administration in order to form the clot. However, a change to the order of addition would provide for greater flexibility in preparation time and control variability upon application; though some truncation of the transport sequence would still occur once the fibrin clot is formed. Provided below, compatibility was established using HPLC-MS, a neurite outgrowth bioassay and the glycohydrolase enzymatic activity assay.

In the new preparation schema, the volume of C3 fusion protein solution (0.3 mL) was accommodated by removing 0.3 mL of aprotinin solution (from an initial volume of 1 mL) and the full amount of $CaCl_2$) was used, approximately 1 mL. This allowed for the same total volume to be delivered with the Duploject Syringe at the site of injury. Removal of some aprotinin to introduce the C3 fusion protein was not expected to have an impact on the rate of clot formation as this is dependent upon the concentration of thrombin.

Although aprotinin was used to stabilize the fibrin clot, the removal of 0.3 mL was not expected to significantly decrease the duration of the fibrin clot, which is approximately 10-14 days. Studies performed in mice with fibrin sealant with and without antifibrinolytic agents and reported in Evicel® Product Monograph US-2010/08/168 (see, for example, Summary of Preclinical Findings) showed no appreciable change in clot longevity.

Figure 13:
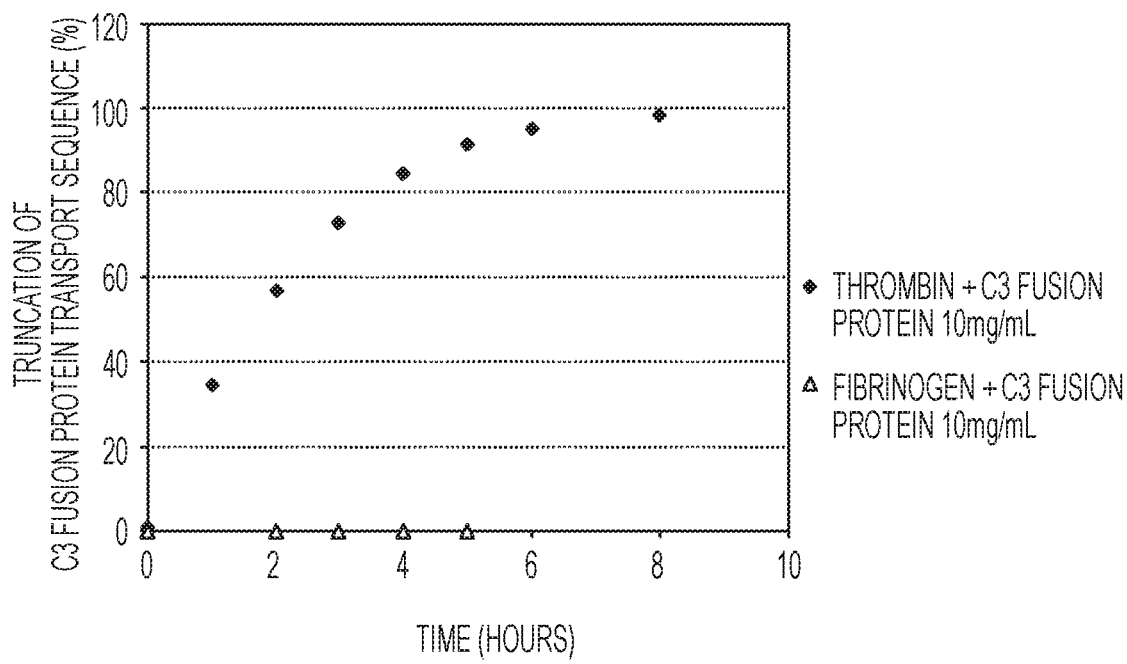
FIG. 13 depicts an exemplary graph comparing the effect of premixing a C3 fusion protein with thrombin vs. premixing a C3 fusion protein with fibrinogen as measured using high-performance liquid chromatography-mass spectrometry (HPLC-MS).

The compatibility of the C3 fusion protein with components of the fibrin sealant was studied using HPLC-MS. Samples were prepared using representative Ph2b/3 GMP material. As shown in FIG. 13, only when the C3 fusion protein was prepared with thrombin (diamonds) was truncation of the transport sequence observed. Truncation was not observed when the C3 fusion protein was prepared with fibrinogen (triangles).

The transport sequence attached to the C-terminal region of the C3 protein enhances penetration of the drug into neurons. In order to evaluate the cellular activity of the C3 fusion protein and determine whether or not a difference exists when the C3 fusion protein is prepared with fibrinogen or thrombin, an in vitro neurite outgrowth model was used.

Human cell neurite outgrowth was evaluated using a C3 fusion protein incubated with thrombin, or a C3 fusion protein incubated with fibrinogen at 37° C. for 4 hours before being applied to the cells. Dissociated primary human neurons were grown in the presence of the various samples for 24 hours, after which they were fixed and the average neurite length per cell was measured using automated software. Samples consisting of citrate buffer without C3 fusion protein, thrombin or fibrinogen were prepared as negative controls. Clinical GMP C3 fusion protein drug product (10 mg/mL) was combined with either thrombin or fibrinogen to create samples that were then diluted to a test concentration of 1 µg/mL. The same lot of C3 fusion drug product was also used as the C3 fusion protein positive control and was diluted to a concentration of 1 µg/mL.

Figure 14:
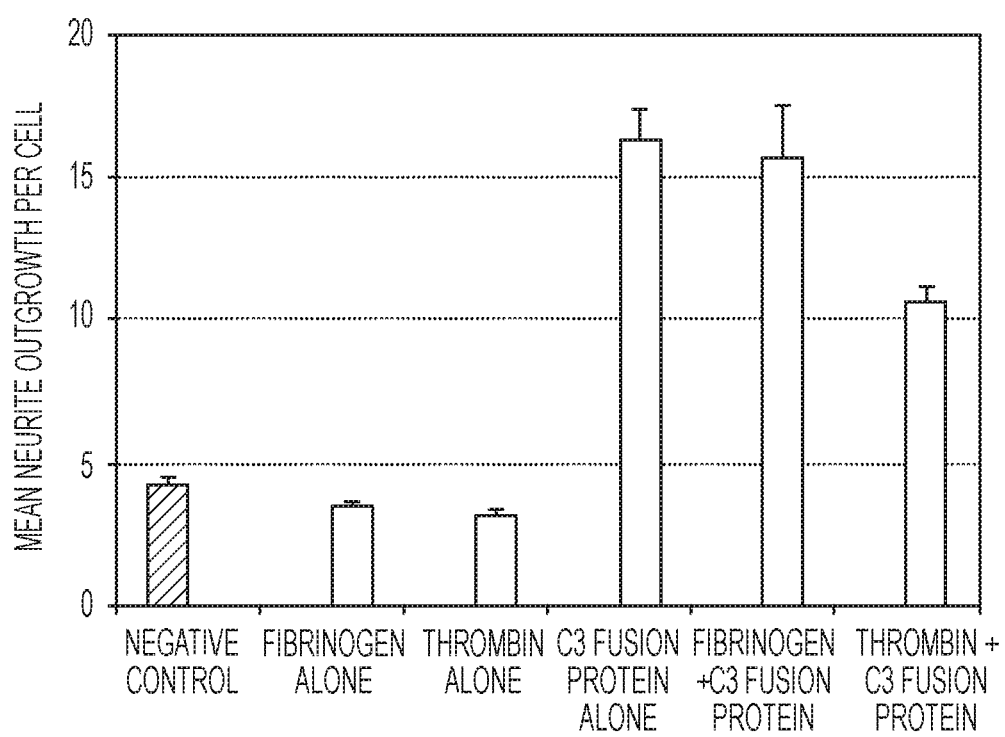
FIG. 14 depicts an exemplary graph comparing neurite outgrowth of dissociated human neurons 24 hours after being treated with a C3 fusion protein that was mixed with either thrombin or fibrinogen for 4 hours before treatment.

As shown in FIG. 14, after 24 hours of incubation, the C3 fusion protein combined with fibrinogen for 4 hours at 37° C. led to similar levels of neurite outgrowth as treatment with the C3 fusion protein alone. In comparison, C3 fusion protein combined with thrombin for 4 hours at 37° C. led to less neurite outgrowth compared to treatment with the C3 fusion protein alone.

In addition to HPLC-MS and a neurite outgrowth bioassay, a modified GH assay was used to determine and confirm the compatibility of the C3 fusion protein GMP drug product with components of the fibrin sealant. The GH assay was modified to use HPLC-fluorescence, instead of a plate reader, to separate interfering protein fluorescence. The results shown in Table 9 confirm that C3 fusion protein specific activity was constant over time in the presence of either the fibrinogen or thrombin sealant components. In enzymatic assays, the measured absolute rate of reaction is affected by the conditions of the test. In this case, the addition of fibrinogen affected the measured activity in the in vitro enzymatic assay but neither thrombin nor fibrinogen affected the potency of the drug (enzymatic activity). The reduced specific activity of the C3 fusion protein measured in the presence of fibrinogen was attributed to the increased viscosity of the fibrinogen solutions. The test concentration for the GH assay was 0.3 mg/mL C3 fusion protein; hence, the 10 mg/mL dose contained a greater concentration of fibrinogen than the 30 mg/mL strength after dilutions. Therefore, a higher concentration of fibrinogen interfered more with the assay in the 10 mg/mL strength as depicted in Table 9. In summary, whether the C3 fusion protein was premixed with thrombin or fibrinogen, the rate of enzymatic activity remained constant, demonstrating compatibility of the C3 fusion protein in the presence of the fibrin components.

TABLE 9

Effect of Thrombin and Fibrinogen Components of Fibrin Sealant on C3 Fusion Protein Glycohydrolase Enzyme Activity

| Sample Description and Conditions | Time Point | | | |
|---|---|---|---|---|
| C3 Fusion Protein in thrombin | 0 hours | 3 hours | 6 hours | 24 hours |
| 10 mg/mL C3 fusion protein, 37° C. | 28 | NT$^a$ | 24 | 28 |
| 30 mg/mL C3 fusion protein, 37° C. | 25 | NT$^a$ | 26 | 27 |
| C3 Fusion Protein in fibrinogen | | | | |
| 10 mg/mL C3 fusion protein, 37° C. | 3.3 | 2.9$^b$ | 4.8 | 4.7 |
| 30 mg/mL C3 fusion protein, 37° C. | 16 | 16 | 19 | 19 |

Units are nmol eADPr/protein weight/37° C. at 30 minutes
$^a$Not tested per study design
$^b$Tested at 1 hour Example 7. Formulation of C3-Thrombin-Fibrinogen Composition This example provides exemplary methods of preparing a pharmaceutically acceptable composition comprising a C3 fusion protein, a fibrinogen composition and a thrombin composition.

C3 Fusion Protein

Exemplary C3 fusion proteins comprise an amino acid sequence of a transport domain covalently linked to an amino acid sequence of an active domain, as described above. The amino acid sequence of the active domain can be selected from an ADP-ribosyl transferase C3, a fragment thereof retaining ADP-ribosyl transferase activity, or an amino acid sequence having at least 80% sequence identity thereto. The amino acid sequence of the transport domain can be selected from a subdomain of HIV Tat peptide or antennapedia peptide, a fragment of Tat peptide or antennapedia peptide, a Histidine tag, or an amino acid sequence having at least 80% sequence identity thereto.

Exemplary C3 fusion protein amino acid sequences are as follows:

(SEQ ID NO: 1)
SAYSNTYQEFTNIDQAKAWGNAQYKKYGLSKSEKEAIVSYTKSASEINGK

LRQNKGVINGFPSNLIKQVELLDKSFNKMKTPENIMLFRGDDPAYLGTEF

QNTLLNSNGTINKTAFEKAKAKFLNKDRLEYGYISTSLMNVSQFAGRPII

TKFKVAKGSKAGYIDPISAFAGQLEMLLPRHSTYHIDDMRLSSDGKQIII

TATMMGTAINPKEFVMNPANAQGRHTPGTRL (SEQ ID NO: 2)
MSAYSNTYQEFTNIDQAKAWGNAQYKKYGLSKSEKEAIVSYTKSASEING

KLRQNKGVINGFPSNLIKQVELLDKSFNKMKTPENIMLFRGDDPAYLGTE

FQNTLLNSNGTINKTAFEKAKAKFLNKDRLEYGYISTSLMNVSQFAGRPI

ITKFKVAKGSKAGYIDPISAFAGQLEMLLPRHSTYHIDDM

RLSSDGKQIIITATMMGTAINPKEFVMNPANAQGRHTPGTRL

-continued (SEQ ID NO: 8)
SAYSNTYQEFTNIDQAKAWGNAQYKKYGLSKSEKEAIVSYTKSASEINGK

LRQNKGVINGFPSNLIKQVELLDKSFNKMKTPENIMLFRGDDPAYLGTEF

QNTLLNSNGTINKTAFEKAKAKFLNKDRLEYGYISTSLMNVSQFAGRPII

TKFKVAKGSKAGYIDPISAFAGQLEMLLPRHSTYHIDDMRLSSDGKQIII

TATMMGTAINPKEFVMNPANAQGR (SEQ ID NO: 9)
MSAYSNTYQEFTNIDQAKAWGNAQYKKYGLSKSEKEAIVSYTKSASEING

KLRQNKGVINGFPSNLIKQVELLDKSFNKMKTPENIMLFRGDDPAYLGTE

FQNTLLNSNGTINKTAFEKAKAKFLNKDRLEYGYISTSLMNVSQFAGRPI

ITKFKVAKGSKAGYIDPISAFAGQLEMLLPRHSTYHIDDMRLSSDGKQII

ITATMMGTAINPKEFVMNPANAQGR

Fibrinogen Composition

An exemplary fibrinogen composition comprising a fibrinogen is a component of a TISSEEL kit. In a TISSEEL kit, the fibrinogen composition further comprises aprotinin, a fibrinolysis inhibitor. In these examples, a fibrinogen composition may also be referred to as "Sealer Protein Concentrate" or "Sealer Protein".

Thrombin Composition

An exemplary thrombin composition comprising thrombin is a component of a TISSEEL kit. In a TISSEEL kit, the thrombin composition further comprises calcium chloride.

Exemplary Formulation Protocol

The following is an exemplary formulation protocol for generating a therapeutic C3 fusion protein-thrombin-fibrinogen composition.

Exemplary preparation of a C3 fusion protein-thrombin-fibrinogen composition comprises 4 steps: (1) pre-warming of TISSEEL kit vials and thawing C3 fusion protein drug product; (2) thrombin preparation; (3) C3 fusion protein reconstitution in Sealer Protein Concentrate; and (4) loading of Thrombin and Sealer Protein+C3 fusion protein in DUPLOJECT syringe holder.

Pre-Warming of TISSEEL Kit Vials and Thawing of C3 Fusion Protein/Placebo Drug Product FIBRINOTHERM device is turned on and all vials from TISSEEL kit (Sealer Protein Concentrate, Fibrinolysis Inhibitor Solution, Thrombin and Calcium Chloride Solution) are placed into the wells of the FIBRINOTHERM, using the appropriately sized adapter rings. The vials are allowed to warm up for up to 5 minutes and magnetic stirring is not turned on at this time. C3 fusion protein drug product vials are thawed by being held in the palm of the hand for 1 to 2 minutes.

Thrombin Preparation

Flip-off caps are removed from Thrombin and Calcium Chloride Solution vials and wiped with a non-iodine based disinfectant. Packet A of the DUPLOJECT 2 mL/4 mL Fibrin Sealant Preparation and Application system kit within the TISSEEL kit is opened. One needle from Packet A is attached to the Black-Scaled sterile syringe also provided in Packet A. Using this Black-Scaled syringe, the entire volume from the Black-Capped Calcium Chloride Solution vial is withdrawn and transferred into the Black-Capped Thrombin vial. The empty syringe and needle are discarded in a sharps container. Care is taken not to inject air into the vial.

Contents of the Thrombin vial are gently swirled (not inverted) to ensure that the product is completely soaked and then the vial is returned to an appropriately sized heating well in the FIBRINOTHERM device. The Thrombin vial is left in the FIBRINOTHERM device at 37° C. until the solution is ready to be passed into the sterile field.

C3 Fusion Protein Reconstitution in Sealer Protein Concentrate

Flip-off caps are removed from the Blue-Capped Sealer Protein Concentrate and Fibrinolysis Inhibitor Solution vials and wiped with a non-iodine based disinfectant. C3 fusion protein drug product (or placebo) vial is wiped with a non-iodine based disinfectant. One needle from Packet A of the DUPLOJECT 2 mL/4 mL Fibrin Sealant Preparation and Application system kit within the TISSEEL kit is attached to the Blue-Scaled sterile syringe also provided in Packet A. Using this Blue-Scaled syringe, 0.3 mL is withdrawn from the Blue-Capped Fibrinolysis Inhibitor Solution vial and discarded in a waste container.

Packet A of the additional DUPLOJECT 2 mL/4 mL Fibrin Sealant Preparation and Application system kit is opened and one needle from this Packet A is attached to the Blue-Scaled syringe from this Packet A. Using this Blue-Scaled syringe, 0.3 mL is drawn from aluminum-capped C3 fusion protein drug product (or placebo) and injected into Blue-Capped Fibrinolysis Inhibitor Solution vial. C3 fusion protein drug product (or placebo) and Fibrinolysis Inhibitor Solution are mixed by swirling the vial gently.

Packet B of the additional DUPLOJECT 2 mL/4 mL Fibrin Sealant Preparation and Application system kit is opened and one needle from this Packet B is attached to the Blue-Scaled syringe from the Packet. Using this Blue-Scaled syringe, the entire volume is withdrawn from the Blue-Capped Fibrinolysis Inhibitor Solution vial (C3 fusion protein drug product (or placebo)+Fibrinolysis Inhibitor Solution), with the vial tilted slightly to facilitate removal of the entire solution. The C3 fusion protein drug product (or placebo)+Fibrinolysis Inhibitor Solution is injected into the Blue-Capped Sealer Protein Concentrate vial. The vial is then swirled (not inverted) to ensure that the product is completely soaked. The empty syringe and needle are discarded in a sharps container. Care is taken not to inject air into the vial.

The Blue-Capped Sealer Protein+C3 fusion protein (or placebo) vial is placed into the largest opening of the FIBRINOTHERM device with the appropriate adaptor. Magnetic stirring by the FIBRINOTHERM device is then turned on. The contents of the vial are allowed to stir until all the Sealer Protein is dissolved. Sealer Protein is effectively reconstituted once there were no visible clumps of the powder. At this time, the magnetic stirring by the FIBRINOTHERM device is turned off. If Sealer Protein does not dissolve within 20 minutes, the vial is discarded and a new TISSEEL kit and a new vial of C3 fusion protein (or placebo) are used. The Sealer protein solution is kept in the FIBRINOTHERM device (at 37° C.) without stirring until the solution is ready to be passed onto the sterile field. The solution is stirred shortly before being drawn up to ensure homogeneity.

Loading of Thrombin and Sealer Protein+C3 Fusion Protein (or Placebo) in DUPLOJECT Syringe Holder Solutions are loaded into DUPLOJECT according to the manufacturer's instructions by a Circulating Nurse and Scrub Nurse or designees. A brief description of the preparation procedure is included below.

Packet B of the DUPLOJECT 2 mL/4 mL Fibrin Sealant Preparation and Application system kit within the TISSEEL kit is opened into the sterile field. Within Packet B, Packets 1, 2, and 3 are opened. The Blue-Scaled and Black-Scaled syringes from Packet 1 of Packet B are assembled with the needles provided in Packet 1 of Packet B. While the Circulating Nurse or designee holds the Blue-Capped Sealer Protein+C3 fusion protein (or placebo) vial slightly tilted, Scrub Nurse or designee inserts the needle attached to the Blue-Scaled syringe from Packet 1 of Packet B into the Blue-Capped Sealer Protein+C3 fusion protein (or placebo) vial (bevel side down) and withdraws all of the Sealer Protein+C3 fusion protein (or placebo) Solution using firm, constant aspiration. Needle is discarded in sharps container. While the Circulating Nurse or designee holds the Black-Capped Thrombin Solution vial slightly tilted, Scrub Nurse inserts needle attached to Black-Scaled syringe from Packet 1 of Packet B into vial (bevel side down) and withdraws all of the Thrombin Solution using firm, constant aspiration. Needle is discarded in sharps container. Air bubbles are removed by striking the side of each syringe 1 or 2 times while keeping the tip in an upright position. It is then ensured that both syringes contain the same volume. The filled syringes (Blue-Scaled syringe and Black-Scaled Syringe) are snapped into the 2-syringe clip from Packet 2 of Packet B with the flanges in an up/down position (referring to the illustration in the instructions provided in TISSEEL kit). The joining piece from Packet 3 of Packet B is attached to the syringe nozzles, ensuring that both were firmly seated. The joining piece is secured by fastening the retaining strap to the double syringe clip. The syringe nozzles are aligned toward the middle for proper alignment. One of the application needles from Packet 3 of Packet B is fitted onto the joining piece. The needles are not primed because premature mixing will lead to blockage. The DUPLOJECT applicator is then ready for use.

Preparation of the C3 fusion protein (or placebo)+TISSEEL 2 mL kit is done within 4 hours prior to application. The preparation time begins when the C3 fusion protein (or placebo) is withdrawn from the freezer.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims.

Use of ordinal terms such as “first,” “second,” “third,” etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles “a” and “an” as used herein in the specification and in the claims, unless clearly indicated to the contrary, should be understood to include the plural referents. Claims or descriptions that include “or” between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

The invention claimed is:

1. A pharmaceutical composition comprising
a population of polypeptides, each of the polypeptides having a total of 231 amino acid residues and having an amino acid sequence at least 95% identical to SEQ ID NO:1,
wherein the first amino acid of each polypeptide is not a methionine, and
wherein the population of the polypeptides constitutes greater than 85% of the total amount of polypeptides in the composition.

2. The pharmaceutical composition of claim 1, wherein the pharmaceutical composition further comprises fibrinogen and does not contain thrombin.

3. The pharmaceutical composition of claim 2, wherein the pharmaceutical composition further comprises albumin, one or more blood coagulation factors, globulin, and/or one or more plasminogen-activator inhibitors or plasmin inhibitors.

4. The pharmaceutical composition of claim 3, wherein the one or more plasminogen-activator inhibitors or plasmin inhibitors comprise aprotinin.

5. The pharmaceutical composition of claim 1, wherein the population of polypeptides constitutes greater than 95% of the total amount of polypeptides in the composition.

6. A pharmaceutical composition comprising a first polypeptide and a second polypeptide, wherein:
the first polypeptide has a total of 231 amino acid residues and has an amino acid sequence at least 95% identical to SEQ ID NO:1 but does not contain a methionine at the N-terminus,
the second polypeptide is otherwise identical to the first polypeptide but contains a methionine at the N-terminus, and
the weight ratio of the first polypeptide to the second polypeptide is at least 6:1.

7. The pharmaceutical composition of claim 6, wherein the weight ratio of the first polypeptide to the second polypeptide is at least 20:1.

8. A pharmaceutical composition comprising a polypeptide having a total of 231 amino acid and having an amino acid sequence at least 95% identical to SEQ ID NO:1, wherein the polypeptide does not contain a methionine at the N-terminus, and
wherein the polypeptide is present at a concentration ranging from 1.0 mg/mL-40 mg/mL, as determined by UV spectrometry at 280 nm, or
wherein the composition contains less than 100 ng/mg host cell protein (HCP), or
wherein the composition contains less than $2.9 \times 10^{-4}$ EU/mg Endotoxin, or wherein the pharmaceutical composition comprises a buffer and has a pH ranging from 5.5-7.5 at 25° C.

9. The pharmaceutical composition of claim 8, wherein the polypeptide is present at a concentration ranging from 27 mg/ml to 33 mg/mL, as determined by UV spectrometry at 280 nm.

* * * * *